US012758147B2

(12) United States Patent
Schiller et al.

(10) Patent No.: US 12,758,147 B2
(45) Date of Patent: Oct. 13, 2026

(54) INTELLIGENT IMPLANTS AND ASSOCIATED ANTENNA AND DATA SAMPLING METHODS

(71) Applicant: CANARY MEDICAL INC., Vancouver (CA)

(72) Inventors: Peter J. Schiller, Shakopee, MN (US); Kimberly Salant, Asbury, NJ (US); Jeffrey M. Gross, Carlsbad, CA (US)

(73) Assignee: Canary Medical Inc., Vancouver (CA)

( * ) Notice: Subject to any disclaimer, the term of this patent is extended or adjusted under 35 U.S.C. 154(b) by 115 days.

(21) Appl. No.: 18/568,667

(22) PCT Filed: Jun. 14, 2022

(86) PCT No.: PCT/US2022/033414
§ 371 (c)(1),
(2) Date: Dec. 8, 2023

(87) PCT Pub. No.: WO2022/266085
PCT Pub. Date: Dec. 22, 2022

(65) Prior Publication Data

US 2024/0268756 A1 Aug. 15, 2024

Related U.S. Application Data

(60) Provisional application No. 63/210,425, filed on Jun. 14, 2021.

(51) Int. Cl.
*A61B 5/00* (2006.01)
*A61B 5/0205* (2006.01)
(Continued)

(52) U.S. Cl.
CPC .......... *A61B 5/4851* (2013.01); *A61B 5/0022* (2013.01); *A61B 5/0031* (2013.01);
(Continued)

(58) Field of Classification Search
CPC ....... A61B 5/075; A61B 5/0004; A61B 5/686; A61F 2/389; A61F 2/3859; A61H 3/00
See application file for complete search history.

(56) References Cited

U.S. PATENT DOCUMENTS

| | | | |
|---|---|---|---|
| 4,161,782 | A | 7/1979 | McCracken |
| 4,411,266 | A | 10/1983 | Cosman |

(Continued)

FOREIGN PATENT DOCUMENTS

| | | | |
|---|---|---|---|
| AT | 513434 B1 | 2/2015 | |
| CA | 1212501 A | 10/1986 | |

(Continued)

OTHER PUBLICATIONS

Das et al., "Electronic Packaging—Materials and Process Issues", National Seminar on Futuristic Material (NSFM-2004) Apr. 21-22, pp. 55-66 (Year: 2004).*

(Continued)

*Primary Examiner* — Boniface N Nganga

(57) ABSTRACT

An intelligent implant includes a component of an implantable prosthesis and an implantable reporting processor (IRP) associated with the implantable prosthesis. The IRP includes a housing having a casing and a cover coupled to the casing, an electronics assembly within the housing, and an antenna within the housing and coupled to the electronics assembly. The antenna is tuned to, and the electronics assembly is configured to enable communication through the antenna at both 2.45 GHz and 403 MHz (MICS channel). The antenna comprises a flat ribbon configured in a loop and having major surfaces. The antenna is encapsulated within the cover of the housing and is oriented therein with major surfaces of the antenna generally parallel with an inner surface of the cover.

19 Claims, 27 Drawing Sheets

(51) Int. Cl.

| | |
|---|---|
| ***A61B 5/07*** | (2006.01) |
| ***A61B 5/11*** | (2006.01) |
| ***A61B 5/145*** | (2006.01) |
| ***A61B 90/00*** | (2016.01) |
| *A61B 5/03* | (2006.01) |

(52) U.S. Cl.

CPC ............ *A61B 5/0205* (2013.01); *A61B 5/076* (2013.01); *A61B 5/1123* (2013.01); *A61B 5/14503* (2013.01); *A61B 5/6847* (2013.01); *A61B 5/7225* (2013.01); *A61B 5/7425* (2013.01); *A61B 90/06* (2016.02); *A61B 5/03* (2013.01); *A61B 2090/065* (2016.02); *A61B 2090/067* (2016.02); *A61B 2560/0209* (2013.01); *A61B 2560/0276* (2013.01); *A61B 2560/0406* (2013.01); *A61B 2560/045* (2013.01); *A61B 2560/0481* (2013.01); *A61B 2562/0219* (2013.01); *A61B 2562/0247* (2013.01); *A61B 2562/0261* (2013.01); *A61B 2562/0271* (2013.01); *A61B 2562/028* (2013.01); *A61B 2562/166* (2013.01)

(56) References Cited

U.S. PATENT DOCUMENTS

| | | | |
|---|---|---|---|
| 4,894,728 | A | 1/1990 | Goodman |
| 5,019,794 | A | 5/1991 | Letessier et al. |
| 5,042,504 | A | 8/1991 | Huberti |
| 5,245,109 | A | 9/1993 | Kaminsky et al. |
| 5,312,216 | A | 5/1994 | Hogg |
| 5,350,412 | A | 9/1994 | Hoegnelid et al. |
| 5,358,202 | A | 10/1994 | Tse et al. |
| 5,383,874 | A | 1/1995 | Jackson et al. |
| 5,413,604 | A | 5/1995 | Hodge |
| 5,626,581 | A | 5/1997 | Staehlin et al. |
| 5,672,954 | A | 9/1997 | Watanabe |
| 5,716,981 | A | 2/1998 | Hunter et al. |
| 5,833,603 | A | 11/1998 | Kovacs et al. |
| H1765 | H | 12/1998 | O'Phelan |
| 5,906,643 | A | 5/1999 | Walker |
| 6,019,794 | A | 2/2000 | Walker |
| 6,123,729 | A | 9/2000 | Insall et al. |
| 6,139,581 | A | 10/2000 | Engh et al. |
| 6,206,835 | B1 | 3/2001 | Spillman, Jr. et al. |
| 6,245,109 | B1 | 6/2001 | Mendes et al. |
| 6,358,202 | B1 | 3/2002 | Arent |
| 6,374,097 | B1 | 4/2002 | Kudou |
| 6,447,448 | B1 | 9/2002 | Ishikawa et al. |
| 6,610,096 | B2 | 8/2003 | Macdonald |
| 6,610,101 | B2 | 8/2003 | Herr et al. |
| 6,620,168 | B1 | 9/2003 | Lombardo et al. |
| 6,706,071 | B1 | 3/2004 | Wolter |
| 6,712,778 | B1 | 3/2004 | Jeffcoat et al. |
| 6,805,667 | B2 | 10/2004 | Christopherson et al. |
| 7,009,511 | B2 | 3/2006 | Mazar et al. |
| 7,097,662 | B2 | 8/2006 | Evans, III et al. |
| 7,127,300 | B2 | 10/2006 | Mazar et al. |
| 7,130,695 | B2 | 10/2006 | Czygan et al. |
| 7,141,026 | B2 | 11/2006 | Aminian et al. |
| 7,190,273 | B2 | 3/2007 | Liao et al. |
| 7,195,645 | B2 | 3/2007 | DiSilvestro et al. |
| 7,247,136 | B2 | 7/2007 | Feliss et al. |
| 7,328,131 | B2 | 2/2008 | Donofrio |
| 7,333,013 | B2 | 2/2008 | Berger |
| 7,347,874 | B2 | 3/2008 | DiSilvestro |
| 7,383,071 | B1 | 6/2008 | Russell et al. |
| 7,384,403 | B2 | 6/2008 | Sherman |
| 7,450,332 | B2 | 11/2008 | Pasolini et al. |
| 7,463,997 | B2 | 12/2008 | Pasolini et al. |
| 7,478,108 | B2 | 1/2009 | Townsend et al. |
| 7,553,923 | B2 | 6/2009 | Williams et al. |
| 7,559,951 | B2 | 7/2009 | DiSilvestro et al. |
| 7,603,894 | B2 | 10/2009 | Breed |
| 7,613,497 | B2 | 11/2009 | Govari et al. |
| 7,813,808 | B1 | 10/2010 | Doron et al. |
| 7,819,808 | B2 | 10/2010 | Oonuki |
| 7,874,673 | B2 | 1/2011 | Shinohara et al. |
| 7,889,070 | B2 | 2/2011 | Reeves et al. |
| 7,922,771 | B2 | 4/2011 | Otto et al. |
| 7,924,267 | B2 | 4/2011 | Sirtori |
| 8,029,566 | B2 | 10/2011 | Lozier et al. |
| 8,046,080 | B2 | 10/2011 | Von Arx et al. |
| 8,075,627 | B2 | 12/2011 | Caylor, III et al. |
| 8,080,064 | B2 | 12/2011 | Dietz et al. |
| 8,109,890 | B2 | 2/2012 | Kamiar et al. |
| 8,145,320 | B2 | 3/2012 | Corndorf et al. |
| 8,176,922 | B2 | 5/2012 | Sherman et al. |
| 8,241,296 | B2 | 8/2012 | Wasielewski |
| 8,244,368 | B2 | 8/2012 | Sherman |
| 8,245,583 | B2 | 8/2012 | Stein |
| 8,283,793 | B2 | 10/2012 | Pless |
| 8,311,632 | B2 | 11/2012 | Pless et al. |
| 8,317,869 | B2 | 11/2012 | Cloutier et al. |
| 8,372,420 | B2 | 2/2013 | Hunter et al. |
| 8,491,569 | B1 | 7/2013 | Anderson |
| 8,551,023 | B2 | 10/2013 | Sherman et al. |
| 8,556,888 | B2 | 10/2013 | Nields et al. |
| 8,634,808 | B1 | 1/2014 | Zhong et al. |
| 8,634,928 | B1 | 1/2014 | O'Driscoll et al. |
| 8,668,742 | B2 | 3/2014 | Caylor, III et al. |
| 8,721,643 | B2 | 5/2014 | Morgan et al. |
| 8,761,859 | B2 | 6/2014 | Roche |
| 8,876,739 | B2 | 11/2014 | Salarian et al. |
| 8,915,866 | B2 | 12/2014 | Nycz |
| 8,979,758 | B2 | 3/2015 | Stein et al. |
| 8,996,892 | B1 | 3/2015 | Chu et al. |
| 9,019,098 | B2 | 4/2015 | Okano |
| 9,307,932 | B2 | 4/2016 | Mariani et al. |
| 9,364,659 | B1 | 6/2016 | Rao |
| 9,368,105 | B1 | 6/2016 | Freed et al. |
| 9,390,724 | B2 | 7/2016 | List |
| 9,393,433 | B2 | 7/2016 | Parramon et al. |
| 9,424,840 | B1 | 8/2016 | Hart et al. |
| 9,445,930 | B2 | 9/2016 | Chen et al. |
| 9,451,919 | B2 | 9/2016 | Roche |
| 9,456,915 | B2 | 10/2016 | Chen et al. |
| 9,549,742 | B2 | 1/2017 | Berend et al. |
| 9,603,649 | B2 | 3/2017 | Matyas et al. |
| 9,629,583 | B2 | 4/2017 | Gradel et al. |
| 9,820,858 | B2 | 11/2017 | Harris et al. |
| 9,949,669 | B2 | 4/2018 | DiSilvestro et al. |
| 10,070,973 | B2 | 9/2018 | Sherman et al. |
| 10,137,305 | B2 | 11/2018 | Kane et al. |
| 10,219,699 | B2 | 3/2019 | Wilder et al. |
| 10,285,637 | B1 | 5/2019 | Hnat et al. |
| 10,492,686 | B2 | 12/2019 | Hunter et al. |
| 10,499,855 | B2 | 12/2019 | Hunter |
| 10,582,891 | B2 | 3/2020 | Wiedenhoefer et al. |
| 10,582,896 | B2 | 3/2020 | Revie et al. |
| 10,596,009 | B2 | 3/2020 | Mines et al. |
| 10,898,106 | B2 | 1/2021 | Bodewes et al. |
| 11,071,279 | B2 | 7/2021 | Singh et al. |
| 11,191,479 | B2 | 12/2021 | Bailey et al. |
| 11,684,260 | B2 | 6/2023 | Wiedenhoefer et al. |
| 11,786,126 | B2 | 10/2023 | Hunter et al. |
| 2001/0032059 | A1 | 10/2001 | Kelly et al. |
| 2001/0050087 | A1 | 12/2001 | Weissman et al. |
| 2002/0024450 | A1 | 2/2002 | Townsend et al. |
| 2002/0026224 | A1 | 2/2002 | Thompson et al. |
| 2002/0107576 | A1 | 8/2002 | Meyers et al. |
| 2002/0113685 | A1 | 8/2002 | Izaki et al. |
| 2002/0147416 | A1 | 10/2002 | Zogbi et al. |
| 2002/0156529 | A1 | 10/2002 | Li et al. |
| 2003/0004403 | A1 | 1/2003 | Drinan et al. |
| 2003/0025645 | A1 | 2/2003 | Amundson et al. |
| 2003/0069644 | A1 | 4/2003 | Kovacevic et al. |
| 2003/0100930 | A1 | 5/2003 | Cohen et al. |
| 2003/0204267 | A1 | 10/2003 | Hazebrouck et al. |
| 2004/0011137 | A1 | 1/2004 | Hnat et al. |
| 2004/0019382 | A1 | 1/2004 | Amirouche et al. |
| 2004/0019384 | A1 | 1/2004 | Kirking et al. |
| 2004/0083003 | A1 | 4/2004 | Wasielewski |

(56) References Cited

U.S. PATENT DOCUMENTS

| | | | |
|---|---|---|---|
| 2004/0098060 | A1 | 5/2004 | Ternes |
| 2004/0113790 | A1 | 6/2004 | Hamel et al. |
| 2004/0138757 | A1 | 7/2004 | Nadzadi et al. |
| 2004/0204635 | A1 | 10/2004 | Scharf et al. |
| 2004/0204766 | A1 | 10/2004 | Siebel |
| 2004/0211580 | A1 | 10/2004 | Wang et al. |
| 2004/0243148 | A1 | 12/2004 | Wasielewski |
| 2004/0243244 | A1 | 12/2004 | Otto et al. |
| 2004/0249464 | A1 | 12/2004 | Bindseil et al. |
| 2004/0249471 | A1 | 12/2004 | Bindseil et al. |
| 2005/0010299 | A1 | 1/2005 | Disilvestro |
| 2005/0010300 | A1 | 1/2005 | Disilvestro et al. |
| 2005/0010301 | A1 | 1/2005 | Disilvestro et al. |
| 2005/0012610 | A1 | 1/2005 | Liao et al. |
| 2005/0021126 | A1 | 1/2005 | Machan et al. |
| 2005/0027192 | A1 | 2/2005 | Govari et al. |
| 2005/0065408 | A1 | 3/2005 | Benderev |
| 2005/0137480 | A1 | 6/2005 | Alt et al. |
| 2005/0165317 | A1 | 7/2005 | Turner et al. |
| 2005/0171594 | A1 | 8/2005 | Machan et al. |
| 2005/0181005 | A1 | 8/2005 | Hunter et al. |
| 2005/0181009 | A1 | 8/2005 | Hunter et al. |
| 2005/0192557 | A1 | 9/2005 | Brauker et al. |
| 2005/0203583 | A1 | 9/2005 | Twetan et al. |
| 2005/0228410 | A1 | 10/2005 | Berreklouw |
| 2005/0242666 | A1 | 11/2005 | Huscher et al. |
| 2005/0245992 | A1 | 11/2005 | Persen et al. |
| 2005/0273170 | A1 | 12/2005 | Navarro et al. |
| 2005/0288563 | A1 | 12/2005 | Feliss et al. |
| 2006/0009856 | A1 | 1/2006 | Sherman et al. |
| 2006/0030771 | A1 | 2/2006 | Levine et al. |
| 2006/0030945 | A1 | 2/2006 | Wright |
| 2006/0036246 | A1 | 2/2006 | Carl et al. |
| 2006/0047283 | A1 | 3/2006 | Evans, III et al. |
| 2006/0069403 | A1 | 3/2006 | Shalon et al. |
| 2006/0111777 | A1 | 5/2006 | Chen |
| 2006/0116744 | A1 | 6/2006 | Von Arx et al. |
| 2006/0142670 | A1 | 6/2006 | Disilvestro et al. |
| 2006/0152377 | A1 | 7/2006 | Beebe et al. |
| 2006/0165317 | A1 | 7/2006 | Gzybowski |
| 2006/0184067 | A1 | 8/2006 | Clark et al. |
| 2006/0200121 | A1 | 9/2006 | Mowery |
| 2006/0224088 | A1 | 10/2006 | Roche |
| 2006/0229711 | A1 | 10/2006 | Yan et al. |
| 2006/0229730 | A1 | 10/2006 | Railey et al. |
| 2006/0247712 | A1 | 11/2006 | Fuller et al. |
| 2006/0271112 | A1 | 11/2006 | Martinson et al. |
| 2006/0271199 | A1 | 11/2006 | Johnson |
| 2006/0282168 | A1 | 12/2006 | Sherman et al. |
| 2007/0004994 | A1 | 1/2007 | Sherman |
| 2007/0005141 | A1 | 1/2007 | Sherman |
| 2007/0032749 | A1 | 2/2007 | Overall et al. |
| 2007/0034013 | A1 | 2/2007 | Moon et al. |
| 2007/0060955 | A1 | 3/2007 | Strother et al. |
| 2007/0067018 | A1 | 3/2007 | Miller |
| 2007/0088442 | A1 | 4/2007 | Cima et al. |
| 2007/0089518 | A1 | 4/2007 | Ericson et al. |
| 2007/0126696 | A1 | 6/2007 | Boillot |
| 2007/0151884 | A1 | 7/2007 | Thoes et al. |
| 2007/0161884 | A1 | 7/2007 | Black et al. |
| 2007/0167809 | A1 | 7/2007 | Dala-Krishna |
| 2007/0179628 | A1 | 8/2007 | Rochetin |
| 2007/0179739 | A1 | 8/2007 | Donofrio et al. |
| 2007/0185551 | A1 | 8/2007 | Meadows et al. |
| 2007/0211022 | A1 | 9/2007 | Boillot |
| 2007/0211023 | A1 | 9/2007 | Boillot |
| 2007/0233065 | A1 | 10/2007 | Donofrio et al. |
| 2007/0233267 | A1 | 10/2007 | Amirouche et al. |
| 2007/0234819 | A1 | 10/2007 | Amirouche et al. |
| 2007/0238984 | A1 | 10/2007 | Maschke et al. |
| 2007/0238992 | A1 | 10/2007 | Donofrio et al. |
| 2007/0239282 | A1 | 10/2007 | Caylor, III et al. |
| 2007/0265662 | A1 | 11/2007 | Ufford |
| 2007/0288194 | A1 | 12/2007 | Boillot |
| 2008/0020012 | A1 | 1/2008 | Ju et al. |
| 2008/0027679 | A1 | 1/2008 | Shklarski |
| 2008/0033527 | A1 | 2/2008 | Nunez et al. |
| 2008/0048878 | A1 | 2/2008 | Boillot |
| 2008/0065225 | A1 | 3/2008 | Wasielewski et al. |
| 2008/0076972 | A1 | 3/2008 | Dorogusker et al. |
| 2008/0088436 | A1 | 4/2008 | Reeves et al. |
| 2008/0114270 | A1 | 5/2008 | DiSilvestro et al. |
| 2008/0139954 | A1 | 6/2008 | Day et al. |
| 2008/0214903 | A1 | 9/2008 | Orbach |
| 2008/0215609 | A1 | 9/2008 | Cleveland et al. |
| 2008/0235621 | A1 | 9/2008 | Boillot |
| 2008/0275350 | A1 | 11/2008 | Liao et al. |
| 2008/0300597 | A1 | 12/2008 | Morgan et al. |
| 2008/0300659 | A1 | 12/2008 | Matos |
| 2008/0306325 | A1 | 12/2008 | Burnett et al. |
| 2008/0309481 | A1 | 12/2008 | Tanaka et al. |
| 2009/0005708 | A1 | 1/2009 | Johanson et al. |
| 2009/0005876 | A1 | 1/2009 | Dietz et al. |
| 2009/0012372 | A1 | 1/2009 | Burnett et al. |
| 2009/0048524 | A1 | 2/2009 | Wildau et al. |
| 2009/0076358 | A1 | 3/2009 | Reggiardo et al. |
| 2009/0088756 | A1 | 4/2009 | Anderson |
| 2009/0099570 | A1 | 4/2009 | Paradis et al. |
| 2009/0112523 | A1 | 4/2009 | Townsend et al. |
| 2009/0119222 | A1 | 5/2009 | O'Neil et al. |
| 2009/0149964 | A1 | 6/2009 | May et al. |
| 2009/0157146 | A1 | 6/2009 | Linder et al. |
| 2009/0187120 | A1 | 7/2009 | Nycz |
| 2009/0192533 | A1 | 7/2009 | Dlugos, Jr. et al. |
| 2009/0253587 | A1 | 10/2009 | Fernandez |
| 2009/0264894 | A1 | 10/2009 | Wasielewski |
| 2009/0299228 | A1 | 12/2009 | Lozier et al. |
| 2010/0014626 | A1 | 1/2010 | Fennell et al. |
| 2010/0057046 | A1 | 3/2010 | Stevens et al. |
| 2010/0100011 | A1 | 4/2010 | Roche |
| 2010/0145337 | A1 | 6/2010 | Janna et al. |
| 2010/0152621 | A1 | 6/2010 | Janna et al. |
| 2010/0164705 | A1 | 7/2010 | Blanchard |
| 2010/0191100 | A1 | 7/2010 | Anderson et al. |
| 2010/0204551 | A1 | 8/2010 | Roche |
| 2010/0204802 | A1 | 8/2010 | Wilson et al. |
| 2010/0204955 | A1 | 8/2010 | Roche et al. |
| 2010/0249533 | A1 | 9/2010 | Pierce et al. |
| 2010/0249787 | A1 | 9/2010 | Roche |
| 2010/0249790 | A1 | 9/2010 | Roche |
| 2010/0250284 | A1 | 9/2010 | Roche et al. |
| 2010/0262160 | A1 | 10/2010 | Boyden et al. |
| 2010/0285082 | A1 | 11/2010 | Fernandez |
| 2010/0287422 | A1 | 11/2010 | Miyazaki |
| 2010/0312188 | A1 | 12/2010 | Robertson et al. |
| 2010/0326187 | A1 | 12/2010 | Stein |
| 2010/0326194 | A1 | 12/2010 | Stein et al. |
| 2010/0326210 | A1 | 12/2010 | Stein et al. |
| 2010/0326211 | A1 | 12/2010 | Stein |
| 2010/0327848 | A1 | 12/2010 | Stein |
| 2010/0327880 | A1 | 12/2010 | Stein |
| 2010/0328077 | A1 | 12/2010 | Stein |
| 2010/0328098 | A1 | 12/2010 | Stein et al. |
| 2010/0331663 | A1 | 12/2010 | Stein |
| 2010/0331679 | A1 | 12/2010 | Stein |
| 2010/0331680 | A1 | 12/2010 | Stein |
| 2010/0331681 | A1 | 12/2010 | Stein et al. |
| 2010/0331682 | A1 | 12/2010 | Stein et al. |
| 2010/0331685 | A1 | 12/2010 | Stein et al. |
| 2010/0331687 | A1 | 12/2010 | Stein et al. |
| 2010/0331704 | A1 | 12/2010 | Stein et al. |
| 2010/0331718 | A1 | 12/2010 | Stein |
| 2010/0331733 | A1 | 12/2010 | Stein |
| 2010/0331734 | A1 | 12/2010 | Stein |
| 2010/0331738 | A1 | 12/2010 | Stein et al. |
| 2010/0331894 | A1 | 12/2010 | Stein |
| 2010/0331932 | A1 | 12/2010 | Stevenson et al. |
| 2010/0332152 | A1 | 12/2010 | Stein |
| 2011/0004076 | A1 | 1/2011 | Janna et al. |
| 2011/0015693 | A1 | 1/2011 | Williamson |
| 2011/0019595 | A1 | 1/2011 | Magar et al. |
| 2011/0054272 | A1 | 3/2011 | Derchak |
| 2011/0060220 | A1 | 3/2011 | Roche et al. |
| 2011/0063094 | A1 | 3/2011 | Meiertoberens et al. |

(56) References Cited

U.S. PATENT DOCUMENTS

2011/0066199 A1 3/2011 Linder et al.
2011/0071642 A1 3/2011 Moussa
2011/0077736 A1 3/2011 Rofougaran
2011/0077865 A1 3/2011 Chen et al.
2011/0087306 A1 4/2011 Goossen
2011/0087332 A1 4/2011 Bojarski et al.
2011/0092860 A1 4/2011 Salarian et al.
2011/0092948 A1 4/2011 Shachar et al.
2011/0098576 A1 4/2011 Hollstien
2011/0158206 A1 6/2011 Shrestha et al.
2011/0160572 A1 6/2011 McIntosh et al.
2011/0160583 A1 6/2011 Roche et al.
2011/0160616 A1 6/2011 Stein et al.
2011/0184740 A1 7/2011 Gruenstein et al.
2011/0196501 A1 8/2011 Michelson
2011/0200052 A1 8/2011 Mungo et al.
2011/0208444 A1 8/2011 Solinsky
2011/0213221 A1 9/2011 Roche
2011/0213413 A1 9/2011 Brown et al.
2011/0224500 A1 9/2011 Banet et al.
2011/0224564 A1 9/2011 Moon et al.
2011/0251694 A1 10/2011 Wasielewski
2011/0288436 A1 11/2011 Stone
2011/0288805 A1 11/2011 Dejnabadi et al.
2011/0319755 A1 12/2011 Stein et al.
2012/0022660 A1 1/2012 Wentorf
2012/0029316 A1 2/2012 Raptis et al.
2012/0035868 A1 2/2012 Roche et al.
2012/0071735 A1 3/2012 Caylor, III et al.
2012/0095526 A1 4/2012 Roche
2012/0116310 A1 5/2012 Forsell
2012/0123498 A1 5/2012 Gross
2012/0123716 A1 5/2012 Clark
2012/0130687 A1 5/2012 Otto et al.
2012/0152017 A1 6/2012 Stein et al.
2012/0157839 A1 6/2012 Stein
2012/0157884 A1 6/2012 Stein et al.
2012/0166680 A1 6/2012 Masoud et al.
2012/0190940 A1 7/2012 Stein et al.
2012/0190989 A1 7/2012 Kaiser et al.
2012/0191206 A1 7/2012 Stein et al.
2012/0216611 A1 8/2012 Stein et al.
2012/0220839 A1 8/2012 Stein et al.
2012/0226360 A1 9/2012 Stein et al.
2012/0226364 A1 9/2012 Kampas et al.
2012/0232834 A1 9/2012 Roche et al.
2012/0283600 A1 11/2012 Stein
2012/0313760 A1 12/2012 Okano
2012/0323333 A1 12/2012 Metzger
2012/0330367 A1 12/2012 Roche et al.
2013/0011008 A1 1/2013 Ikezoye et al.
2013/0023794 A1 1/2013 Stein et al.
2013/0023795 A1 1/2013 Stein et al.
2013/0027186 A1 1/2013 Cinbis et al.
2013/0079668 A1 3/2013 Stein et al.
2013/0079669 A1 3/2013 Stein et al.
2013/0079670 A1 3/2013 Stein et al.
2013/0079671 A1 3/2013 Stein et al.
2013/0079672 A1 3/2013 Stein et al.
2013/0079674 A1 3/2013 Stein et al.
2013/0079675 A1 3/2013 Stein et al.
2013/0079679 A1 3/2013 Roche et al.
2013/0079790 A1 3/2013 Stein et al.
2013/0079884 A1 3/2013 Stein et al.
2013/0109998 A1 5/2013 Swoboda et al.
2013/0110008 A1 5/2013 Bourget et al.
2013/0123684 A1 5/2013 Giuffrida et al.
2013/0144379 A1 6/2013 Najafi et al.
2013/0179110 A1 7/2013 Lee
2013/0197656 A1 8/2013 Conrad
2013/0215979 A1 8/2013 Yakovlev et al.
2013/0225949 A1 8/2013 Roche
2013/0225982 A1 8/2013 McIntosh et al.
2013/0226034 A1 8/2013 Stein et al.
2013/0226035 A1 8/2013 Stein et al.
2013/0252610 A1 9/2013 Kim et al.
2013/0261450 A1 10/2013 Stein et al.
2013/0268081 A1 10/2013 Stein et al.
2013/0281839 A1 10/2013 Yan et al.
2013/0317367 A1 11/2013 Shuler
2013/0325019 A1 12/2013 Thomas et al.
2013/0338455 A1 12/2013 Gradel et al.
2013/0338770 A1 12/2013 Boyden et al.
2014/0009262 A1 1/2014 Robertson et al.
2014/0025338 A1 1/2014 Blount et al.
2014/0031063 A1 1/2014 Park et al.
2014/0058289 A1 2/2014 Panken et al.
2014/0085102 A1 3/2014 McCormick
2014/0094715 A1 4/2014 Stein et al.
2014/0107796 A1 4/2014 Stein et al.
2014/0135589 A1 5/2014 Osorio
2014/0135616 A1 5/2014 Stein et al.
2014/0135624 A1 5/2014 Stein et al.
2014/0135655 A1 5/2014 Stein et al.
2014/0135773 A1 5/2014 Stein et al.
2014/0136143 A1 5/2014 Stein et al.
2014/0148676 A1 5/2014 Stein et al.
2014/0163645 A1 6/2014 Dinsmoor et al.
2014/0171754 A1 6/2014 Stein et al.
2014/0180697 A1 6/2014 Torok et al.
2014/0188007 A1 7/2014 Stein et al.
2014/0194707 A1 7/2014 Stein et al.
2014/0200584 A1 7/2014 Stein et al.
2014/0213867 A1 7/2014 Pletcher et al.
2014/0256324 A1 9/2014 Mohanty et al.
2014/0257047 A1 9/2014 Sillay et al.
2014/0275815 A1 9/2014 Stein et al.
2014/0275849 A1 9/2014 Acquista
2014/0275861 A1 9/2014 Kroh et al.
2014/0276240 A1 9/2014 Stein et al.
2014/0276241 A1 9/2014 Stein et al.
2014/0276885 A1 9/2014 Stein et al.
2014/0276887 A1 9/2014 Stein et al.
2014/0277542 A1 9/2014 Stein et al.
2014/0288464 A1 9/2014 Stein
2014/0296663 A1 10/2014 Boyden et al.
2014/0303739 A1 10/2014 Mentink et al.
2014/0322935 A1 10/2014 Filman et al.
2014/0328253 A1 11/2014 Lee et al.
2014/0330105 A1 11/2014 Roche
2014/0335490 A1 11/2014 Baarman et al.
2014/0336764 A1 11/2014 Masson et al.
2014/0378872 A1 12/2014 Hong et al.
2014/0379090 A1 12/2014 Diomidis et al.
2015/0025613 A1 1/2015 Nyberg, II et al.
2015/0032215 A1 1/2015 Slamin et al.
2015/0032217 A1 1/2015 Bojarski et al.
2015/0039093 A1 2/2015 McTighe et al.
2015/0051455 A1 2/2015 Wasielewski et al.
2015/0057775 A1 2/2015 Dong
2015/0057967 A1 2/2015 Albinali
2015/0080901 A1 3/2015 Stein
2015/0088253 A1 3/2015 Doll et al.
2015/0124675 A1 5/2015 Farmer et al.
2015/0127068 A1 5/2015 Simon et al.
2015/0164401 A1 6/2015 Toth et al.
2015/0170504 A1 6/2015 Jooste
2015/0202494 A1 7/2015 Hollenbach et al.
2015/0238304 A1 8/2015 Lamraoui
2015/0238691 A1 8/2015 Boyden et al.
2015/0335290 A1 11/2015 Hunter
2016/0007909 A1 1/2016 Singh et al.
2016/0025978 A1 1/2016 Mallinson
2016/0029952 A1 2/2016 Hunter
2016/0029998 A1 2/2016 Brister et al.
2016/0038087 A1 2/2016 Hunter
2016/0051823 A1 2/2016 Maile et al.
2016/0058582 A1 3/2016 Lenzi et al.
2016/0066816 A1 3/2016 Pless et al.
2016/0081762 A1 3/2016 Stein et al.
2016/0101281 A1 4/2016 Chen
2016/0106533 A1 4/2016 Galstian et al.
2016/0128573 A1 5/2016 Wilder et al.
2016/0166201 A1 6/2016 Stein et al.

(56) References Cited

U.S. PATENT DOCUMENTS

| | | | |
|---|---|---|---|
| 2016/0192878 | A1 | 7/2016 | Hunter |
| 2016/0199658 | A1 | 7/2016 | Nassif et al. |
| 2016/0232322 | A1 | 8/2016 | Mensinger et al. |
| 2016/0258779 | A1 | 9/2016 | Hol et al. |
| 2016/0269486 | A1 | 9/2016 | Gupta et al. |
| 2016/0302721 | A1 | 10/2016 | Wiedenhoefer et al. |
| 2016/0310066 | A1 | 10/2016 | Wiedenhoefer et al. |
| 2016/0310077 | A1 | 10/2016 | Hunter et al. |
| 2016/0338644 | A1 | 11/2016 | Connor |
| 2016/0340177 | A1 | 11/2016 | Takada |
| 2016/0374566 | A1 | 12/2016 | Fung et al. |
| 2016/0374588 | A1 | 12/2016 | Shariff et al. |
| 2017/0035593 | A1 | 2/2017 | Chen et al. |
| 2017/0042485 | A1 | 2/2017 | Chung et al. |
| 2017/0049963 | A1 | 2/2017 | Varsavsky et al. |
| 2017/0053764 | A1 | 2/2017 | Mori et al. |
| 2017/0056664 | A1 | 3/2017 | Kane et al. |
| 2017/0056722 | A1 | 3/2017 | Singh et al. |
| 2017/0065429 | A1 | 3/2017 | Behzadi et al. |
| 2017/0119316 | A1 | 5/2017 | Herrmann et al. |
| 2017/0119472 | A1 | 5/2017 | Herrmann et al. |
| 2017/0119566 | A1 | 5/2017 | Chen et al. |
| 2017/0138986 | A1 | 5/2017 | Kern |
| 2017/0143494 | A1 | 5/2017 | Mahfouz |
| 2017/0156288 | A1 | 6/2017 | Singh |
| 2017/0156632 | A1 | 6/2017 | Swiston et al. |
| 2017/0181825 | A1 | 6/2017 | Hunter |
| 2017/0189553 | A1 | 7/2017 | Hunter |
| 2017/0189752 | A1 | 7/2017 | Mohrman et al. |
| 2017/0196458 | A1 | 7/2017 | Ternes et al. |
| 2017/0196478 | A1 | 7/2017 | Hunter |
| 2017/0196499 | A1 | 7/2017 | Hunter |
| 2017/0196507 | A1 | 7/2017 | Singh et al. |
| 2017/0196508 | A1 | 7/2017 | Hunter |
| 2017/0196509 | A1 | 7/2017 | Hunter |
| 2017/0252187 | A1 | 9/2017 | Chapman et al. |
| 2017/0294949 | A1 | 10/2017 | Zhang et al. |
| 2017/0328931 | A1 | 11/2017 | Zhang et al. |
| 2017/0333080 | A1 | 11/2017 | Roschak et al. |
| 2018/0000380 | A1 | 1/2018 | Stein et al. |
| 2018/0028824 | A1 | 2/2018 | Pivonka et al. |
| 2018/0055443 | A1 | 3/2018 | Stein et al. |
| 2018/0064335 | A1 | 3/2018 | Rutschman et al. |
| 2018/0125365 | A1 | 5/2018 | Hunter et al. |
| 2018/0177607 | A1 | 6/2018 | Trabish et al. |
| 2018/0177611 | A1 | 6/2018 | Trabish et al. |
| 2018/0177612 | A1 | 6/2018 | Trabish et al. |
| 2018/0228428 | A1 | 8/2018 | Anker et al. |
| 2018/0235546 | A1 | 8/2018 | Hunter |
| 2019/0038361 | A1 | 2/2019 | Wasielewski |
| 2019/0038425 | A1 | 2/2019 | Otto et al. |
| 2019/0076033 | A1 | 3/2019 | Sweeney et al. |
| 2019/0076273 | A1 | 3/2019 | Goodchild et al. |
| 2019/0192072 | A1 | 6/2019 | Bailey et al. |
| 2019/0231555 | A1 | 8/2019 | Neubardt |
| 2019/0247197 | A1 | 8/2019 | Jagannathan et al. |
| 2019/0290451 | A1 | 9/2019 | Trabish et al. |
| 2019/0350518 | A1 | 11/2019 | Bailey et al. |
| 2019/0350519 | A1* | 11/2019 | Bailey ...................... A61F 2/12 |
| 2019/0350520 | A1 | 11/2019 | Bailey et al. |
| 2019/0350521 | A1 | 11/2019 | Bailey et al. |
| 2019/0350522 | A1 | 11/2019 | Bailey et al. |
| 2019/0350523 | A1 | 11/2019 | Bailey et al. |
| 2019/0380583 | A1 | 12/2019 | Danneels et al. |
| 2020/0054215 | A1 | 2/2020 | Roche |
| 2020/0093430 | A1 | 3/2020 | Bailey et al. |
| 2020/0093431 | A1 | 3/2020 | Bailey et al. |
| 2020/0155327 | A1 | 5/2020 | Suh et al. |
| 2021/0077241 | A1 | 3/2021 | Hunter |
| 2021/0369198 | A1 | 12/2021 | Gross et al. |
| 2021/0369199 | A1 | 12/2021 | Gross et al. |
| 2021/0369471 | A1 | 12/2021 | Gross et al. |
| 2022/0387186 | A1 | 12/2022 | Golemon, Jr. et al. |
| 2023/0285167 | A1 | 9/2023 | Alva et al. |
| 2023/0301802 | A1 | 9/2023 | Trousdale et al. |
| 2023/0414170 | A1 | 12/2023 | Bailey et al. |
| 2024/0156396 | A1 | 5/2024 | Amiot et al. |

FOREIGN PATENT DOCUMENTS

| | | | |
|---|---|---|---|
| CA | 2620247 | A1 | 3/2007 |
| CA | 3017932 | A1 | 9/2017 |
| CN | 2580920 | Y | 10/2003 |
| CN | 1806776 | A | 7/2006 |
| CN | 1899222 | A | 1/2007 |
| CN | 101060815 | A | 10/2007 |
| CN | 101254103 | A | 9/2008 |
| CN | 101257860 | A | 9/2008 |
| CN | 101273925 | A | 10/2008 |
| CN | 101287408 | A | 10/2008 |
| CN | 101296673 | A | 10/2008 |
| CN | 101426453 | A | 5/2009 |
| CN | 101484085 | A | 7/2009 |
| CN | 101495025 | A | 7/2009 |
| CN | 101536938 | A | 9/2009 |
| CN | 101573085 | A | 11/2009 |
| CN | 101773387 | A | 7/2010 |
| CN | 101849865 | A | 10/2010 |
| CN | 202036215 | U | 11/2011 |
| CN | 101773387 | B | 12/2011 |
| CN | 102612348 | A | 7/2012 |
| CN | 102688097 | A | 9/2012 |
| CN | 102740803 | A | 10/2012 |
| CN | 102885626 | A | 1/2013 |
| CN | 102905649 | A | 1/2013 |
| CN | 103313661 | A | 9/2013 |
| CN | 103458830 | A | 12/2013 |
| CN | 103735303 | A | 4/2014 |
| CN | 103957992 | A | 7/2014 |
| CN | 105283150 | A | 1/2016 |
| CN | 108136189 | A | 6/2018 |
| CN | 108430570 | A | 8/2018 |
| CN | 109310324 | A | 2/2019 |
| DE | 4322619 | C1 | 9/1994 |
| DE | 19924676 | A1 | 11/2000 |
| DE | 10342823 | A1 | 4/2005 |
| DE | 102004015976 | A1 | 10/2005 |
| EP | 1528902 | B1 | 11/2006 |
| EP | 2018825 | A1 | 1/2009 |
| EP | 1814471 | B1 | 3/2010 |
| EP | 2967879 | B1 | 1/2022 |
| JP | 2001046411 | A | 2/2001 |
| JP | 2003527926 | A | 9/2003 |
| JP | 2005520630 | A | 7/2005 |
| JP | 2005288172 | A | 10/2005 |
| JP | 2006055629 | A | 3/2006 |
| JP | 2006102498 | A | 4/2006 |
| JP | 2007083019 | A | 4/2007 |
| JP | 2007535372 | A | 12/2007 |
| JP | 2008501488 | A | 1/2008 |
| JP | 2008510584 | A | 4/2008 |
| JP | 2011514812 | A | 5/2011 |
| JP | 2013039444 | A | 2/2013 |
| JP | 2016525389 | A | 8/2016 |
| JP | 2017023436 | A | 2/2017 |
| JP | 2017510307 | A | 4/2017 |
| JP | 2022128381 | A | 9/2022 |
| KR | 101274641 | B1 | 6/2013 |
| KR | 20140133419 | A | 11/2014 |
| WO | 9733513 | A1 | 9/1997 |
| WO | 02064019 | A2 | 8/2002 |
| WO | 2004016204 | A1 | 2/2004 |
| WO | 2004091419 | A2 | 10/2004 |
| WO | 2005120203 | A2 | 12/2005 |
| WO | 2006078236 | A1 | 7/2006 |
| WO | 2006089069 | A2 | 8/2006 |
| WO | 2006105098 | A2 | 10/2006 |
| WO | 2006108065 | A2 | 10/2006 |
| WO | 2006113394 | A2 | 10/2006 |
| WO | 2008032316 | A2 | 3/2008 |
| WO | 2008035089 | A1 | 3/2008 |
| WO | 2008055229 | A2 | 5/2008 |
| WO | 2008103181 | A1 | 8/2008 |

(56) References Cited

FOREIGN PATENT DOCUMENTS

| | | | |
|---|---|---|---|
| WO | 2008152549 | A2 | 12/2008 |
| WO | 2009145633 | A1 | 12/2009 |
| WO | 2009148847 | A2 | 12/2009 |
| WO | 2010111678 | A2 | 9/2010 |
| WO | 2012006066 | A1 | 1/2012 |
| WO | 2012061825 | A2 | 5/2012 |
| WO | 2012095784 | A1 | 7/2012 |
| WO | 2012103549 | A1 | 8/2012 |
| WO | 2013022890 | A1 | 2/2013 |
| WO | 2013044117 | A1 | 3/2013 |
| WO | 2013044127 | A1 | 3/2013 |
| WO | 2013044157 | A1 | 3/2013 |
| WO | 2013044160 | A2 | 3/2013 |
| WO | 2013044165 | A2 | 3/2013 |
| WO | 2013044174 | A2 | 3/2013 |
| WO | 2013044165 | A3 | 5/2013 |
| WO | 2013131066 | A1 | 9/2013 |
| WO | 2014053956 | A1 | 4/2014 |
| WO | 2014100795 | A1 | 6/2014 |
| WO | 2014144070 | A1 | 9/2014 |
| WO | 2014144107 | A1 | 9/2014 |
| WO | 2014144707 | A1 | 9/2014 |
| WO | 2014209916 | A1 | 12/2014 |
| WO | 2015021807 | A1 | 2/2015 |
| WO | 2015038979 | A1 | 3/2015 |
| WO | 2015092747 | A2 | 6/2015 |
| WO | 2015188867 | A1 | 12/2015 |
| WO | 2015196131 | A1 | 12/2015 |
| WO | 2015200704 | A1 | 12/2015 |
| WO | 2015200707 | A1 | 12/2015 |
| WO | 2015200718 | A1 | 12/2015 |
| WO | 2015200720 | A2 | 12/2015 |
| WO | 2015200722 | A2 | 12/2015 |
| WO | 2015200723 | A1 | 12/2015 |
| WO | 2016044651 | A1 | 3/2016 |
| WO | 2016065205 | A1 | 4/2016 |
| WO | 2016174612 | A1 | 11/2016 |
| WO | 2016180653 | A1 | 11/2016 |
| WO | 2016180654 | A1 | 11/2016 |
| WO | 2017152153 | A1 | 9/2017 |
| WO | 2017165717 | A1 | 9/2017 |
| WO | 2018119360 | A1 | 6/2018 |
| WO | 2020206373 | A1 | 10/2020 |
| WO | 2020247890 | A1 | 12/2020 |

OTHER PUBLICATIONS

European Search Report for European Patent Application No. 24205658.8, dated Feb. 28, 2025, 9 Pages.

Singh U.K., et al., "Piezoelectric Power Scavenging of Mechanical Vibration Energy," Australian Mining Technology Conference, Oct. 2-4, 2007, pp. 111-118.

Xiang X., et al., "A Review of the Implantable Electronic Devices in Biology and Medicine," China Academic Journal Electronic Publishing House, vol. 32 (3), Mar. 3, 2004, pp. 462-467.

Yeh R., et al., "Single Mask, Large Force, and Large Displacement Electrostatic Linear Inchworm Motors," Journal of Microelectromechanical Systems, Aug. 4, 2002, vol. 11, No. 4, pp. 330-336, XP011064780.

Yiming L., et al., "Application of Wireless Sensor Networks in Healthcare," Chinese Journal of Medical Instrumentation, vol. 37, No. 5, Dec. 31, 2013, pp. 351-354 and Figure 1.

Yoon C., MD., et al., "Medial Tibial Periprosthetic Bone Resorption and Its Effect on Clinical Outcomes after Total Knee Arthroplasty: Cobalt-Chromium versus Titanium Implants," The Journal of Arthroplasty, Accepted Manuscript on Apr. 16, 2018, 43 Pages.

Yun K-S., et al., "A Surface-Tension Driven Micropump for Low-voltage and Low-Power Operations", Journal of Microelectromechanical Systems, Oct. 5, 2002, vol. 11, No. 5, pp. 454-461, DOI: 10.1109/JMEMS.2002.803286, XP001192816.

Zimmer: "Persona The Personalized Knee Systems," Brochure, 2014, 12 Pages.

Zimmer: "Zimmer NexGen RH Knee Brochure," 8 Pages.

Bergmann G., et al., "Standardized Loads Acting in Knee Implants", PLoS ONE, Public Library of Science, vol. 9, No. 1: e86035, Jan. 23, 2014, pp. 1-12.

Ai-Fakih E., et al., "The Use of Fiber Bragg Grating Sensors in Biomechanics and Rehabilitation Applications: The State-of-the-Art and Ongoing Research Topics," Sensors, Sep. 25, 2012, vol. 12, No. 10, pp. 12890-12926.

Almouahed S., et al., "New Trends in Instrumented Knee Prostheses," International Conference on Information and Communication Technologies: From Theory to Applications, Apr. 7-11, 2008, 6 Pages.

Angers-Goulet M., et al., "Up to Seven Years' Follow-up of Short Cemented Stems in Complex Primary Total Knee Arthroplasty: a Prospective Study," The Knee, Accepted on May 13, 2017, vol. 24, pp. 1166-1174.

Arami A., et al., "Accurate Measurement of Concurrent Flexion-Extension and Internal-External Rotations in Smart Knee Prostheses," IEEE Transactions on BioMedical Engineering, Sep. 2013, vol. 60, No. 9, pp. 2504-2510.

Arami A., et al., "Instrumented Prosthesis for Knee Implant Monitoring," IEEE International Conference on Automation Science and Engineering, Trieste, Italy, Aug. 24-27, 2011, pp. 828-835.

Bosch Press Release: "Bosch Sensortec Launches First IMU with Sub 1mA Current Consumption", Jun. 25, 2014, 3 Pages.

Bosch Sensortec: Bosch for BMI160 Small, Low—Power Inertial Measurement Unit, Jan. 15, 2015, 2 Pages.

Bosch Sensortec: "Data Sheet for BMI 160 Small, Low Power Inertial Measurement Unit," Document Revision 0.8, Release Date Feb. 10, 2015, No. BST-BMI160-DS000-07, 110 Pages.

Chandrakasan A.P., et al., "Next Generation Micro-Power Systems," Symposium on VLSI Circuits Digest of Technical Papers, 2008, pp. 1-5, 04 pages.

Christian R., MD., et al., "Short-keeled Cemented Tibial Components Show an Increased Risk for Aseptic Loosening," Clinical Orthopaedics and Related Research, Mar. 2013, vol. 471, No. 3, pp. 1008-1013.

Cushner F., MD., et al., "Feasibility and Compliance of Monitoring Post-Operative Activity Levels in TKA Patients Using Wireless Technology," Lenox Hill Hospital, Northwell Health, PPT Presentation, 1 Page.

D'Apuzzo M.R., et al., "Morbid Obesity Independently Impacts Complications, Mortality, and Resource Use After TKA," Clinical Orthopaedics and Related Research, Jan. 2015, Published Online on May 13, 2014, vol. 473, No. 01, pp. 57-63.

European Search Report in European Patent Application No. 23177756.6, dated Nov. 8, 2023, 8 Pages.

Extended European Search Report for European Application No. 14762269.0, mailed Oct. 24, 2016, 08 Pages.

Extended European Search Report for European Application No. 14762650.1, mailed Jul. 21, 2017, 10 Pages.

Extended European Search Report for European Application No. 14817352.9, mailed Jun. 13, 2017, 15 Pages.

Extended European Search Report for European Application No. 15812631.8, mailed Nov. 12, 2018, 17 Pages.

Extended European Search Report for European Application No. 15842678.3, mailed Feb. 5, 2019, 13 Pages.

Extended European Search Report for European Application No. 17771204.9, mailed Feb. 28, 2020, 09 Pages.

Extended European Search Report for European Application No. 20214094.3, mailed May 28, 2021, 07 Pages.

Extended European Search Report for European Application No. 22153300.3, mailed Jul. 18, 2022, 07 Pages.

Forchelet D., et al., "Enclosed Electronic System for Force Measurements in Knee Implants," Sensors, Aug. 14, 2014, vol. 14, pp. 15009-15021.

Graichen F., et al., "Hip Endoprosthesis for in Vivo Measurement of Joint Force and Temperature," Journal of biomechanics, 1999, vol. 32, No. 10, pp. 1113-1117.

Heinlein B., et al., "Design, Calibration and Pre-clinical Testing of an Instrumented Tibial Tray," Journal of biomechanics, 2007, vol. 40, pp. S4-S10.

(56) References Cited

OTHER PUBLICATIONS

International Preliminary Report on Patentability for International Application No. PCT/US2014/028381, mailed Sep. 24, 2015, 13 Pages.
International Preliminary Report on Patentability for International Application No. PCT/US2014/043736, mailed Jan. 7, 2016, 11 Pages.
International Preliminary Report on Patentability for International Application No. PCT/US2015/050789, mailed Mar. 30, 2017, 07 Pages.
International Preliminary Report on Patentability for International Application No. PCT/US2017/023916, mailed Oct. 4, 2018, 20 Pages.
International Preliminary Report on Patentability for International Application No. PCT/US2020/036516, mailed Dec. 16, 2021, 10 Pages.
International Search Report and Written Opinion for International Application No. PCT/US2014/028381, mailed Jul. 7, 2014, 15 Pages.
International Search Report and Written Opinion for International Application No. PCT/US2014/043736, mailed Oct. 15, 2014, 15 Pages.
International Search Report and Written Opinion for International Application No. PCT/US2015/050789, mailed Feb. 1, 2016, 10 Pages.
International Search Report and Written Opinion for International Application No. PCT/US2017/023916, mailed Aug. 2, 2017, 23 Pages.
International Search Report and Written Opinion for International Application No. PCT/US2020/036516, mailed Oct. 30, 2020, 14 Pages.
International Search Report and Written Opinion for International Application No. PCT/US2022/033414, mailed Oct. 26, 2022, 26 Pages.
Jacq C., et al., "Investigation of Polymer Thick-Film Piezoresistors for Medical Wrist Rehabilitation and Artificial Knee Load Sensors," Procedia Engineering, 2014, vol. 87, pp. 1194-1197.
Kroft S., "The Data Brokers: Selling your Personal Information," Extracted from Google on Sep. 4, 2014 is a script from "The Data Brokers" Aired on Mar. 9, 2014 on 60 Minutes CBS, pp. 1-8.
Loh N.C., et al., "Sub-10 cm3 Interferometric Accelerometer with Nano-g Resolution," Journal of Microelectromechanical Systems, vol. 11, No. 3, Jun. 2002, pp. 182-187.
Malin A.S., MD., et al., "Routine Surveillance of Modular PFC TKA Shows Increasing Failures after 10 Years," Clinical Orthopaedics and Related Research, Sep. 2010, vol. 468, No. 9, pp. 2469-2476.
Old A.B., et al., "Revision of Total Knee Arthroplasties Performed in Young, Active Patients with Posttraumatic Arthritis and Osteoarthritis," J. Knee Surg, Nov. 2017, vol. 30, No. 9, pp. 905-908, 1 Page.
Park M-H., Md., et al., "Using a Tibial Short Extension Stem Reduces Tibial Component Loosening After Primary Total Knee Arthroplasty in Severely Varus Knees: Long-term Survival Analysis with Propensity Score Matching," The Journal of Arthroplasty, vol. 33, 2018, pp. 2512-2517.
Parratte S., MD., et al., "Do Stemmed Tibial Components in Total Knee Arthroplasty Improve Outcomes in Patients with Obesity?," Clinical Orthopaedics and Related Research, Jan. 2017, vol. 475, No. 1, pp. 137-145.
Partial Supplementary European Search Report for European Application No. 14762650.1, mailed Apr. 13, 2017, 08 Pages.
Partial Supplementary European Search Report for European Application No. 14762650.1, mailed Mar. 17, 2017, 08 Pages.
Partial Supplementary European Search Report for European Application No. 14817352.9, mailed Feb. 14, 2017, 09 Pages.
Partial Supplementary European Search Report for European Application No. 15842678.3, mailed Oct. 16, 2018, 15 Pages.
Patil S., MD., et al., "How Do Knee Implants Perform Past the Second Decade? Nineteen- to 25-year Followup of he Press-fit Condylar Design TKA," Clinical Orthopaedics and Related Research, Jan. 2015, vol. 473, No. 1, pp. 135-140.
Polla D.L., et al., "Microdevices in Medicine," Annual Review Of Biomedical Engineering, 2000, vol. 02, pp. 551-576.
Ries M.D., "Endosteal Referencing in Revision Total Knee Arthroplasty," The Journal of Arthroplasty, 1998, vol. 13, No. 1, pp. 85-91.
Simoncini M., "Design And Integration Of An Instrumented Knee Prosthesis," Thesis No. 6379, 2014, Federal Polytechnic School of Lausanne, 162 Pages.
Laqua, D. "Intelligent Power Management enables Autonomous Power Supply of Sensor Systems for Modern Prostheses." Biomedical Engineering-Biomedizinische Technik. suppl. 1 57 : 247-250. Walter De Gruyter Gmbh. (Sep. 2012) ( Year: 2012).
Xiangjiang R., et al., "Sports Rehabilitation Exercise Prescription Medical Supervision" Guangxi Normal University Press, Jun. 2000, pp. 28-31.
Supplementary European Search Report in European Patent Application No. 22825659.0, dated Sep. 24, 2025, 18 Pages.

* cited by examiner

INTELLIGENT IMPLANTS AND ASSOCIATED ANTENNA AND DATA SAMPLING METHODS

INCORPORATION BY REFERENCE TO ANY PRIORITY APPLICATIONS

Any and all applications for which a foreign or domestic priority claim is identified in the Application Data Sheet as filed with the present application are hereby incorporated by reference.

TECHNICAL FIELD

The present disclosure relates generally to intelligent implants associated with implantable systems such as orthopedic (e.g., joint) replacement systems, and more particularly, to intelligent implants with implantable reporting processors that sample, record, and transmit information related to the placement and integrity of an implanted system, and the health of the patient in which the system is implanted, as well as features of intelligent implants including enhanced transmitting antenna configurations and data sampling methods.

BACKGROUND

Orthopedic replacement systems, such as knee arthroplasty systems, shoulder arthroplasty systems, and hip arthroplasty systems, may be configured to replace the entirety of a knee, shoulder, or hip joint, or to replace a part of knee, shoulder, or hip. Systems intended to replace the entirety of a knee, shoulder, or hip joint are referred to as total joint replacement systems or total joint arthroplasty (TJA), while those intended to replace a part of a joint are referred to as partial joint replacement systems. In either case, these joint replacement systems include implant structures or components.

With reference to FIG. 1A, a total knee arthroplasty (TKA) typically consists of a femoral component, a tibial component, a tibial insert, a tibial stem extension and a patella component. The patella component, which is implanted in front of the joint, is not shown. Collectively, these five implant structures or components may be referred to as any one of an implantable medical device, a knee prosthetic system, or total knee implant (TKI). Each of these five components may also be individually referred to as an implantable medical device. In either case, these components are designed to work together as a functional unit, to replace and provide the function of a natural knee joint.

With reference to FIG. 1B, a standard total shoulder arthroplasty (TSA) typically consists of a humeral stem component, a humeral stem adapter, a humeral head, a humeral head adapter (not shown), and a glenoid cap component. Collectively, these four implant structures or components may be referred to as any one of an implantable medical device, a shoulder prosthetic system, or total shoulder implant (TSI). Each of these four components may also be individually referred to as an implantable medical device. In either case, these components are designed to work together as a functional unit, to replace and provide the function of a natural shoulder joint.

With reference to FIG. 1C, a total hip arthroplasty (THA) typically consists of a femoral stem component, a femoral head component, a head liner component, and an acetabular cap component. Collectively, these four implant structures or components may be referred to as any one of an implantable medical device, a hip prosthetic system, or total hip implant (THI). Each of these four components may also be individually referred to as an implantable medical device. In either case, these components are designed to work together as a functional unit, to replace and provide the function of a natural hip joint.

Current commercial TJA systems have a long history of clinical use with implant duration regularly exceeding 10 years and with some reports supporting an 87% survivorship at 25 years. Clinicians currently monitor the progress of TJA patients post implant using a series of physical exams at 2-3 weeks, 6-8 weeks, 3 months, 6 months, 12 months, and yearly thereafter.

After the TJA has been implanted, and the patient begins to walk with the knee or hip prosthesis and move his arms or shoulder prosthesis, problems may occur and are sometimes hard to identify. Clinical exams are often limited in their ability to detect failure of the prosthesis; therefore, additional monitoring is often required such as CT scans, MRI scans or even nuclear scans. Given the continuum of care requirements over the lifetime of the implant, patients are encouraged to visit their clinician annually to review their health condition, monitor other joints, and assess the TJA implant's function. While the current standard of care affords the clinician and the healthcare system the ability to assess a patient's TJA function during the 90-day episode of care, the measurements are often subjective and lack temporal resolution to delineate small changes in functionality that could be a pre-cursor to larger mobility issues. The long-term (>1 year) follow up of TJA patients also poses a problem in that patients do not consistently see their clinicians annually. Rather, they often seek additional consultation only when there is pain or other symptoms.

Currently, there is no mechanism for reliably detecting misplacement, instability, or misalignment in the TJA without clinical visits and the hands and visual observations of an experienced health care provider. Even then, early identification of subclinical problems or conditions is either difficult or impossible since they are often too subtle to be detected on physical exam or demonstrable by radiographic studies. Furthermore, if detection were possible, corrective actions would be hampered by the fact that the specific amount of movement and/or degree of improper alignment cannot be accurately measured or quantified, making targeted, successful intervention unlikely. Existing external monitoring devices do not provide the fidelity required to detect instability since these devices are separated from the TJA by skin, muscle, and fat—each of which masks the mechanical signatures of instability and introduce anomalies such as flexure, tissue-borne acoustic noise, inconsistent sensor placement on the surface, and inconsistent location of the external sensor relative to the TJA.

In addition, a patient may experience a number of complications post-procedure. Such complications include neurological symptoms, pain, malfunction (blockage, loosening, etc.) and/or wear of the implant, movement or breakage of the implant, inflammation and/or infection. While some of these problems can be addressed with pharmaceutical products and/or further surgery, they are difficult to predict and prevent; often early identification of complications and side effects, although desirable, is difficult or impossible.

The present disclosure is directed to intelligent implants with implantable reporting processors that sample, record, and transmit information related to the placement and integrity of an implanted TJA, and the health of the patient in which the TJA is implanted, as well as intelligent implants having enhanced transmitting antenna configurations and data sampling methods.

SUMMARY

Briefly stated, the present disclosure relates to an intelligent implant that includes a component of an implantable prosthesis and an implantable reporting processor (IRP) that is associated with the component. The IRP includes a housing having a casing and a cover coupled to the casing, an electronics assembly within the housing, and an antenna within the housing and coupled to the electronics assembly. The antenna is tuned to, and the electronics assembly is configured to enable communication through the antenna at both 2.45 GHz and 403 MHz (MICS channel). The antenna comprises a flat ribbon configured in a loop and having major surfaces. The antenna is encapsulated within the cover of the housing and is oriented such that its major surfaces are generally parallel with an inner surface of the cover to maximize the area inside of the antenna loop.

The present disclosure also relates to an implantable reporting processor (IRP) configured to be associated with, e.g., mechanically coupled to, an implantable prosthesis. The IRP includes a housing having a casing and a cover coupled to the casing, an electronics assembly within the housing, and an antenna within the housing and coupled to the electronics assembly. The antenna includes a flat ribbon configured in a loop and having major surfaces, and is oriented within the cover of the housing with its major surfaces generally perpendicular to a plane bound by the loop to maximize the area inside of antenna loop.

The present disclosure also relates to an implantable reporting processor (IRP) configured to be integrated with an implantable prosthesis having a receptacle. The IRP includes a battery configured to fit within the receptacle, an electronics assembly coupled to the battery and configured to within the receptacle, an antenna coupled to the electronics assembly and configured for placement outside the receptacle, and a cover configured for placement outside the receptacle and enclosing the antenna. The antenna includes a flat ribbon configured in a loop and having major surfaces, and is oriented within the cover of the housing with its major surfaces generally perpendicular to a plane bound by the loop to maximize the area inside of antenna loop.

The present disclosure also relates to an intelligent implant that includes a component of an implantable prosthesis and an implantable reporting processor (IRP) associated with the component. The IRP includes a plurality of sensors and a controller. The IRP is configured to conduct low-resolution sampling through one or more of the plurality of sensors during a low-resolution window, and to conduct one of a medium-resolution sampling and a high-resolution sampling through one or more of the plurality of sensors during at least one medium-resolution window. During the medium-resolution window the IRP detects a significant motion event and conducts either a high-resolution sampling or a medium-resolution sampling. For example, the IRP may determine whether high resolution data needs to be collected or does not need to be collected. The IRP conducts high-resolution sampling in response to a determination that high resolution data needs to be collected, and conducts a medium-resolution sampling in response to a determination that high resolution data does not need to be collected. In another example, the IRP conducts either a high-resolution sampling or a medium-resolution sampling depending on whether the detected significant motion event is a specified detection or an unspecified detection. For example, a specified detection may be an initial detection of a significant motion event, and an unspecified detection may be a subsequent detection of a significant motion event after the initial detection. The IRP conducts high-resolution sampling in response to a specified detection of a significant motion event, and conducts a medium-resolution sampling in response to an unspecified detection of a significant motion event.

The present disclosure also relates to a method of sampling data from an implantable reporting processor (IRP) of an intelligent implant implanted in a patient. The IRP is configured to sample data in each of a low-resolution mode, a medium-resolution mode, and a high-resolution mode. The method includes conducting a low-resolution sampling during a low-resolution window, and conducting one of a medium-resolution sampling and a high-resolution sampling during at least one medium-resolution window. Conducting one of a medium-resolution sampling and a high-resolution sampling includes detecting a significant motion event, which may be either a specified detection or an unspecified detection. For example, a specified detection may be an initial detection of a significant motion event, and an unspecified detection may be a subsequent detection of a significant motion event after the initial detection. The method includes conducting a high-resolution sampling in response to a specified detection of a significant motion event, and conducting a medium-resolution sampling in response to an unspecified detection of a significant motion event.

The present disclosure also relates to an electronics assembly coupled to a battery of an implantable reporting processor associated with a component of an implantable prosthesis. The electronics assembly includes an inertial measurement unit (IMU) having a number of sensors, a discrete accelerometer that functions independent of the IMU, and a controller coupled to the IMU and the discrete accelerometer. The IMU has a plurality of accelerometers, a plurality of gyroscopes, a first measurement axis for which measurements are obtained by a first accelerometer and a first gyroscope, a second measurement axis for which measurements are obtained by a second accelerometer and a second gyroscope, and a third measurement axis for which measurements are obtained by a third accelerometer and a third gyroscope. The controller is configured to, during a low-resolution window, couple the discrete accelerometer to the battery and conduct a low-resolution sampling through the discrete accelerometer, and during a medium-resolution window: a) couple the discrete accelerometer to the battery and detect for a significant event, b) responsive to a specified detection of a significant motion event, coupled the IMU to the battery and conduct a high-resolution sampling through the plurality of accelerometers and the plurality of gyroscopes, and c) responsive to an unspecified detection of the significant motion event, couple the IMU to the battery and conduct a medium-resolution sampling through the plurality of accelerometers and the plurality of gyroscopes.

This Summary has been provided to introduce certain concepts in a simplified form that are further described in detail below in the Detailed Description. Except where otherwise expressly stated, this Summary is not intended to identify key or essential features of the claimed subject matter, nor is it intended to limit the scope of the claimed subject matter.

BRIEF DESCRIPTION OF THE DRAWINGS

Exemplary features of the present disclosure, its nature and various advantages will be apparent from the accompanying drawings and the following detailed description of various embodiments. Non-limiting and non-exhaustive embodiments are described with reference to the accompanying drawings, wherein like labels or reference numbers refer to like parts throughout the various views unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings. One or more embodiments are described hereinafter with reference to the accompanying drawings in which.

DETAILED DESCRIPTION

Figure 1A:
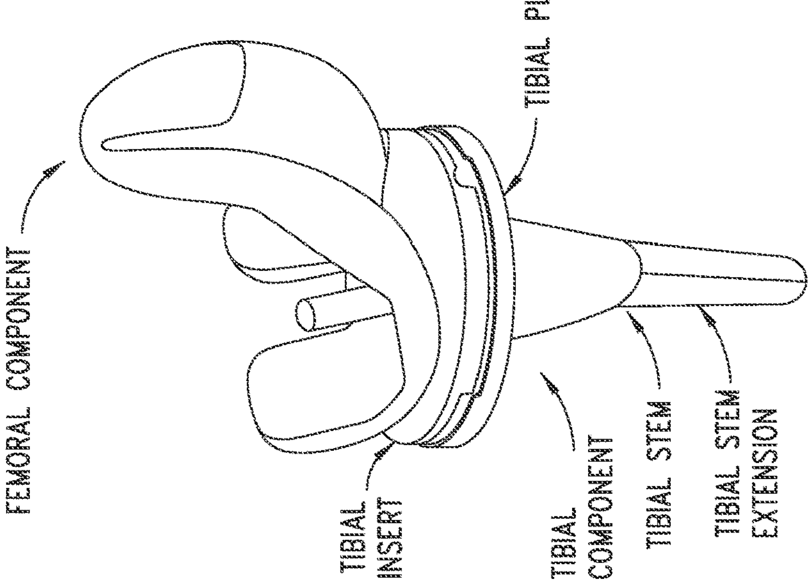
FIG. 1A (Prior Art)
FIG. 1A is an illustration of a conventional implantable medical device in the form of a knee prosthetic system, or total knee implant (TKI).

The present disclosure may be understood more readily by reference to the following detailed description of embodiments of the disclosure and the examples of implantable medical devices with implantable reporting processors. The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments.

The present disclosure refers to orthopedic implant procedures, for example, TJA (total joint arthroplasty) which term includes reference to the surgery and associated implantable medical devices such as a TJA prosthesis. Features of methods, devices and systems of the present disclosure may be illustrated herein by reference to a specific types of prosthesis, however, the disclosure should be understood to apply to any one or more orthopedic prosthesis, including for example, a TKA (total knee arthroplasty) prosthesis, such as a TKI (total knee implant) which may also be referred to as a TKA system; a TSA (total shoulder arthroplasty) prosthesis, such as a TSI (total shoulder implant) which may also be referred to as a TSI system; and a THA (total hip arthroplasty) prosthesis, such as a THI (total hip implant) which may also be referred to as a THA system, and a spinal implant system (e.g., a spinal fusion implant such as a spinal interbody cage, rod or plate, or a spinal non-fusion implant such as an artificial disc or expandable rod).

An "implantable medical device" as used in the present disclosure, is an implantable or implanted medical device that desirably replaces or functionally supplements a subject's natural body part. As used herein, the term "intelligent implant" refers to an implantable medical device with an implantable reporting processor, and is interchangeably referred to a "smart device." When the intelligent implant makes kinematic measurements, it may be referred to as a "kinematic implantable device." In describing embodiments of the present disclosure, reference may be made to a kinematic implantable device, however it should be understood that this is exemplary only of the intelligent medical devices which may be employed in the devices, methods, systems etc. of the present disclosure.

In one embodiment, the intelligent implant is an implanted or implantable medical device having an implantable reporting processor arranged to perform the functions as described herein. The intelligent implant may perform one or more of the following exemplary actions in order to characterize the post-implantation status of the intelligent implant: identifying the intelligent implant or a portion of the intelligent implant, e.g., by recognizing one or more unique identification codes for the intelligent implant or a portion of the intelligent implant; detecting, sensing and/or measuring parameters, which may collectively be referred to as monitoring parameters, in order to collect operational, kinematic, or other data about the intelligent implant or a portion of the intelligent implant and wherein such data may optionally be collected as a function of time; storing the collected data within the intelligent implant or a portion of the intelligent implant; and communicating the collected data and/or the stored data by a wireless means from the intelligent implant or a portion of the intelligent implant to an external computing device. The external computing device may have or otherwise have access to at least one data storage location such as found on a personal computer, a base station, a computer network, a cloud-based storage system, or another computing device that has access to such storage.

Non-limiting and non-exhaustive list of embodiments of intelligent implants include components of a total knee arthroplasty (TKA) system, a total hip arthroplasty (THA) system, a total shoulder arthroplasty (TSA) system, an intramedullary rod for arm or leg breakage repair, a scoliosis rod, a dynamic hip screw, a spinal interbody cage, a spinal rod, a spinal plate, a spinal interbody spacer, a spinal artificial disc, an annuloplasty ring, a heart valve, an intravascular stent, a vascular graft, and a vascular stent graft.

"Kinematic data," as used herein, individually or collectively includes some or all data associated with a particular kinematic implantable device and available for communication outside of the particular kinematic implantable device. For example, kinematic data may include raw data from one or more sensors of a kinematic implantable device, wherein the one or more sensors include such as gyroscopes, accelerometers, pedometers, strain gauges, and the like that produce data associated with motion, force, tension, velocity, or other mechanical forces. Kinematic data may also include processed data from one or more sensors, status data, operational data, control data, fault data, time data, scheduled data, event data, log data, and the like associated with the particular kinematic implantable device. In some cases, high resolution kinematic data includes kinematic data from one, many, or all of the sensors of the kinematic implantable device that is collected in higher quantities, resolution, from more sensors, more frequently, or the like.

In one embodiment, kinematics refers to the measurement of the positions, angles, velocities, and accelerations of body segments and joints during motion. Body segments are considered to be rigid bodies for the purposes of describing the motion of the body. They include the foot, shank (leg), thigh, pelvis, thorax, hand, forearm, upper-arm, and head. Joints between adjacent segments include the ankle (talocrural plus subtalar joints), knee, hip, wrist, elbow, shoulder and spine (or portions thereof). Position describes the location of a body segment or joint in space, measured in terms of distance, e.g., in meters. A related measurement called displacement refers to the position with respect to a starting position. In two dimensions, the position is given in Cartesian co-ordinates, with horizontal followed by vertical position. In one embodiment, a kinematic implant or intelligent kinematic implants obtains kinematic data, and optionally only obtains only kinematic data.

"Sensor" refers to a device that can be utilized to do one or more of detect, measure and/or monitor one or more different aspects of a body tissue (anatomy, physiology, metabolism, and/or function) and/or one or more aspects of the orthopedic device or implant. Representative examples of sensors suitable for use within the present disclosure include, for example, fluid pressure sensors, fluid volume sensors, contact sensors, position sensors, pulse pressure sensors, blood volume sensors, blood flow sensors, chemistry sensors (e.g., for blood and/or other fluids), metabolic sensors (e.g., for blood and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor. In certain embodiments, the sensor is a device that can be utilized to measure in a quantitative manner, one or more different aspects of a body tissue (anatomy, physiology, metabolism, and/or function) and/or one or more aspects of the orthopedic device or implant. In certain embodiments, the sensor is an accelerometer that can be utilized to measure in a quantitative manner, one or more different aspects of a body tissue (e.g., function) and/or one or more aspects of the orthopedic device or implant (e.g., alignment in the patient).

A wide variety of sensors (also referred to as Microelectromechanical Systems or "MEMS," or Nanoelectromechanical Systems or "NEMS," and BioMEMS or BioNEMS, see generally https://en.wikipedia.org/wiki/MEMS) can be utilized within the present disclosure. Representative patents and patent applications include U.S. Pat. Nos. 7,383,071, 7,450,332; 7,463,997, 7,924,267 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," J. Microelectromechanical Sys., 11:5, October 2002, 454-461; Yeh, R., et al., "Single Mask, Large Force, and Large Displacement Electrostatic Linear Inchworm Motors," J. Microelectromechanical Sys., 11:4, August 2002, 330-336; and Loh, N. C., al., "Sub-10 cm3 Interferometric Accelerometer with Nano-g Resolution," J. Microelectromechanical Sys., 11:3, June 2002, 182-187; all of the above of which are incorporated by reference in their entirety.

Intelligent Implants

The present disclosure provides intelligent implants, e.g., an implantable medical device with an implantable reporting processor (IRP). When the intelligent implant is included in a component of an implant system that replaces a joint, the intelligent implant can monitor displacement or movement of the component or implant system. The intelligent implant can also provide kinematic data that can be used to assess the mobility and health of the patient in which the system is implanted.

With reference to FIGS. 2A, 2B, 3A, 3B, 3C, 4A, and 4B an intelligent implant 100, 300, 400 may be part of a knee implant system. In these embodiments, the intelligent implant 100, 300, 400 corresponds to a tibial component of a knee replacement system for a TKA and includes a tibial plate 106, 306, 406 and an implantable reporting processor (IRP) 104, 304, 404. The tibial plate 106, 306, 406 is configured to physically attach to an upper surface of a tibia 108. A tibial stem 110, 310, 410 or tibial keel extends from the tibial plate 106, 306, 406. The tibial stem 110, 310, 410 includes a receptacle 112, 312, 412 configured to receive a portion of the implantable reporting processor 104, 304, 404.

Figure 2B:
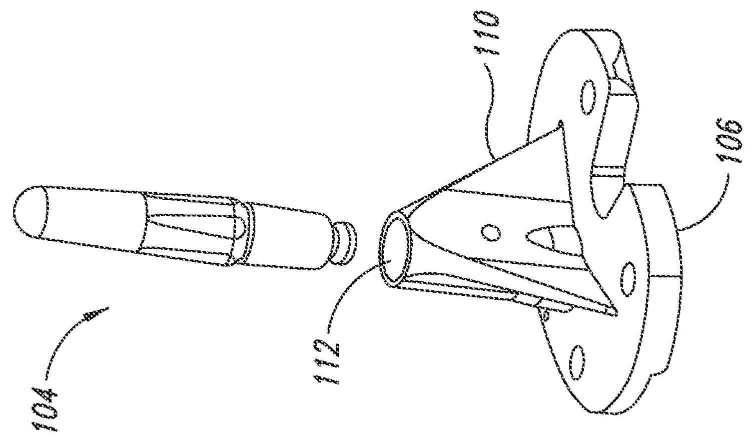
FIGS. 2A and 2B are illustrations of an intelligent implant in the form of a tibial component of a knee prosthesis including a tibial plate and a long-extension implantable reporting processor extending from a tibial stem.
Figure 2A:
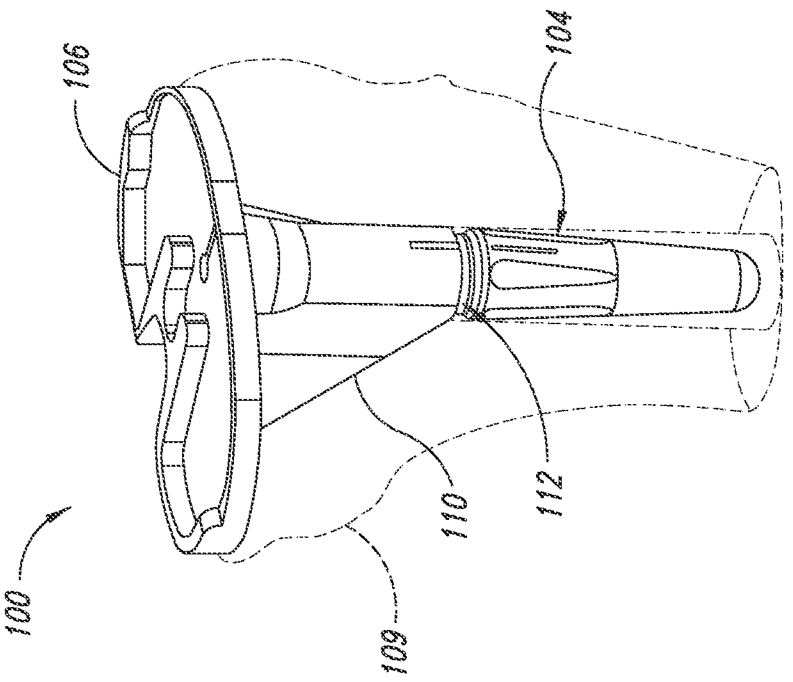

In the embodiment of FIGS. 2A and 2B, the tibial plate 106 is adhered or glued to the upper surface of the tibia using a biocompatible cement to establish a physical attachment between the tibial component 100 and the tibia. In the embodiments of FIGS. 3A, 3B, 3C, 4A, and 4B, a portion of the tibial plate 306, 406 is configured to adhere to the upper surface of the tibia in the absence of cement. To this end, the portion of the tibial plate 306, 406 may be the lower surface facing the tibia and may include a layer of porous ingrowth material into which boney tissue grows to secure the tibial plate in place. The porous layer may be formed for example, by cobalt-chromium sintered beads, titanium fiber metal mesh, cancellous-structured titanium, and titanium plasma spray. A number of projections 305, 405 or pegs may extend from the lower surface. These projections 305, 405 are configured to be forced into the upper surface of the tibia and establish an initial fixation or physical attachment between the tibial component 300, 400 and the tibia. The embodiments of FIGS. 3A, 3B, 4A, and 4B are referred to as cementless tibial components. Patient selection for cementless tibial components tend to be younger patients with healthier bone (not osteoporotic). The fundamental concept for cementless tibial component design is to provide "wings" for rotational stability but minimize the amount of bone that is being removed, hence the tibial stem of these components tend to be narrow. Minimal bone removal is one of the preferred aspects of cementless. Cemented tibias require more bone removal to create a cement mantel around the implant.

In the embodiment of FIGS. 2A, 2B, 3A, 3B, and 3C, the implantable reporting processor 104, 304 is a component assembly manufactured separate from the tibial plate 106, 306 and is mechanically coupled to the tibial stem 110, 310 of the tibial plate to form the tibial component 100, 300. To this end, a portion of the implantable reporting processor 104, 304 is inserted into the receptacle 112, 312 of the tibial stem 110, 310 and fixed in place therein by application of a force that couples respective mechanical features of the implantable reporting processor and the tibial plate 106, 306. In the embodiments of FIGS. 4A and 4B, the implantable reporting processor 404 is integrated into the tibial stem 410 of the tibial plate 406 during assembly. To this end, a subassembly 409 of the implantable reporting processor 104 is inserted into the receptacle 412 of the tibial stem 410 and a cover 411 of the implantable reporting processor is coupled to the subassembly 409 and the tibial stem. The subassembly 409 includes a battery 413, an electronics assembly 415, an antenna feedthrough 417, and an antenna 419.

In other embodiments, the intelligent implant corresponds to a femoral component of a knee implant system. The femoral component may be of the type shown in FIG. 1A that is used for a TKA. The femoral component may be a unicompartmental femoral component (not shown) used in partial knee arthroplasty (PKA). In either case, an implantable reporting processor may be configured to physically attach to an extension of the femoral component.

Figure 5A:
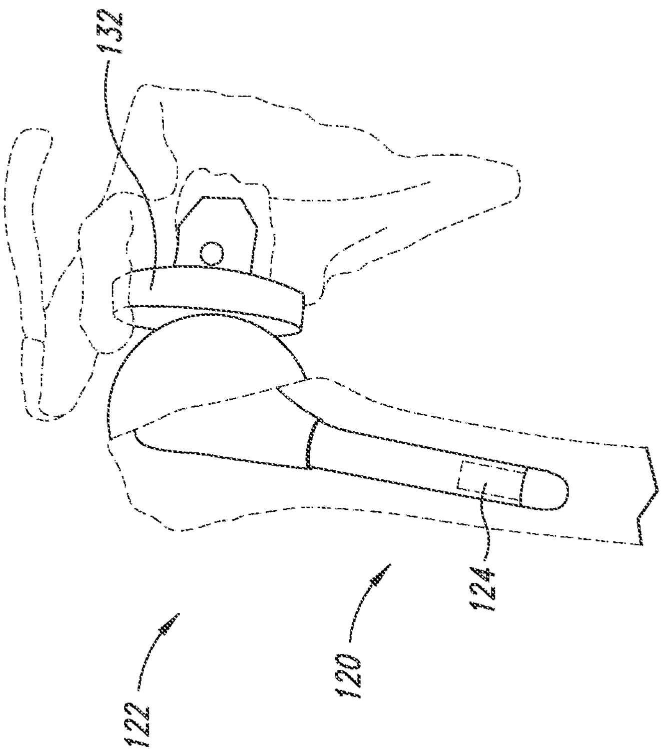
FIGS. 5A and 5B are illustrations of an intelligent implant in the form of a humeral component of a shoulder prosthesis including an implantable reporting processor integrated with a humeral stem.
Figure 5B:
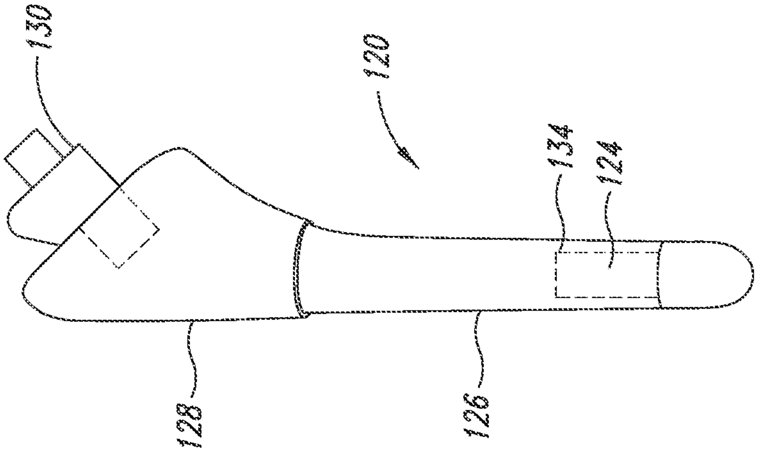

With reference to FIGS. 5A and 5B, an intelligent implant 120 may be part of a shoulder implant system 122. In this embodiment, the intelligent implant 120 corresponds to a humeral component of a shoulder replacement system for a TSA and includes an implantable reporting processor (IRP) 124. The humeral component 120 includes a humeral stem 126, a humeral body 128, and a humeral head adapter 130. The humeral head adapter 130 is configured to physically attach to glenoid cap 132. The humeral stem 126 includes a receptacle 134 configured to receive the implantable reporting processor 124.

Figure 6B:
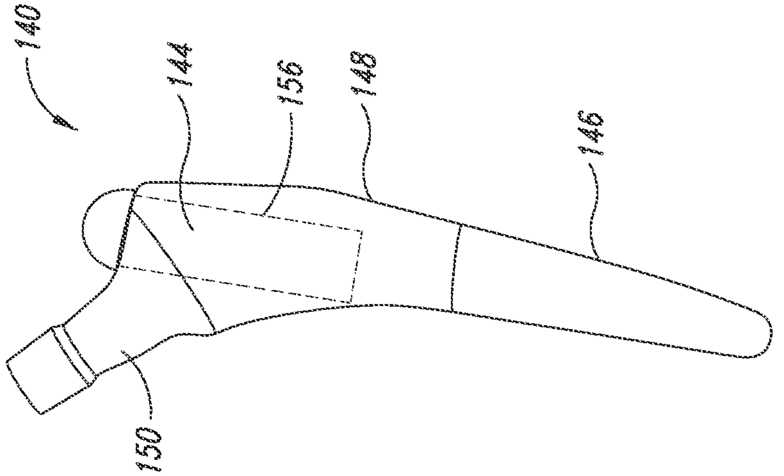
FIGS. 6A and 6B are illustration of an intelligent implant in the form of a femoral component of a hip prosthesis including an implantable reporting processor integrated with a femoral stem.
Figure 6A:
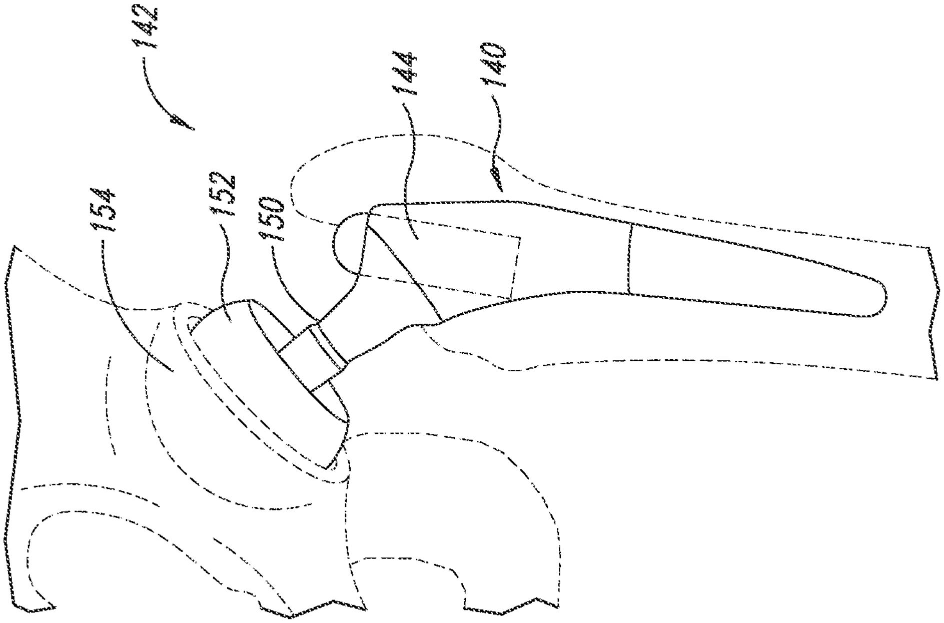

With reference to FIGS. 6A and 6B, an intelligent implant 140 may be part of a hip implant system 142. In this embodiment, the intelligent implant 140 corresponds to a femoral component of a hip replacement system for a THA and includes an implantable reporting processor (IRP) 144. The femoral component 140 includes a femoral stem 146, a femoral body 148, and a femoral neck 150. The femoral neck 150 is configured to physically attach to a femoral head 152 that is configured to attached to an acetabular cap 154. The femoral body 148 includes a receptacle 156 configured to receive the implantable reporting processor 144.

Implantable Reporting Processors

The present disclosure provides implantable reporting processors (IRP) for implant systems that replace a joint. Embodiments disclosed include IRPs for knee implant systems, IRPs for shoulder implant systems, and IRPs for hip implant systems. As previously mentioned, in some embodiments the IRP is a component assembly that is manufactured independent of other components of the implant system and later assembled together with a component of an implant system. In some embodiments, the IRP is integrated with a component of the implant system during manufacture of the component.

Component-Assembly Implantable Reporting Processors

Figure 7B:
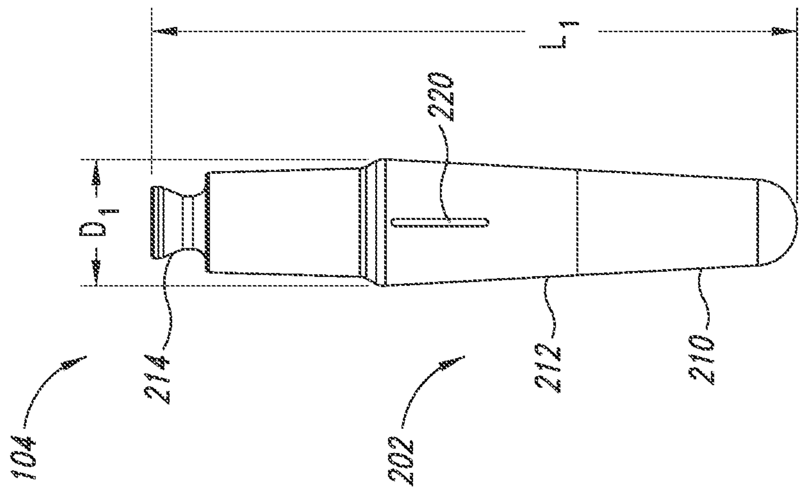
FIGS. 7A and 7B are illustrations of the long-extension implantable reporting processor of the tibial component of FIGS. 2A and 2B.
Figure 7A:
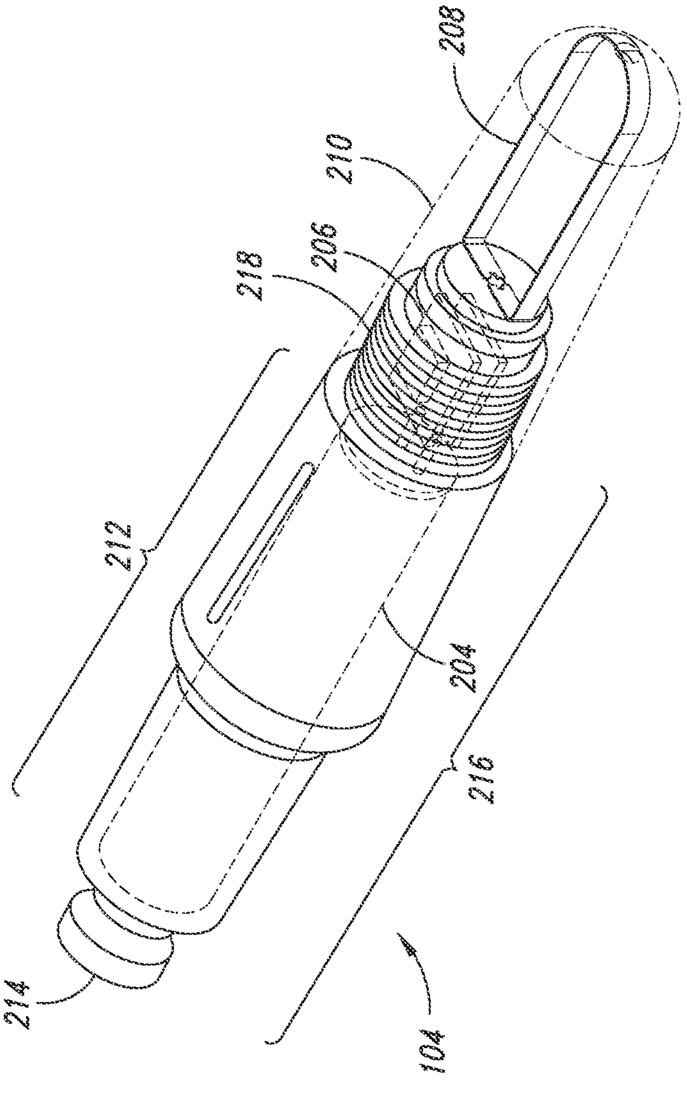

With reference to FIGS. 7A and 7B, an implantable reporting processor 104 for an intelligent implant 100 corresponding to a tibial component like that shown in FIG. 2A is configured to function as a long tibial stem extension. This long-extension implantable reporting processor 104 includes a housing that encloses a battery 204, an electronics assembly 206, and an antenna 208. The housing 202 of the implantable reporting processor 104 includes a cover 210 or radome and a casing 216 or extension. The casing 216 includes a central section 212, an upper coupling section 214, and a lower coupling section 218 with which the cover 210 is configured to couple.

The housing 202 has a length $L_1$ of about 73 millimeters (mm), and has a diameter $D_1$ of about 14 mm at its widest cross section. In various embodiments, an implantable reporting processor 104 may have a length $L_1$ in a range of 70 mm and 100 mm. In various embodiments, an implantable reporting processor 104 may have a diameter $D_1$ at its widest cross-section in a range of 5 mm and 30 mm. It should be noted that the term diameter is used in a broad sense to refer to a maximum cross-sectional distance, where that cross-section need not be an exact circle, but may be other shapes such as oval, elliptical, or even 4-, 5- or 6-sided.

The cover 210 covers and protects the antenna 208, which allows the implantable reporting processor 104 to receive and transmit data/information (hereinafter "information"). The cover 210 can be made from any material, such as plastic or ceramic, which allows radio-frequency (RF) signals to propagate through the cover with acceptable levels of attenuation and other signal degradation. In some embodiments the cover 210 is comprised of polyetherether-ketone (PEEK).

Figure 1B:
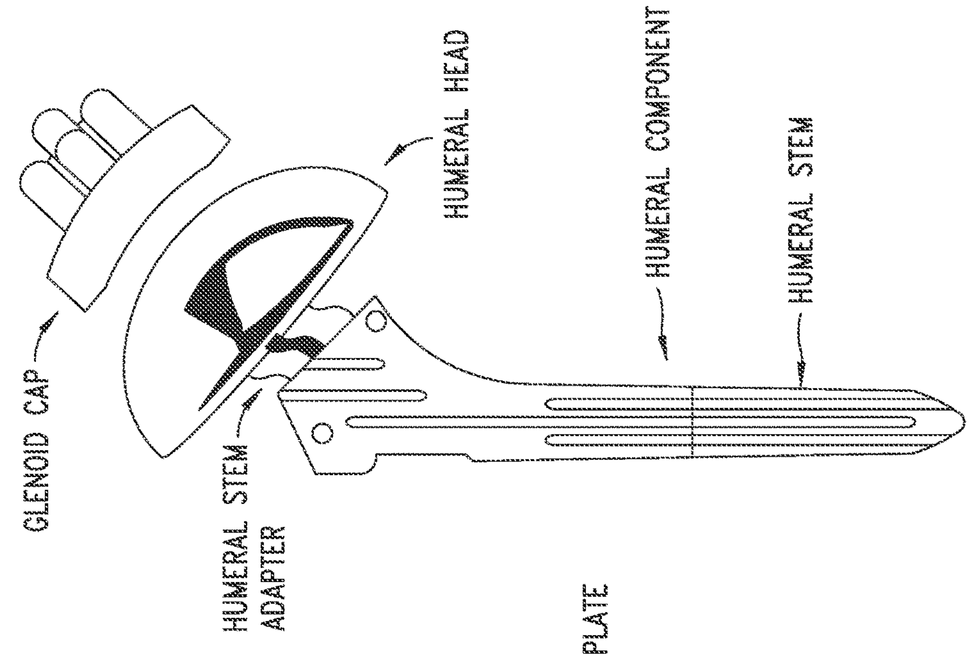
FIG. 1B (Prior Art)
FIG. 1B is an illustration of a conventional implantable medical device in the form of a shoulder prosthetic system, or total shoulder implant (TSI).
Figure 1C:
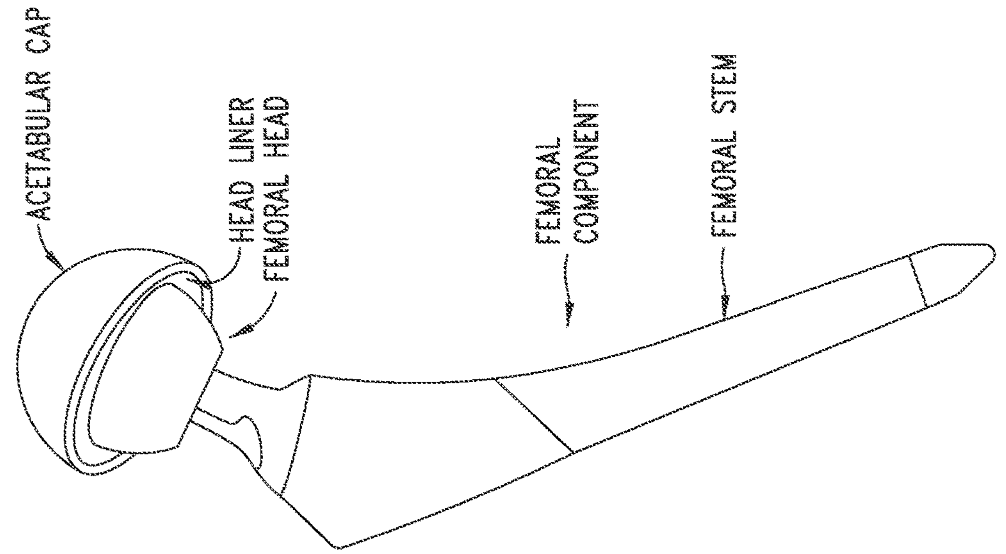
FIG. 1C (Prior Art)
FIG. 1C is an illustration of a conventional implantable medical device in the form of a hip prosthetic system, or total hip implant (THI).

The central section 212 and the upper coupling section 214, which are integral with one another, cover and protect the electronics assembly 206 and the battery 204, and can be made from any suitable material, such as metal, plastic, or ceramic. Furthermore, the central section 212 includes an alignment mark 220, which is configured to align with a corresponding alignment mark on the outside of the receptacle 112 of the tibial component shown in FIGS. 1A and 1B. Aligning the alignment mark 220 with the mark on the receptacle 112 when the tibial component of the knee implant is implanted ensures that the implantable reporting processor 104 is in a desired orientation relative to the tibial stem 110.

The upper coupling section 214 is sized and otherwise configured to fit into the receptacle 112 of the tibial stem 110. The fit may be snug enough so that no securing mechanism (e.g., adhesive, set-screw) is needed, or the upper coupling section 214 can include a securing mechanism, such as threads, clips, and/or a set-screw (not shown) and a set-screw engagement hole, for attaching and securing the implantable reporting processor 104 to the tibial stem 110.

With reference to FIGS. 8A, 8B, 8C, and 9, the primary components of the implantable reporting processor 104 include the battery 204, the electronics assembly 206, and the antenna 208. The battery 204 is configured to power the electronic circuitry of the implantable reporting processor 104 over a significant portion (e.g., 1-15+ years, e.g., 10 years, or 15 years), or the entirety (e.g., 18+ years), of the anticipated lifetime of the implantable reporting processor.

In some embodiments, the battery 204 has a lithium-carbon-monofluoride (LiCFx) chemistry, a cylindrical housing or cylindrical container 506, a cathode terminal 502, and an anode terminal 504, which is a plate that surrounds the cathode terminal. LiCFx is a non-rechargeable (primary) chemistry, which is advantageous for maximizing the battery-energy storage capacity. The cathode terminal 502 makes conductive contact with an internal cathode electrode and couples to the cylindrical container using a hermetic feed-through insulating material of glass or ceramic. The use of the hermetic feed through prevents leakage of internal battery materials or reactive products to the exterior battery surface. Furthermore, the glass or ceramic feed-through material electrically insulates the cathode terminal 502 from the cylindrical container 506, which makes conductive contact with the internal anode electrode. The anode terminal 504 is welded to the cylindrical container 506. By locating the cathode terminal 502 and the anode terminal 504 on the same end of the battery 204, both terminals can be coupled to the electronics assembly 206 without having to run a lead, or other conductor, to the opposite end of the battery.

The container 506 can be formed from any suitable material, such as titanium or stainless steel, and can have any configuration suitable to limit expansion of the battery 204 as the battery heats during use. Because the battery 204 is inside of the casing 216, if the battery were to expand too much, it could crack the container 506 or the casing 216, or irritate the subject's tibia or other bodily tissue.

With its LiCFx chemistry, the battery 204 can provide, over its lifetime, about 360 milliampere-hours (mAh) at 3.7 volts (V), although one can increase this output by about 36 mAh for each 5 mm of length added to the battery (similarly, one can decrease this output by about 36 mAh for each 5 mm of length subtracted from the battery). It is understood that other battery chemistries can be used if they can achieve the appropriate power requirements for a given application subject to the size and longevity requirements of the application. Some additional potential battery chemistries include, but are not limited to, Lithium ion (Li-ion), Lithium Manganese dioxide (Li—$MnO_2$), silver vanadium oxide (SVO), Lithium Thionyl Chloride (Li—$SOCl_2$), Lithium iodine, and hybrid types consisting of combinations of the above chemistries such as CFx-SVO.

The electronics assembly 206 includes a circuit assembly 207 that has one or more sensors and a processor configured to receive and process information from the sensors relating to the state and functioning of the implantable reporting processor 104 and the state of the patient within which the implantable reporting processor is implanted. The electronics assembly 206 is further configured to transmit the processed information to an external device through the antenna 208.

Figure 9:
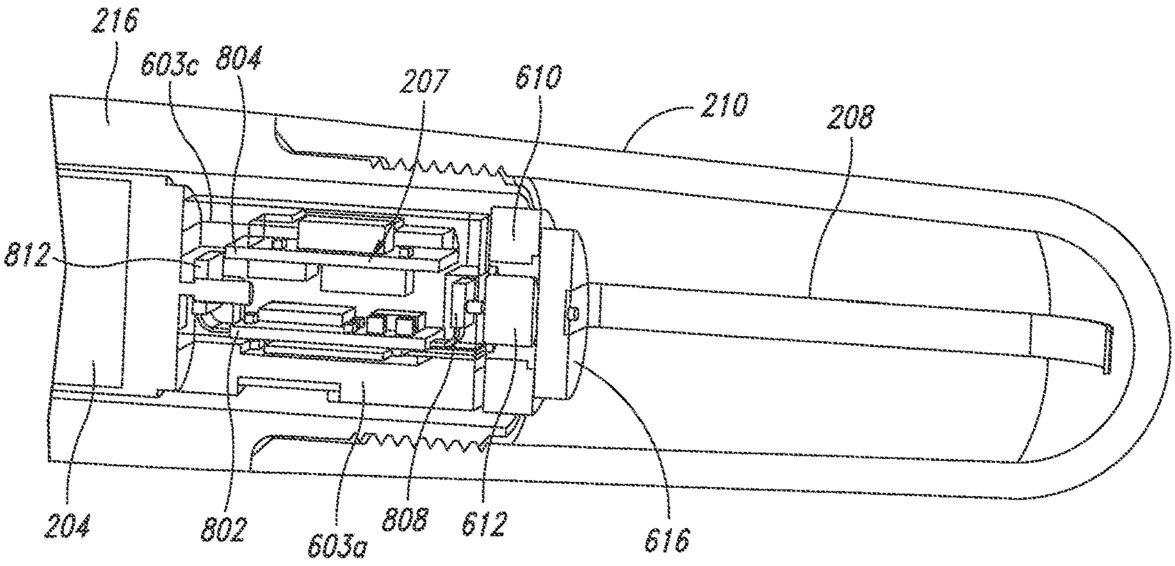
FIG. 9 is a cross-section, perspective illustration of an end region of the implantable reporting processor of FIG. 7A showing an electronics assembly and an antenna.
Figure 10A:
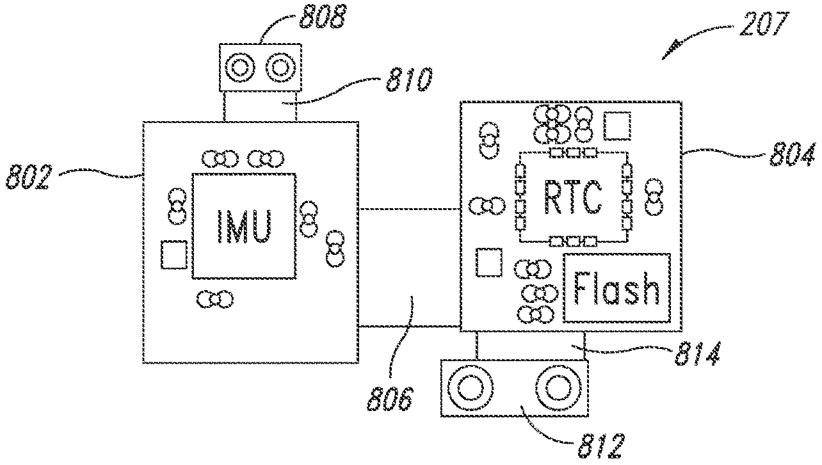
FIGS. 10A and 10B are illustrations of the electronics assembly of FIGS. 8C and 9.
Figure 10B:
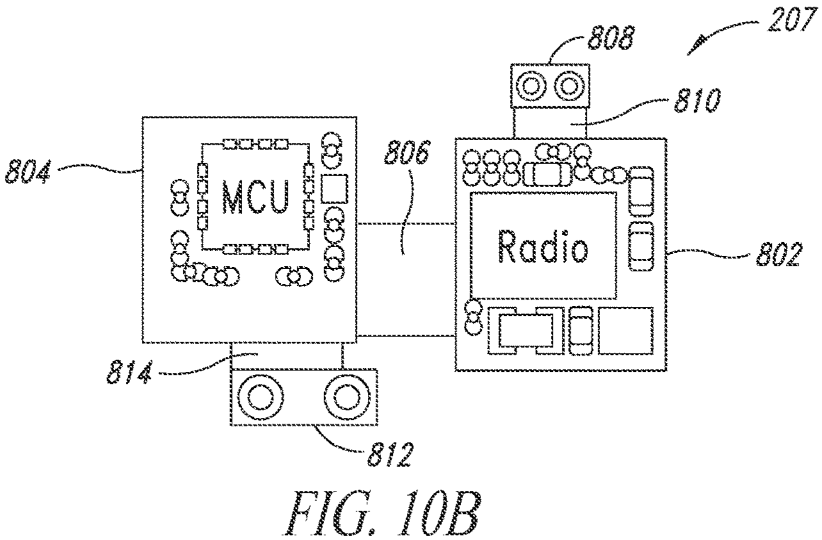

With reference to FIGS. 10A and 10B, the circuit assembly 207 includes a first printed circuit board (PCB) 802 and a second PCB 804, each having various electronics components mounted thereon. The two PCBs 802, 804 are connected to each other by a flex wire 806. The circuit assembly 207 also includes an antenna terminal board 808 that is connected to the first PCB 802 by a flex wire 810, and a battery terminal board 812 that is connected to the second PCB 804 by a flex wire 814. The flex wires 806, 810, 814 allows the circuit assembly 207 to be folded so that the two PCBs 802, 804 are generally parallel to each other, and the two terminal boards 808, 812 are generally parallel to each other to form an open box structure, as shown in FIGS. 8C and 9.

The circuit assembly 207 is coupled physically and electrically to the antenna 208 through terminals on the antenna terminal board 808, and to the power component (e.g., battery) through terminals on the battery terminal board 812. The PCBs 802, 804 may include an Inertial Measurement Unit (IMU) integrated circuit, a Real-Time Clock (RTC) integrated circuit, a memory integrated circuit (Flash), and other circuit components on one side, and a microcontroller (MCU) integrated circuit, a radio transmitter (Radio) integrated circuit, and other circuit components on the other side. In any event, the folded circuit assembly 207 provides a compact configuration that conserves a significant amount of physical space in the implantable reporting processor.

Figure 8B:
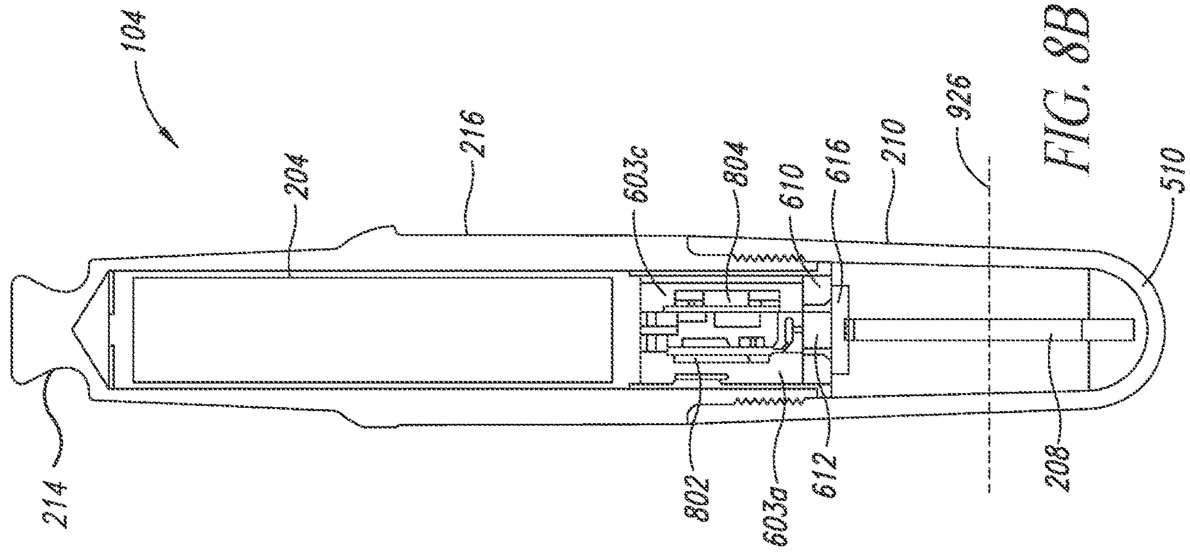
FIGS. 8A and 8B are cross-section illustrations of the implantable reporting processor of FIG. 7A.
Figure 8A:
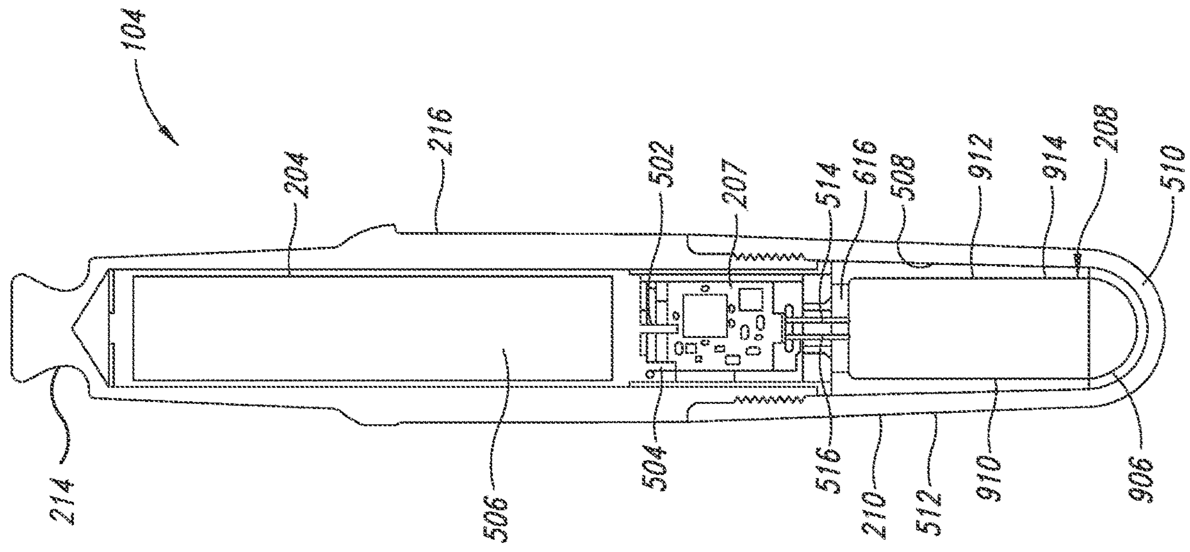
Figure 8C:
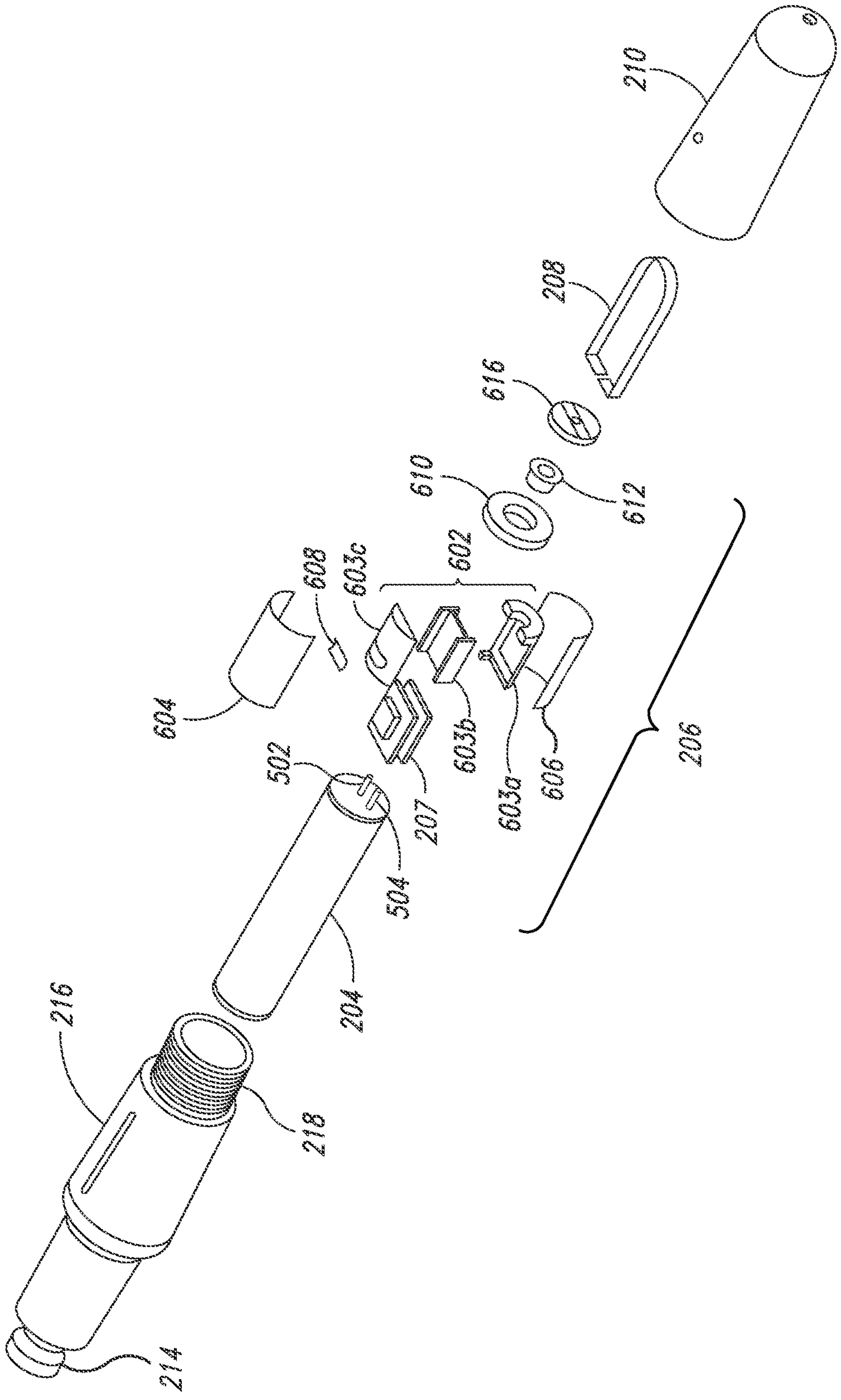
FIG. 8C is an exploded illustration of the implantable reporting processor of FIG. 7A.

With reference to FIG. 8C, other components of the electronics assembly 206 include a liner 602, an upper shroud 604, a lower shroud 606, an x-ray ID 608, a flange 610, an implant-grade bipolar feedthrough 612, and an antenna spacer 616. The liner 602 functions to mechanically stabilize the circuit assembly 207 within the housing of the implantable reporting processor 104, and includes three components 603*a*, 603*b*, 603*c* that are formed from any suitable material, including for example, polycarbonate. The upper shroud 604 and the lower shroud 606 are formed of a biocompatible metallic material. In some embodiments, the material is titanium. The flange 610 is formed of a biocompatible metallic material. In some embodiments, the material is titanium. The antenna spacer 616 is formed of a non-conductive biocompatible material. In some embodiments, the antenna spacer 616 is formed of a PEEK. The feedthrough 612 is formed of a non-conductive biocompatible material. In some embodiments, the feedthrough 612 is formed of a ceramic. The x-ray ID 608 for purposes of providing identification of the implantable reporting processor 104 independent of wireless communication.

Figure 11A:
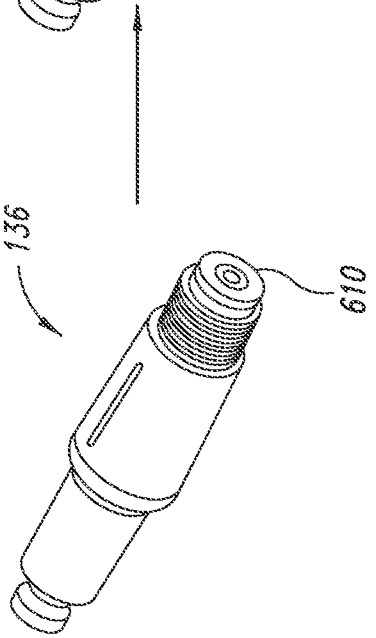
FIGS. 11A, 11B, and 11C are a series of illustrations depicting an assembling of the implantable reporting processor of FIG. 7A.
Figure 11B:
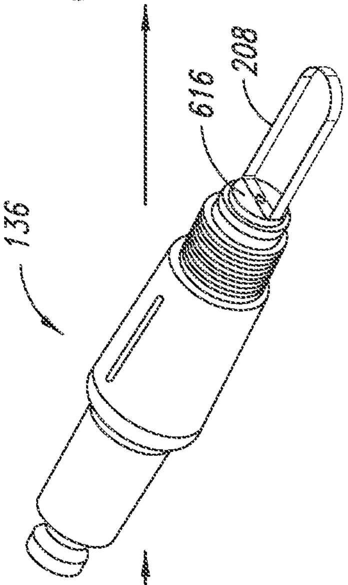
Figure 11C:
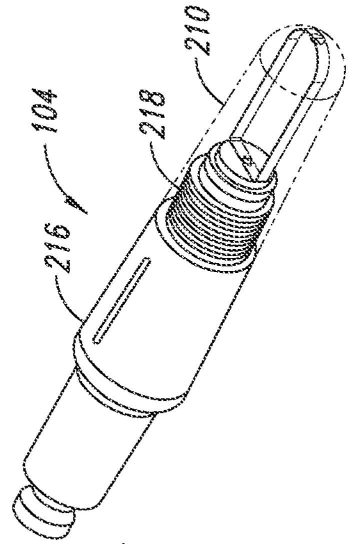

With reference to FIGS. 11A-11C, an implantable reporting processor 104 of FIG. 8C is assembled from a pre-assembled hermetic assembly 136, an antenna 208, and a cover 210. With reference to FIGS. 11B and 11C, an antenna spacer 616 is placed over the external pins of the feedthrough 612 (shown in FIG. 8C) of the hermetic assembly 136, and an antenna 208 is welded to the feedthrough pins. A cover 210 is then assembled onto the lower coupling section 218 of the casing 216. In some embodiments, the cover is back-filled with an epoxy (fill and bleed ports not shown). The epoxy material encapsulates the antenna 208 within the cover 210. The epoxy material may be medical grade silicone. Encapsulating the antenna 208 increases structural rigidity of the implantable reporting processor 104, and isolates the antenna from tissue and body fluid.

Thus, disclosed is an implantable reporting processor 104 wherein all active electronics and the battery 204 are contained within a hermetic assembly 136. The ground reference potential of the battery 204 is physically welded to the lower shroud 606 and the casing 216. By virtue of the intimate contact between the casing 216 and the tibial plate 106 with surrounding tissue, the implantable reporting processor 104 ground reference potential is equal to the body tissue potential (electrically neutral with surrounding tissue). Within the hermetic assembly 136, both the battery 204 reference potential (GND) and the battery positive terminal potential (VBATT) are routed throughout the electronics assembly 206 to power the electronic components. The feedthrough 612 provides connections between the electronics inside the hermetic assembly 136 and the loop antenna 208 outside the hermetic assembly. The antenna 208 is a conductive loop formed of platinum-iridium (PtIr=90/10) ribbon with one end connected to the radio transceiver and the other end connected to the battery reference potential (GND). The loop antenna 208 provides a magnetic loop, e.g., AC signal in a conductive loop generates magnetic field. The antenna 208 is encapsulated by the cover 210 and epoxy backfill, both of which are electrically non-conductive. The antenna 208 is the only electrically active component of the implantable reporting processor 104 outside the hermetic assembly 136 and under normal operating conditions is insulated by the epoxy backfill and PEEK cover from interacting electrically with surrounding tissue.

Figure 3C:
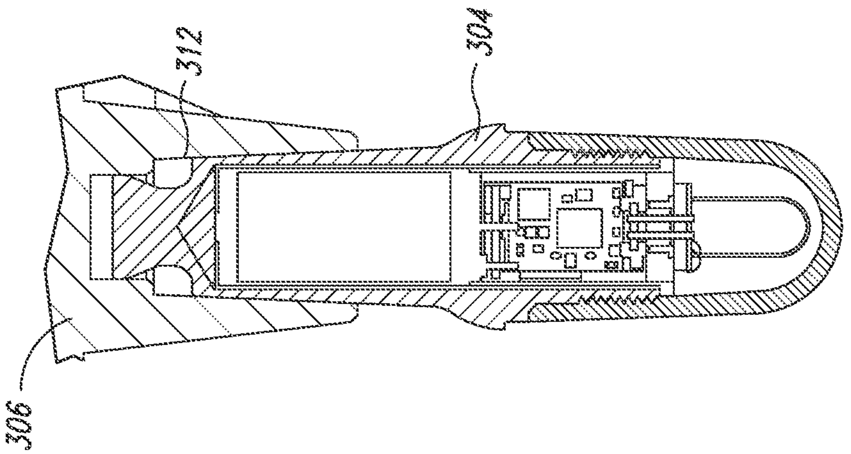
FIGS. 3A, 3B, and 3C are illustrations of an intelligent implant in the form of a tibial component of a knee prosthesis including a tibial plate and a short-extension implantable reporting processor extending from a tibial stem.
Figure 3B:
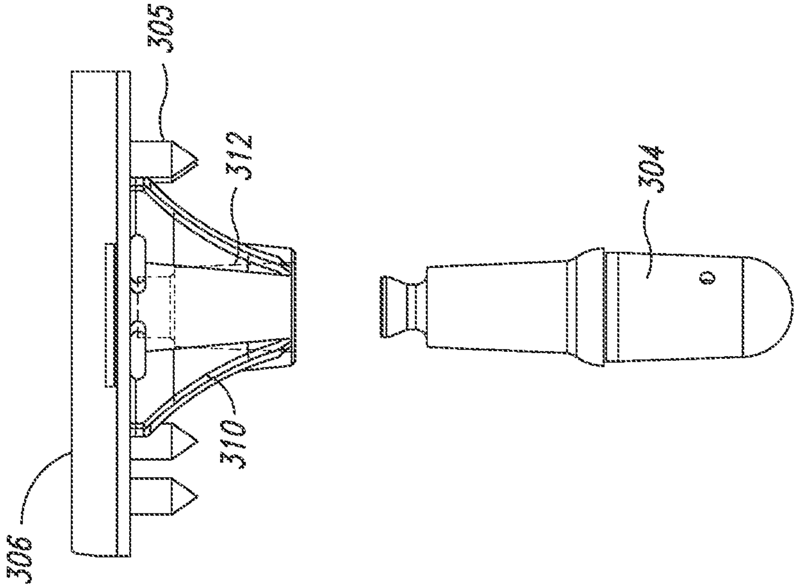
Figure 3A:
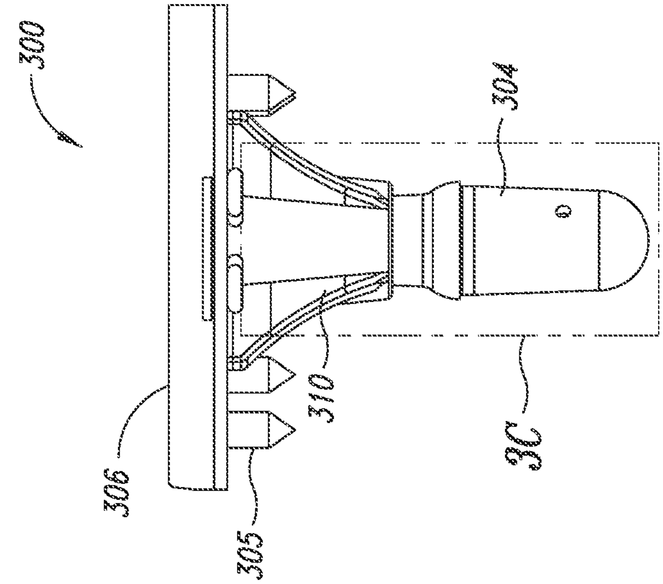
Figure 4B:
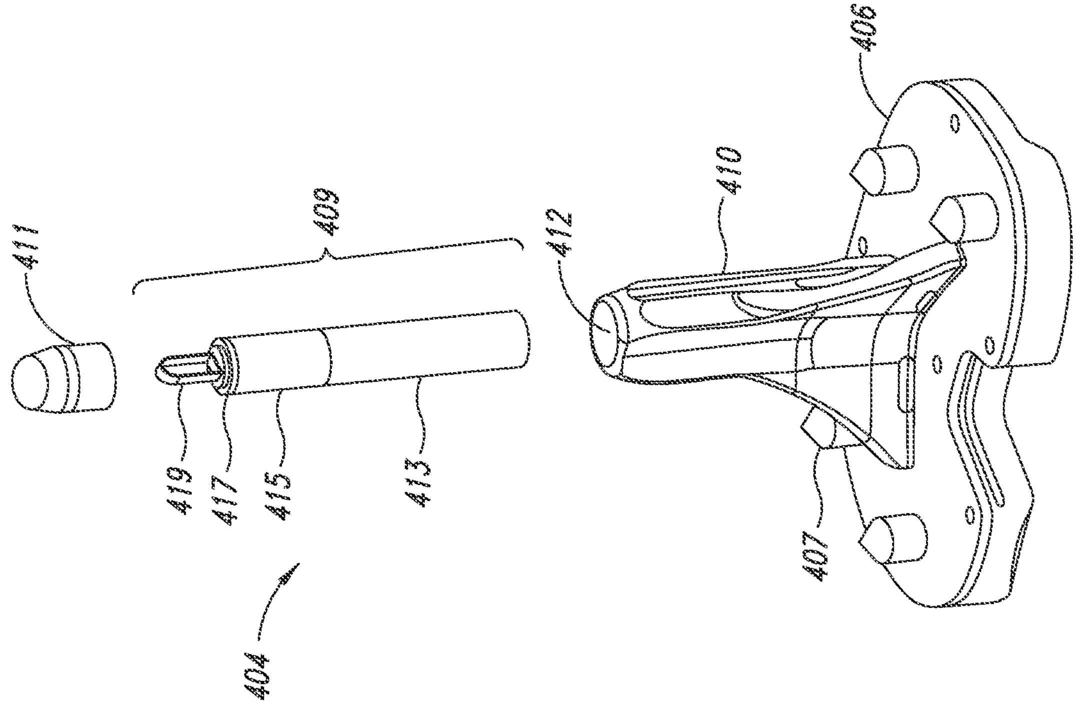
FIGS. 4A and 4B are illustrations of an intelligent implant in the form of a tibial component of a knee prosthesis including a tibial plate and an implantable reporting processor integrated with a tibial stem.
Figure 4A:
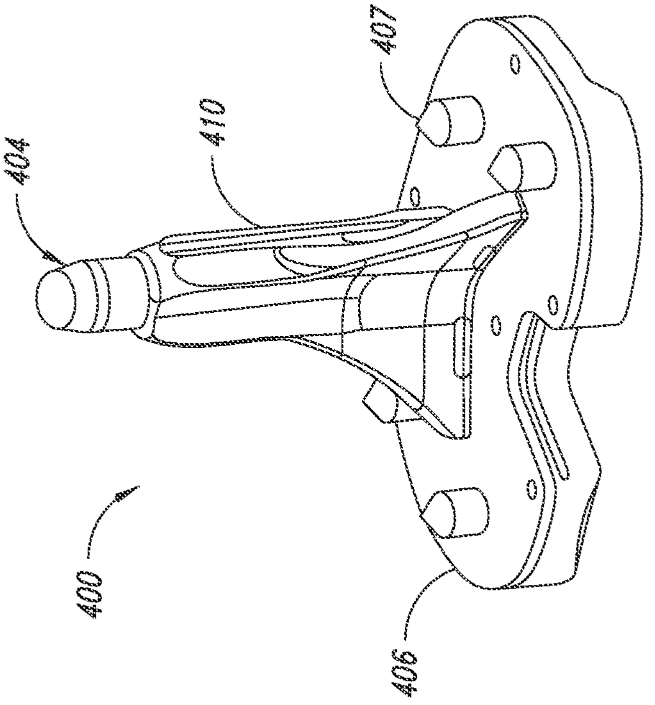
Figure 12A:
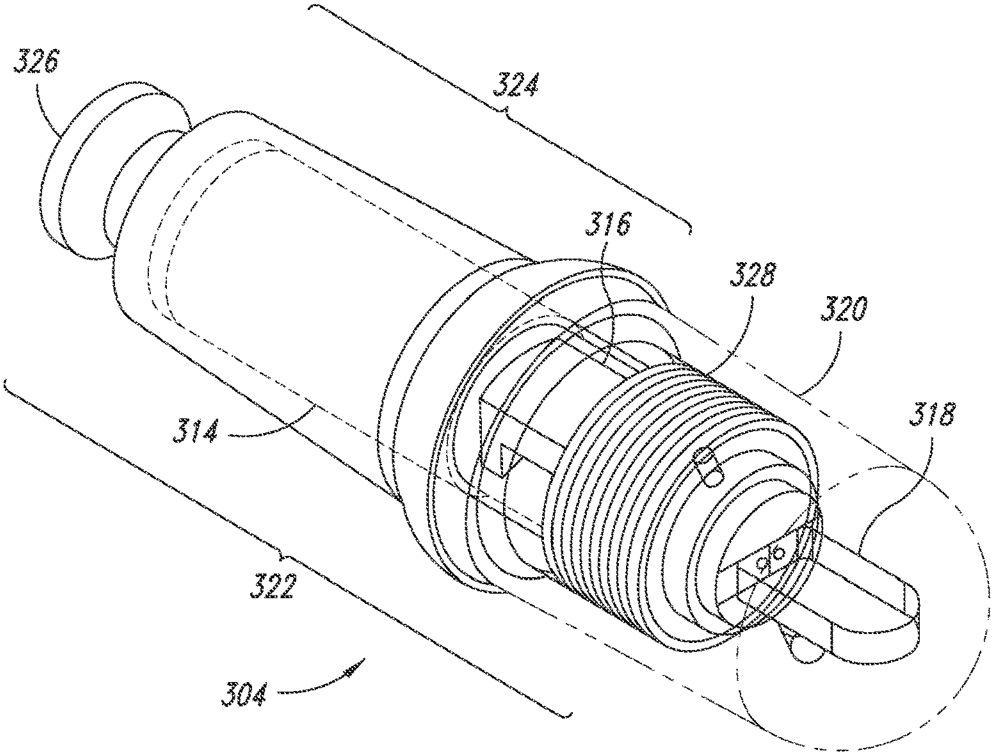
FIGS. 12A and 12B are illustrations of the short-extension implantable reporting processor of the tibial component of FIGS. 3A and 3B.
Figure 12B:
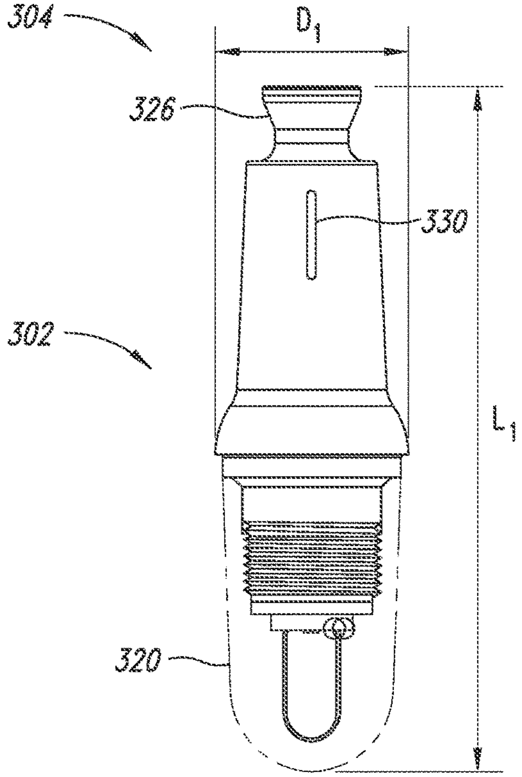

With reference to FIGS. 12A and 12B, an implantable reporting processor 304 for an intelligent implant 300 corresponding to a tibial component like that shown in FIG. 3A is configured to function as a short tibial stem extension. This short-extension implantable reporting processor 304 includes a housing that encloses a battery 314, an electronics assembly 316, and an antenna 318. The housing 302 of the implantable reporting processor 304 includes a cover 320 or radome and a casing 322. The casing 322 includes a central section 324, an upper coupling section 326, and a lower coupling section 328 with which the cover 320 is configured to couple.

The housing 302 has a length $L_1$ of about 28 millimeters (mm), and has a diameter $D_1$ of about 14 mm at its widest cross section. In various embodiments, an implantable reporting processor 104 may have a length $L_1$ in a range of 20 mm and 30 mm. In various embodiments, an implantable reporting processor 304 may have a diameter $D_1$ at its widest cross-section in a range of 5 mm and 30 mm. It should be noted that the term diameter is used in a broad sense to refer to a maximum cross-sectional distance, where that cross-section need not be an exact circle, but may be other shapes such as oval, elliptical, or even 4-, 5- or 6-sided.

The cover 320 covers and protects the antenna 318, which allows the implantable reporting processor 304 to receive and transmit data/information (hereinafter "information"). The cover 320 can be made from any material, such as plastic or ceramic, which allows radio-frequency (RF) signals to propagate through the cover with acceptable levels of attenuation and other signal degradation. In some embodiments the cover 210 is comprised of polyetherether-ketone (PEEK).

The central section 324 and the upper coupling section 326, which are integral with one another, cover and protect the electronics assembly 316 and the battery 314, and can be made from any suitable material, such as metal, plastic, or ceramic. Furthermore, the central section 324 includes an alignment mark 330, which is configured to align with a corresponding alignment mark on the outside of the receptacle 312 of the tibial component shown in FIGS. 3A and 3B. Aligning the alignment mark 330 with the mark on the receptacle 312 when the tibial component of the knee implant is implanted ensures that the implantable reporting processor 304 is in a desired orientation relative to the tibial stem 310.

The upper coupling section 326 is sized and otherwise configured to fit into the receptacle 312 of the tibial stem 310. The fit may be snug enough so that no securing mechanism (e.g., adhesive, set-screw) is needed, or the upper coupling section 326 can include a securing mechanism, such as threads, clips, and/or a set-screw (not shown) and a set-screw engagement hole, for attaching and securing the implantable reporting processor 304 to the tibial stem 310.

Figure 13B:
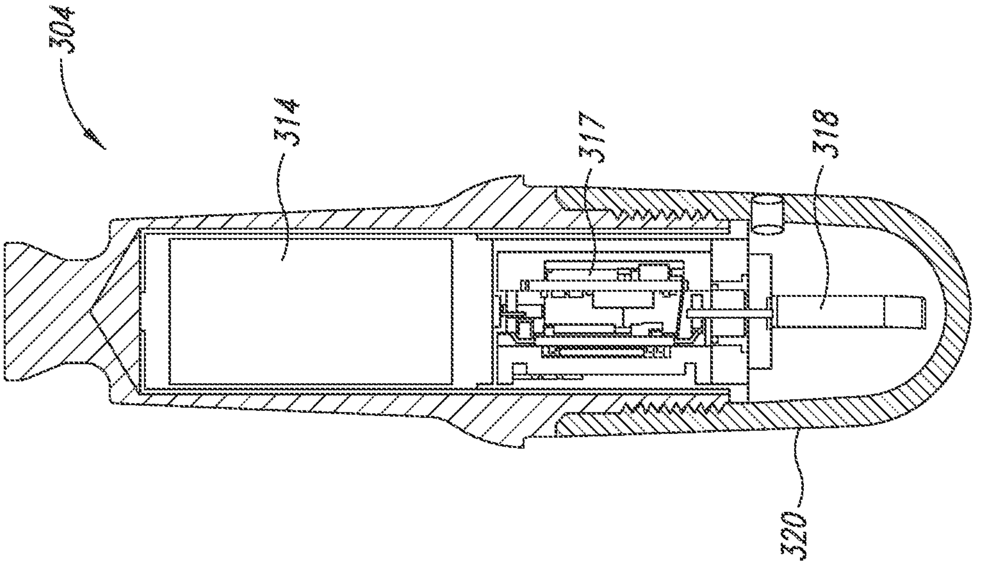
FIGS. 13A and 13B are cross-section illustrations of the implantable reporting processor of FIG. 12A.
Figure 13A:
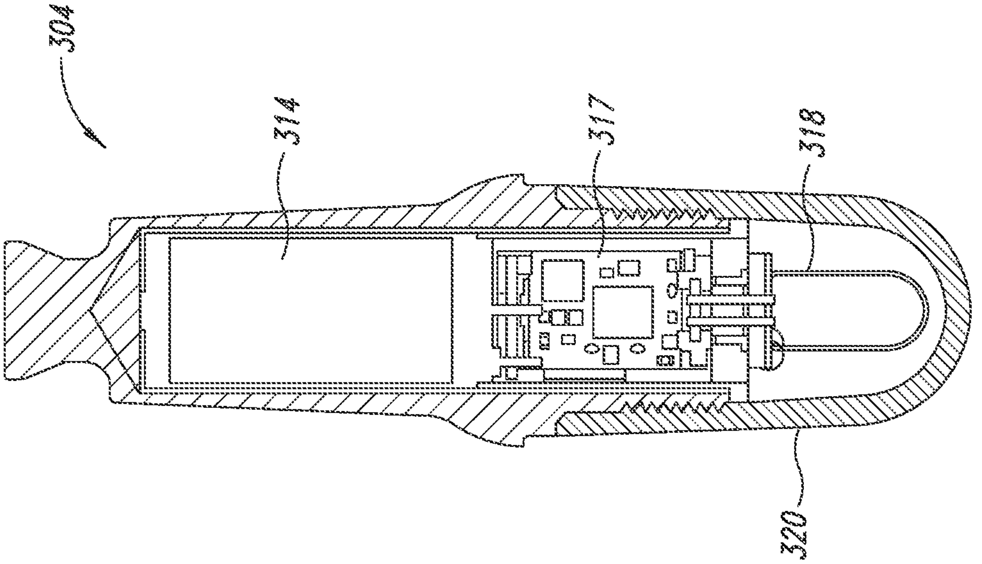
Figure 13C:
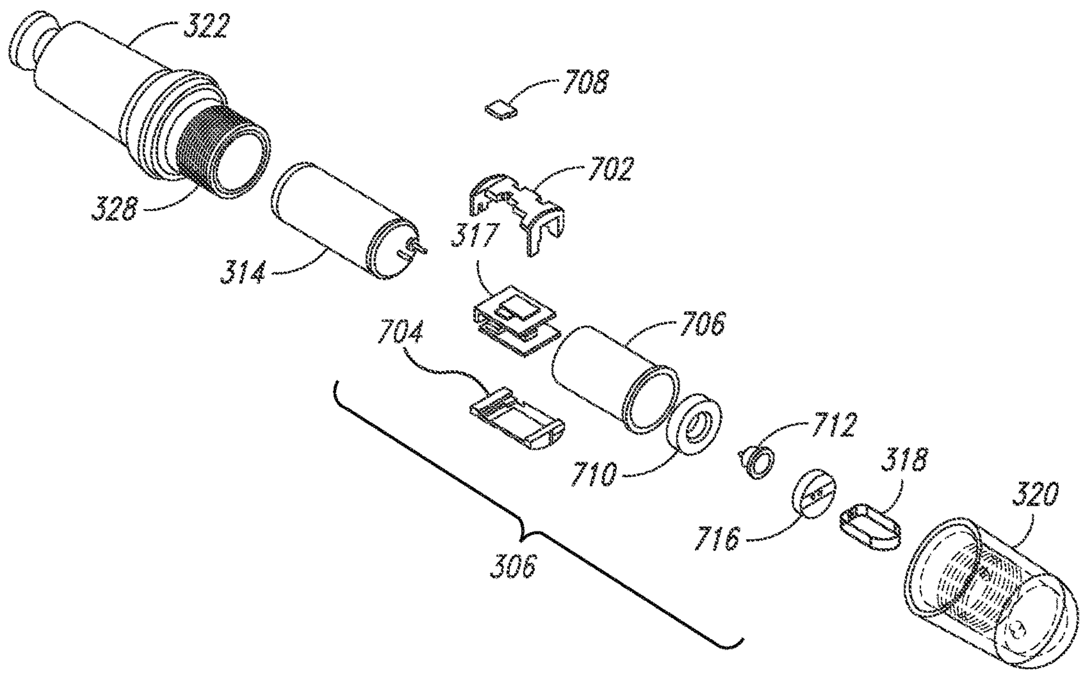
FIG. 13C is an exploded illustration of the implantable reporting processor of FIG. 12A.

With reference to FIGS. 13A, 13B, and 13C, the primary components of the implantable reporting processor 304 include the battery 314, the electronics assembly 316, and the antenna 318. The battery 314 is configured to power the electronic circuitry of the implantable reporting processor 304 over a significant portion (e.g., 1-15+ years, e.g., 10 years, or 15 years), or the entirety (e.g., 18+ years), of the anticipated lifetime of the implantable reporting processor. The battery 314 may be configured the same as described above with reference to FIGS. 8A, 8B, 8C. Accordingly, the details of the battery configuration are not repeated here.

The electronics assembly 316 includes a circuit assembly 317 that has one or more sensors and a processor configured to receive and process information from the sensors relating to the state and functioning of the implantable reporting processor 304 and the state of the patient within which the implantable reporting processor is implanted. The electronics assembly 316 is further configured to transmit the processed information to an external device through the antenna 318.

Figure 14A:
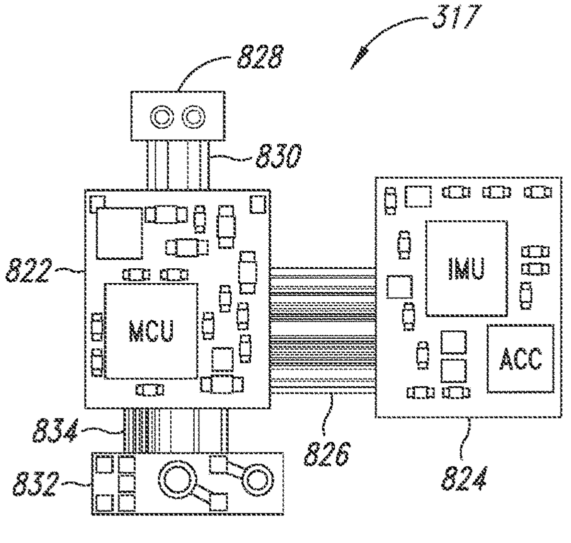
FIGS. 14A and 14B are illustrations of the electronics assembly of FIG. 13C.
Figure 14B:
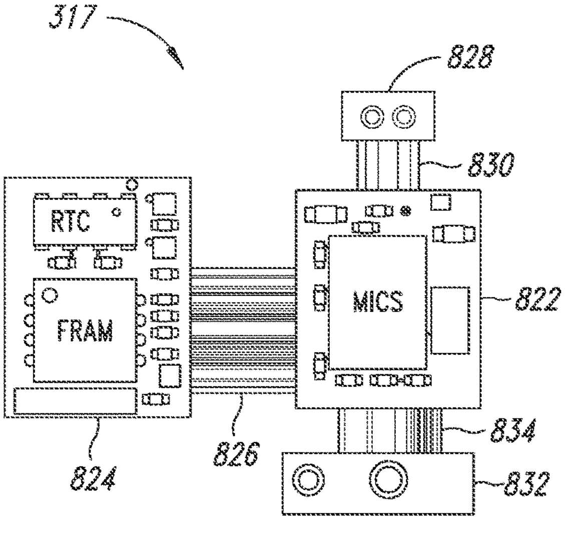

With reference to FIGS. 14A and 14B, the circuit assembly 317 is a rigid flex printed circuit board (PCB) assembly and includes a first PCB 822 and a second PCB 824. The first PCB 822 and the second PCB 824 are rigid PBCs and have various electronics components mounted thereon. The two rigid PCBs 822, 824 are connected by a flex section 826. The circuit assembly 317 also includes an antenna terminal board 828 that is connected to the first PCB 822 by a flex section 830, and a battery terminal board 832 that is connected to the second PCB 824 by a flex section 834. The flex sections 826, 830, 834, which may be polyamide sections, allow the circuit assembly 317 to be folded so that the two PCBs 822, 824 are generally parallel to each other, and the two terminal boards 828, 832 are generally parallel to each other to form an open box structure, as shown in FIG. 13C.

The circuit assembly 317 is coupled physically and electrically to the antenna 318 through terminals on the antenna terminal board 828, and to the power component (e.g., battery) through terminals on the battery terminal board 832. The PCBs 822, 824 may include an Inertial Measurement Unit (IMU) integrated circuit, an accelerometer (ACC), a microcontroller (MCU) integrated circuit and other circuit components on one side, and a Real-Time Clock (RTC) integrated circuit, a memory integrated circuit (FRAM), a radio transmitter (MICS) integrated circuit, and other circuit components on the other side. In any event, the folded circuit assembly 317 provides a compact configuration that conserves a significant amount of physical space in the implantable reporting processor.

With reference to FIG. 13C, other components of the electronics assembly 316 include a first liner 702, a second liner 704, a sleeve 706, an x-ray ID 708, a flange 710, an implant-grade bipolar feedthrough 712, and an antenna spacer 716. The first liner 702 and second liner 704 function to mechanically stabilize the circuit assembly 317 and its associated sensors, e.g., accelerometers and gyroscopes, within the sleeve 706 and within the casing 322 of the implantable reporting processor 304. The first liner 702 and second liner 704 also function to insulate the circuit assembly 317 from outside forces (e.g., shock or vibration). The stabilization and shock absorption functions of the circuit assembly 317 and its sensors serves to minimize mechanical movement or shifting of the sensors within the implantable reporting processor 304 and to maintain the orientation of the sensor within an acceptable degree of offset relative to the axes with which the sensor is aligned and about or along which the sensor measures. During manufacture of an implantable reporting processor 304 the sensors are aligned with an axis (e.g., black line marker on casing 322) and any residual measurements (e.g., non-zero measurement when zero measurement is expected) made by the sensor are accounted for through a calibration. The liner 702, 704 keeps the sensors relatively stable within a degree of tolerance to the alignment axis. For gyroscopes, the liners 702, 704 are configured to maintain residual offset to less than 10 or 3 degrees per second prior to calibration, and to less than 0.1 or 0.5 degrees per second degrees after calibration. For accelerometers, the liners 702, 704 are configured to maintain residual offset to less than 0.1 g or 0.15 g prior to calibration, and to less than 0.02 g or 0.01 g after calibration. Note that the preceding degrees per second and g values are electrical parameters output respectively by a gyroscope and accelerometer that translate from a mechanical misalignment of the sensors that the liners 702, 704 function to minimize.

The first liner 702 and a second liner 704 can be formed from any suitable material, including for example, polycarbonate. The sleeve 706 can be formed of a biocompatible metallic material. In some embodiments, the material is titanium. The flange 710 is formed of a biocompatible metallic material. In some embodiments, the material is titanium. The antenna spacer 716 is formed of a non-conductive biocompatible material. In some embodiments, the antenna spacer 716 is formed of a PEEK. The feedthrough 712 is formed of a non-conductive biocompatible material. In some embodiments, the feedthrough 712 is formed of a ceramic. The x-ray ID 708 for purposes of providing identification of the implantable reporting processor 304 independent of wireless communication.

An implantable reporting processor 304 of FIG. 13C can be assembled in the same way disclosed above with reference to FIGS. 11A-11C.

Integrated Implantable Reporting Processors

Figure 15:
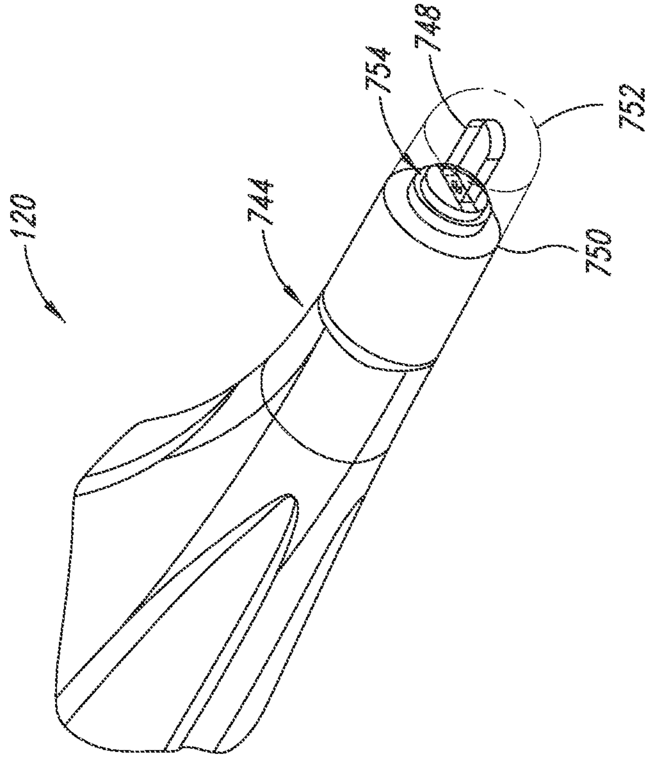
FIG. 15 is an illustration of the intelligent implant (humeral component with integrated implantable reporting processor) of FIGS. 5A and 5B.
Figure 16B:
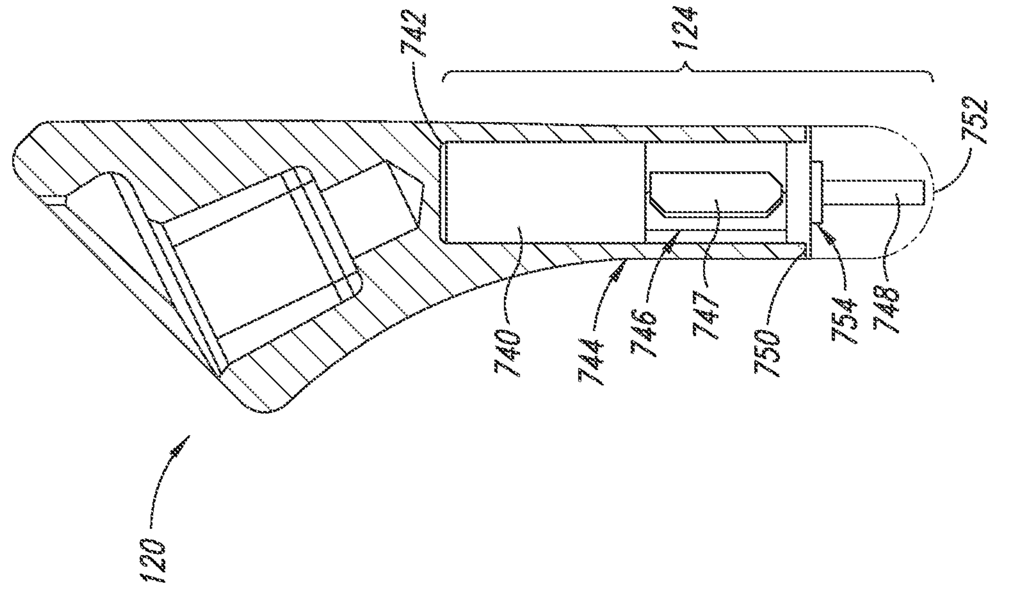
FIGS. 16A and 16B are cross-section illustrations of configurations of the intelligent implant of FIG. 15.
Figure 16A:
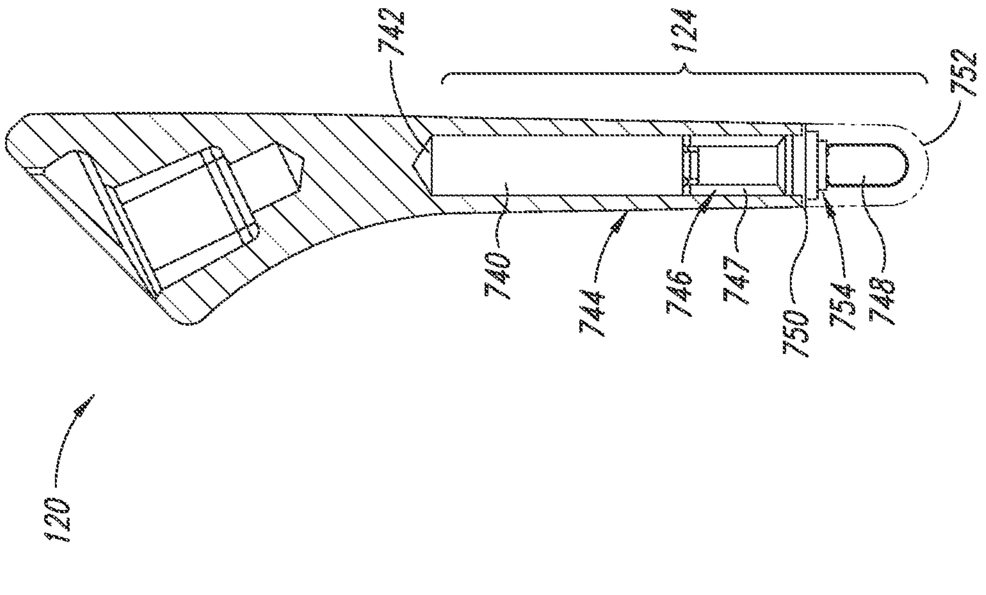

With reference to FIGS. 15, 16A and 16B, an implantable reporting processor 124 is integrated with a humeral component 120 of a shoulder implant system like that shown in FIG. 5A. The implantable reporting processor 124 can be integrated with humeral components of different sizes, including for example a standard size humeral component (shown in FIG. 16A) having a length in the range of 91 mm to 94 mm, and a micro size humeral component (shown in FIG. 16B) having a length in the range of 66 mm to 69 mm. In either configuration, the implantable reporting processor 124 includes a battery 740 configured to fit within a receptacle 742 formed in the humeral stem 744 portion of the humeral component 120, an electronics assembly 746 configured to fit within a receptacle, and an antenna 748 outside the receptacle that extends from the tip 750 of the humeral stem, and a cover 752 that covers the antenna. An antenna feedthrough 754 at the tip 750 of the humeral stem 744 extends partially into the receptacle 742.

Figure 17:
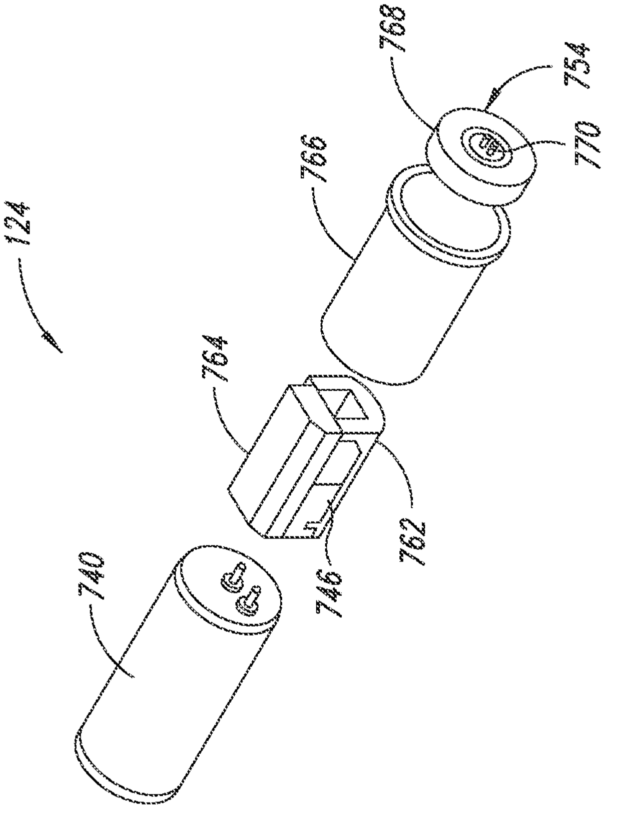
FIG. 17 is an exploded illustration of the implantable reporting processor of the intelligent implant of FIG. 15.

With reference to FIGS. 16A, 16B, and 17, the primary components of the implantable reporting processor 124 include the battery 740, the electronics assembly 746, and the antenna 748. The battery 740 is configured to power the electronic circuitry of the implantable reporting processor 124 over a significant portion (e.g., 1-15+ years, e.g., 10 years, or 15 years), or the entirety (e.g., 18+ years), of the anticipated lifetime of the implantable reporting processor. The battery 740 may be configured the same as described above with reference to FIGS. 8A, 8B, 8C. Accordingly, the details of the battery configuration are not repeated here.

The electronics assembly 746 includes a circuit assembly 747 that has one or more sensors and a processor configured to receive and process information from the sensors relating to the state and functioning of the implantable reporting processor 124 and the state of the patient within which the implantable reporting processor is implanted. The electronics assembly 746 is further configured to transmit the processed information to an external device through the antenna 748. The circuit assembly 747 of the electronics assembly 746 may be configured as described above with reference to FIGS. 14A and 14B. Accordingly, details of the electronics assembly 746 are not repeated here. The antenna 748 may be configured as described below in the Antenna Design section of this disclosure.

With reference to FIG. 17, other components of the implantable reporting processor 124 include a first liner 762, a second liner 764, a sleeve 766, a flange 768, and an implant-grade bipolar feedthrough 770. The first liner 762, a second liner 764 function to mechanically stabilize the electronics assembly 746 within the sleeve 766. The first liner 762 and a second liner 764 can be formed from any suitable material, including for example, polycarbonate. The sleeve 766 can be formed of a biocompatible metallic material. In some embodiments, the material is titanium. The flange 768 is formed of a biocompatible metallic material. In some embodiments, the material is titanium. The antenna spacer 716 is formed of a non-conductive biocompatible material. In some embodiments, the antenna spacer 716 is formed of a PEEK. The feedthrough 770 is formed of a non-conductive biocompatible material. In some embodiments, the feedthrough 770 is formed of a ceramic.

Figure 18A:
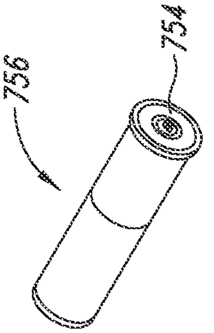
FIGS. 18A, 18B, 18C, 18D, and 18E are a series of illustrations depicting an assembling of the intelligent implant of FIG. 15.
Figure 18B:
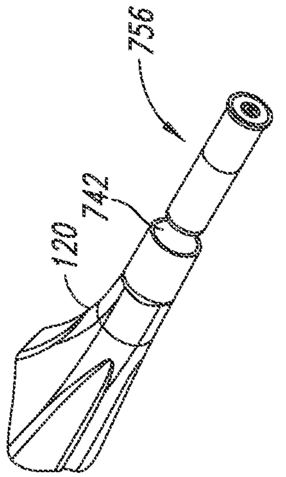
Figure 18C:
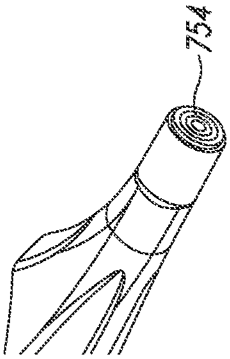
Figure 18D:
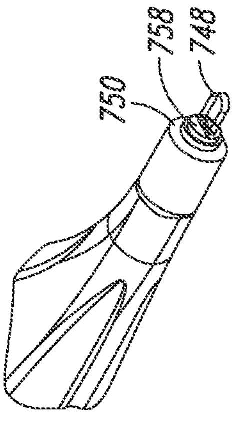
Figure 18E:
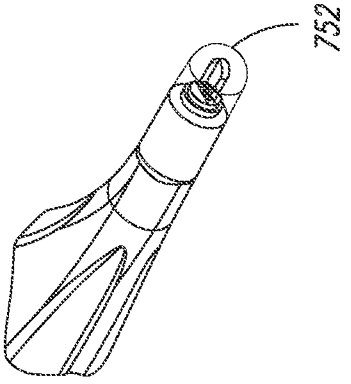

With reference to FIGS. 18A, 18B, 18C, 18D, and 18E, an intelligent implant for a shoulder implant system is assembled from a humeral component 120, a hermetic subassembly 756, an antenna 748, and a cover 752. With reference to FIGS. 18B and 18C, the hermetic subassembly 756 is placed in the receptacle 742 of the humeral component 120 and the distal end of the hermetic subassembly is hermetically welded to the distal end of the humeral component. With reference to FIG. 18D, an antenna spacer 758 is placed over the external pins of the feedthrough 754 (shown in FIG. 18C) of the hermetic subassembly 756, and an antenna 748 is welded to the feedthrough pins. The antenna spacer 716 is formed of a non-conductive biocompatible material. In some embodiments, the antenna spacer 716 is formed of a PEEK. With reference to FIG. 18E, a cover 752 is then assembled onto and secured to the tip 750 of the humeral component 120. In some embodiments, the cover 752 is back-filled with an epoxy (fill and bleed ports not shown). The epoxy material encapsulates the antenna 748 within the cover 752. The epoxy material may be medical grade silicone. Encapsulating the antenna 748 increases structural rigidity of the portion of implantable reporting processor 124 extending from the receptacle 742 of the humeral component 120 and isolates the antenna from tissue and body fluid.

Figure 19:
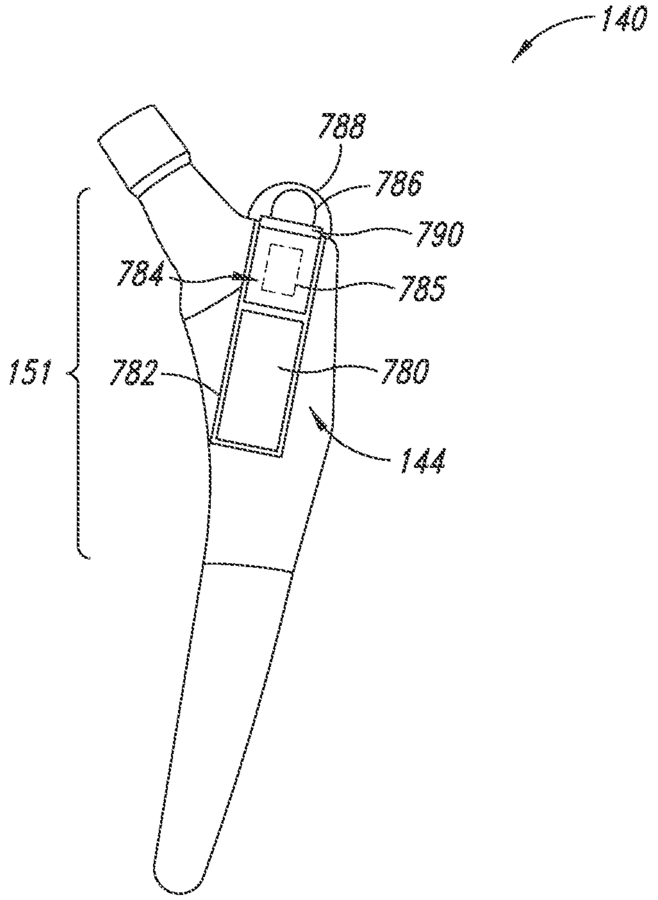
FIG. 19 is an illustration of the intelligent implant (femoral component with integrated implantable reporting processor) of FIGS. 6A and 6B.

With reference to FIG. 19, an implantable reporting processor 144 is integrated with a femoral component 140 of a hip implant system like that shown in FIG. 6A. The implantable reporting processor 144 includes a battery 780 configured to fit within a receptacle 782 formed in the proximal, midline portion 151 of the femoral component 140, an electronics assembly 784 configured to fit within the receptacle, and an antenna 786 outside the receptacle that extends from a surface of the femoral component, and a cover 788 that covers the antenna. An antenna feedthrough 790 of the electronics assembly 784 is positioned at the surface of the femoral component 140 and extends partially into the receptacle 782. The electronics assembly 784 is hermetically welded to the femoral component 140 thereby creating a hermetic chamber within the receptacle 782.

The battery 780 is configured to power the electronic circuitry of the implantable reporting processor 144 over a significant portion (e.g., 1-15+ years, e.g., 10 years, or 15 years), or the entirety (e.g., 18+ years), of the anticipated lifetime of the implantable reporting processor. The battery 780 may be configured the same as described above with reference to FIGS. 8A, 8B, 8C. Accordingly, the details of the battery configuration are not repeated here.

The electronics assembly 784 includes a circuit assembly 785 that one or more sensors and a processor configured to receive and process information from the sensors relating to the state and functioning of the implantable reporting processor 144 and the state of the patient within which the implantable reporting processor is implanted. The electronics assembly 784 is further configured to transmit the processed information to an external device through the antenna 786. The circuit assembly 785 of the electronics assembly 784 may be configured as described above with reference to FIGS. 14A and 14B. Accordingly, details of the electronics assembly 784 are not repeated here. The antenna 786 may be configured as described below in the Antenna Design section of this disclosure.

In some embodiments, during assembly the cover 788 is back-filled with an epoxy (fill and bleed ports not shown). The epoxy material encapsulates the antenna 786 within the cover 788. The epoxy material may be medical grade silicone. Encapsulating the antenna 786 increases structural rigidity of the portion of implantable reporting processor 144 extending from the receptacle 782 of the femoral component 140 and isolates the antenna from tissue and body fluid.

With reference to FIGS. 4A and 4B, an implantable reporting processor 404 is integrated with a tibial component 400 of a knee implant system. The implantable reporting processor 404 includes a subassembly 409 configured to fit within a receptacle 412 formed in the tibial stem 410 portion of the tibial component. The subassembly 409 includes a battery 413, an electronics assembly 415, an antenna feedthrough 417, and an antenna 419. When the subassembly 409 is placed in the receptacle 412 the battery 413 and the electronics assembly 415 are located inside the receptacle 412, while the antenna 419 is positioned outside the receptacle. The antenna feedthrough 417 extends partially into the receptacle 412. The electronics assembly 415 portion of the subassembly 409 is hermetically welded to the tibial stem 410 thereby creating a hermetic chamber within the receptacle 412 within which the battery 413 and the electronics assembly 415 reside. A cover 411 covers the antenna 419 and may be secured to the tibial stem 410 through a threaded coupling. Alternatively, the cover 411 may be over molded to the subassembly 409 prior to placement of the subassembly in the receptacle 412.

The battery 413 is configured to power the electronic circuitry of the implantable reporting processor 404 over a significant portion (e.g., 1-15+ years, e.g., 10 years, or 15 years), or the entirety (e.g., 18+ years), of the anticipated lifetime of the implantable reporting processor. The battery 413 may be configured the same as described above with reference to FIGS. 8A, 8B, 8C. Accordingly, the details of the battery configuration are not repeated here.

The electronics assembly 415 includes one or more sensors and a processor configured to receive and process information from the sensors relating to the state and functioning of the implantable reporting processor 404 and the state of the patient within which the implantable reporting processor is implanted. The electronics assembly 415 is further configured to transmit the processed information to an external device through the antenna 419. The electronics assembly 415 may be configured as described above with reference to FIGS. 14A and 14*b*. Accordingly, details of the electronics assembly 415 are not repeated here. The antenna 419 may be configured as described below in the Antenna Design section of this disclosure.

In some embodiments, during assembly the cover 411 is back-filled with an epoxy (fill and bleed ports not shown). The epoxy material encapsulates the antenna 419 within the cover 411. The epoxy material may be medical grade silicone. Encapsulating the antenna 419 increases structural rigidity of the portion of implantable reporting processor 404 extending from the receptacle 412 of the tibial component 400 and isolates the antenna from tissue and body fluid.

Antenna Design

With reference to FIG. 20A-20E, the antenna for the above disclosed component-assembly IRPs and integrated IRPs are designed to transmit information generated by the electronics assembly of the IRP to a remote destination outside of the body of a subject in which the intelligent implant is implanted, and to receive information from a remote source outside of the subject's body. In some embodiments, the antenna 208, 318, 419, 748, 786 is a flat ribbon 902 configured in a loop 904 having a curved end 906, a flat end 908 opposite the curved end, and a pair of opposed sides 910, 912 that extend between the curved end and the flat end. The flat ribbon 902 forming the antenna 208, 318, 419, 748, 786 has a major surface 914 and a minor edge 916.

Figure 20A:
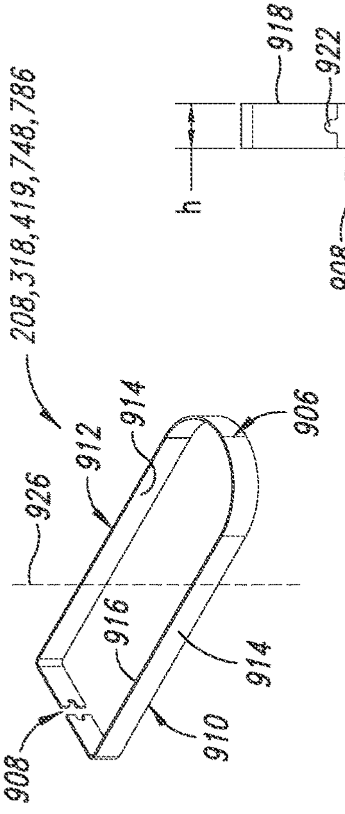
FIGS. 20A, 20B, 20C, 20D, and 20E are detailed views of the antenna of the implantable reporting processors of FIGS. 7A and 12A and the intelligent implants of FIGS. 15 and 19.
Figure 20B:
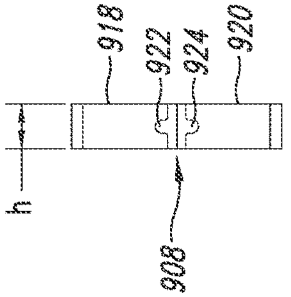
Figure 20C:
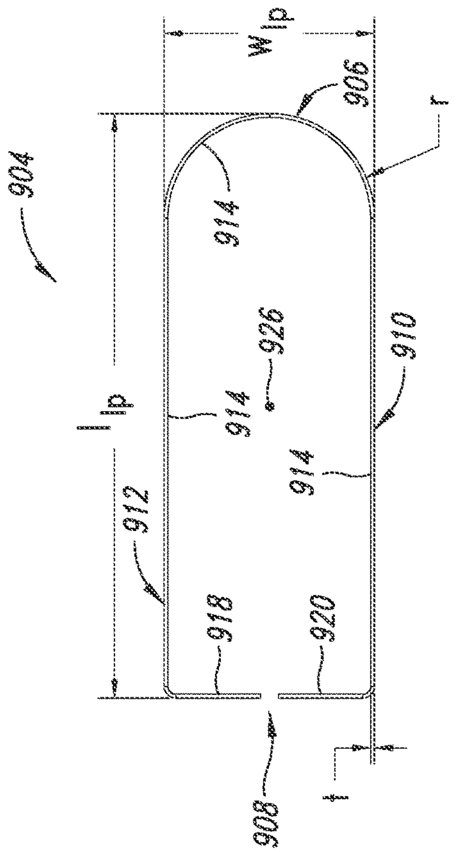
Figure 20D:
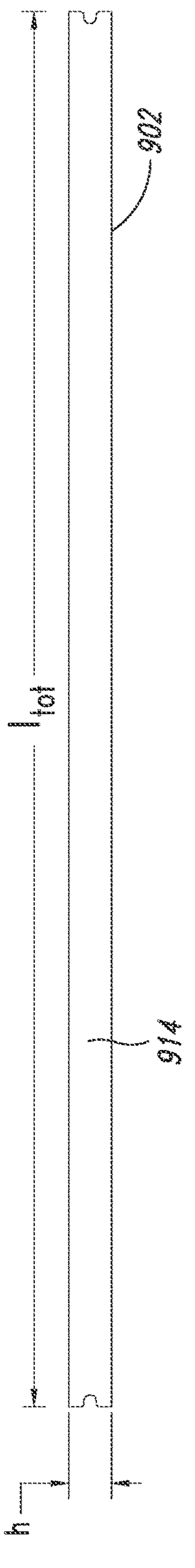
Figure 20E:
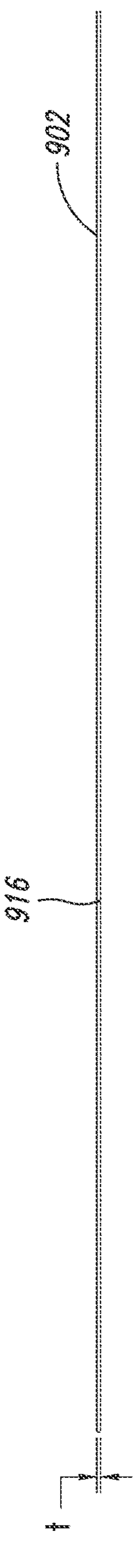

With reference to FIGS. 20B-20E, in one example embodiment where the antenna 208, 419 may be for use in the IRP of FIGS. 7A and 7B or the IRP of FIGS. 4A and 4B, the antenna has a loop length ($l_{lp}$) of 19.507 mm (0.768 inches), a loop width ($w_{lp}$) of 7.101 mm (0.276 inches), a radius of curvature (r) at the curved end 906 of 3.505 mm (0.138 inches), a thickness (t) of 0.127 mm (0.0050 inches), and a height (h) of 1.5 mm (0.059 inches). With reference to FIG. 20C, the loop area ($l_{lp} \times w_{lp}$) of the antenna 208 is approximately 138.52 $mm^2$ (0.222 square inches). With reference to FIG. 20D, the total length ($l_{tot}$) of the flat ribbon 902 forming the loop 904 is 48.565 mm (1.912 inches). Accordingly, the cross-sectional surface area ($l_{tot} \times h$) of the major surface 914 of the antenna is approximately 72.8475 $mm^2$ (0.113 square inches).

With continued reference to FIGS. 20B-20E, in another example embodiment where the antenna 318, 748 may be for use in the IRP of FIGS. 12A and 12B or the IRP of FIGS. 16A and 16B, the antenna has a loop length ($l_{lp}$) of 7.62 mm (0.300 inches), a loop width ($w_{lp}$) of 8.128 mm (0.32 inches), a radius of curvature (r) at the curved end 906 of 4.064 mm (0.16 inches, a thickness (t) of 0.127 mm (0.0050 inches), and a height (h) 1.5 mm (0.059 inches). With reference to FIG. 9C, the loop area ($l_{lp} \times w_{lp}$) of the antenna 208 is approximately 61.93 $mm^2$ (0.096 square inches). With reference to FIG. 9D, the total length ($l_{tot}$) of the flat ribbon 902 forming the loop 904 is 21.3687 mm (0.841 inches). Accordingly, the cross-sectional surface area ($l_{tot} \times h$) of the major surface 914 of the antenna is approximately 32.05 $mm^2$ (0.0496 square inches).

Regarding the foregoing dimensions of the antenna 208, 318, 419, 748, 786, due to skin-effect on RF transmission it is desirable to maximize the cross-sectional surface area of the antenna to minimize RF energy loss, while simultaneously minimizing PtIr volume, to thereby minimize cost. The thickness of the flat ribbon 902 represents an approximate minimum to maintain antenna shape during assembly, and the height (h) of the flat ribbon is such to achieve necessary surface area.

With reference to implantable reporting processor 104 shown in FIGS. 8A and 8B, the antenna 208 is located within the cover 210 of the housing in an orientation wherein the major surface 914 of the antenna is generally parallel with the inner surface 508 of the cover 210 along the length of the opposed sides 910, 912 and curved end 906 of the loop 904. "Generally parallel" refers to a relationship between adjacent surfaces facing each other, wherein one surface is parallel to the other or within a degree range, e.g., within 25 degrees, of being parallel. To this end, the cover 210 includes a dome-shaped closed end 510 and a sidewall portion 512 that extends from the dome-shaped closed end, and the curved end 906 of the antenna 208 is located in the dome-shaped closed end, while the opposed sides of the antenna are surrounded by the sidewall. Orientation of the major surface 914 of the antenna generally parallel with the inner surface 508 of the cover 210 maximizes the area inside the flat-ribbon loop of the antenna, which in turn maximizes the amount of magnetic flux that can flow through the open area and provides improved antenna performance.

The orientation of the antenna 208 may also be described in terms of the antenna itself. For example, with reference to FIGS. 8A, 8B, and 20A-20C, the antenna 208 is located within the cover 210 of the housing in an orientation wherein the major surface 914 of the antenna faces an axis 926 that extends through the center of the loop 904, where the axis is normal to a plane bounded by the loop 904. In other words, the major surface 914 lies in a plane generally parallel to an axis normal to the area bounded by the loop. Or, alternatively stated, the major surface 914 of the antenna 208 lies in a plane generally perpendicular to a plane bound by the loop 904. "Generally perpendicular" refers to a relationship between planes, wherein one plane is perpendicular to the other or within a degree range, e.g., within 25 degrees, of being perpendicular. Again, orientation of the major surface 914 of the antenna in this manner maximizes the area inside the loop of the antenna, which in turn maximizes the amount of magnetic flux that can flow through the open area and provides improved antenna performance.

With reference to FIGS. 8A and 8B, and 20A-20C, the flat end 908 of the antenna 208 electrically couples to the electronics assembly 206. To this end, the flat end 908 of the antenna 208 comprises a first portion 918 separated by a gap from a second portion 920. The first portion 918 includes a first notch 922 at an edge configured to couple with a first feedthrough pin 514 of the electronics assembly 206. The second portion 920 includes a second notch 924 at an edge configured to couple with a second feedthrough pin 516 of the electronics assembly.

The foregoing disclosed arrangement, orientation, and electrical coupling of the antenna 208 of the implantable reporting processor 104 shown in FIGS. 8A and 8B also describes the arrangement, orientation, and electrical coupling of the antenna 318 of the implantable reporting processor 304 shown in FIGS. 12A and 12B, the antenna 419 of the implantable reporting processor 404 shown in FIGS. 4A and 4B, the antenna 748 of the implantable reporting processor 404 shown in FIGS. 16A and 16B, and the antenna 786 of the implantable reporting processor 144 shown in FIGS. 19. Accordingly, details of the arrangement, orientation, and electrical coupling of these antenna are not repeated here.

Regarding the material and surface finish of the antenna 208, 318, 419, 748, 786, in some embodiments, the antenna is formed of a material comprising platinum (Pt) with an atomic percentage in a range of 70% to 100%, and iridium (Ir) with an atomic percentage in a range of 0% to 30%. In one example configuration, the antenna 208, 318, 419, 748, 786 is formed of Pt90Ir10. Platinum and Pt—Ir alloys are selected for a combination of biocompatibility, ductility, and electrical conductivity.

In some embodiments the major surfaces 914 of the antenna 208, 318, 419, 748, 786 have a surface finish in a range of 0 micro inches and 15 micro inches maximum. In one example configuration, the surface finish is 6 micro inches maximum.

As described above, in configurations of IRPs the antenna 208, 318, 419, 748, 786 is coupled to the electronics assembly through a dielectric feedthrough, with a dielectric PEEK cover and a backfill encasing the antenna. The backfill may be silicone or a medical grade epoxy adhesive. Encasing an antenna in dielectrics, coupled with post-implant placement of the antenna in boney tissue and muscle may affect antenna performance. However, the antenna 208, 318, 419, 748, 786 design, e.g., geometry, orientation, material composition, surface finish, etc., disclosed herein in combination with circuitry of the electronics assembly 206 enables post-implant communication at both 2.45 GHz and a medical implant communications system (MICS) frequency band, e.g., 401-406 MHz, despite the surrounding presence of dielectrics and tissue.

Figure 21:
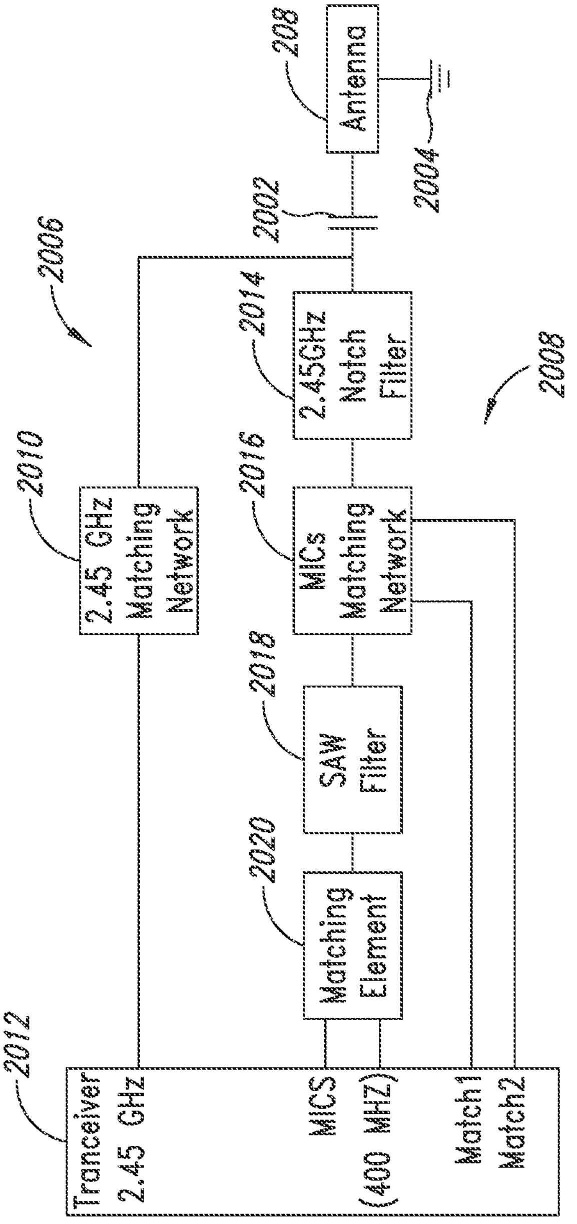
FIG. 21 is a schematic block diagram of an antenna coupled to electronics of an electronics assembly.

In one configuration a loop antenna 208 having the physical properties described above with reference to FIGS. 20A-20E is tuned to enable post-implant reception of an ultra-low power wakeup sniff signal on a 2.45 GHz channel, while also being tuned to enable post-implant reception and transmission of data and information on a MICS channel, e.g., a 400 MHz channel. To this end, and with reference to FIG. 21, one end of the antenna 208 is coupled to a DC blocking capacitor 2002, while the other end is coupled to ground 2004. The DC blocking capacitor 2002 is coupled to parallel signal pathways including a 2.45 GHz signal pathway 2006 and a 400 MHz signal pathway 2008.

The 2.45 GHz pathway 2006 includes a 2.45 GHz matching network 2010. The 2.45 GHz matching network 2010 is coupled to the 2.45 GHz input port of the transceiver 2012 and provides 2.45 GHz signals to a transceiver 2012. The 2.45 GHz matching network 2010 matches the antenna 208 impedance to the impedance of the 2.45 GHz input of the transceiver to enable communication of wake up signals on a 2.45 GHz channel. In some embodiments, the matching impedance is greater than 50 Ohms. In some embodiments, the matching impedance is greater than 100 Ohms. In some embodiments, the matching impedance is greater than 500 Ohms. In some embodiments, the matching impedance is in the range of 100 Ohms to 800 Ohms.

The 400 MHz signal pathway 2008 includes a 2.45 GHz notch filter 2014, a MICS matching network 2016, a SAW bandpass filter 2018, and a matching element 2020 that is coupled to the 400 MHz input and output ports of the transceiver 2012. The 2.45 GHz notch filter 2008 rejects 2.45 GHz signals from the 400 MHz pathway. The SAW bandpass filter 2018 further filters the signal to reduce out-of-band signals coming into the transceiver 2012 on the 400 MHz signal pathway 2008.

The MICS matching network 2016 includes one or more circuit components and in some embodiments is firmware tunable via a first match port and second match port of the transceiver 2012. The MICS matching network 2016, together with the matching element 2020 at the MICS input of the transceiver 2012, matches the antenna 208 impedance to the impedance of the MICS input and output to enable communication on a 400 MHz channel. In some embodiments, the matching impedance at the input of the SAW bandpass filter 2018, as set by the MICS matching network 2016, is greater than 50 Ohms. In some embodiments, the matching impedance at the input of the SAW bandpass filter 2018 is greater than 100 Ohms. In some embodiments, the matching impedance at the input of the SAW bandpass filter 2018 is in the range of 100 Ohms to 500 Ohms. In some embodiments, the matching impedance at the MICS input of the transceiver 2012, as set by the matching element 2020, is greater than 10 Ohms. In some embodiments, the matching impedance at the MICS input of the transceiver 2012 is in the range of 10 Ohms to 200 Ohms.

Electronics Assembly

Figure 22:
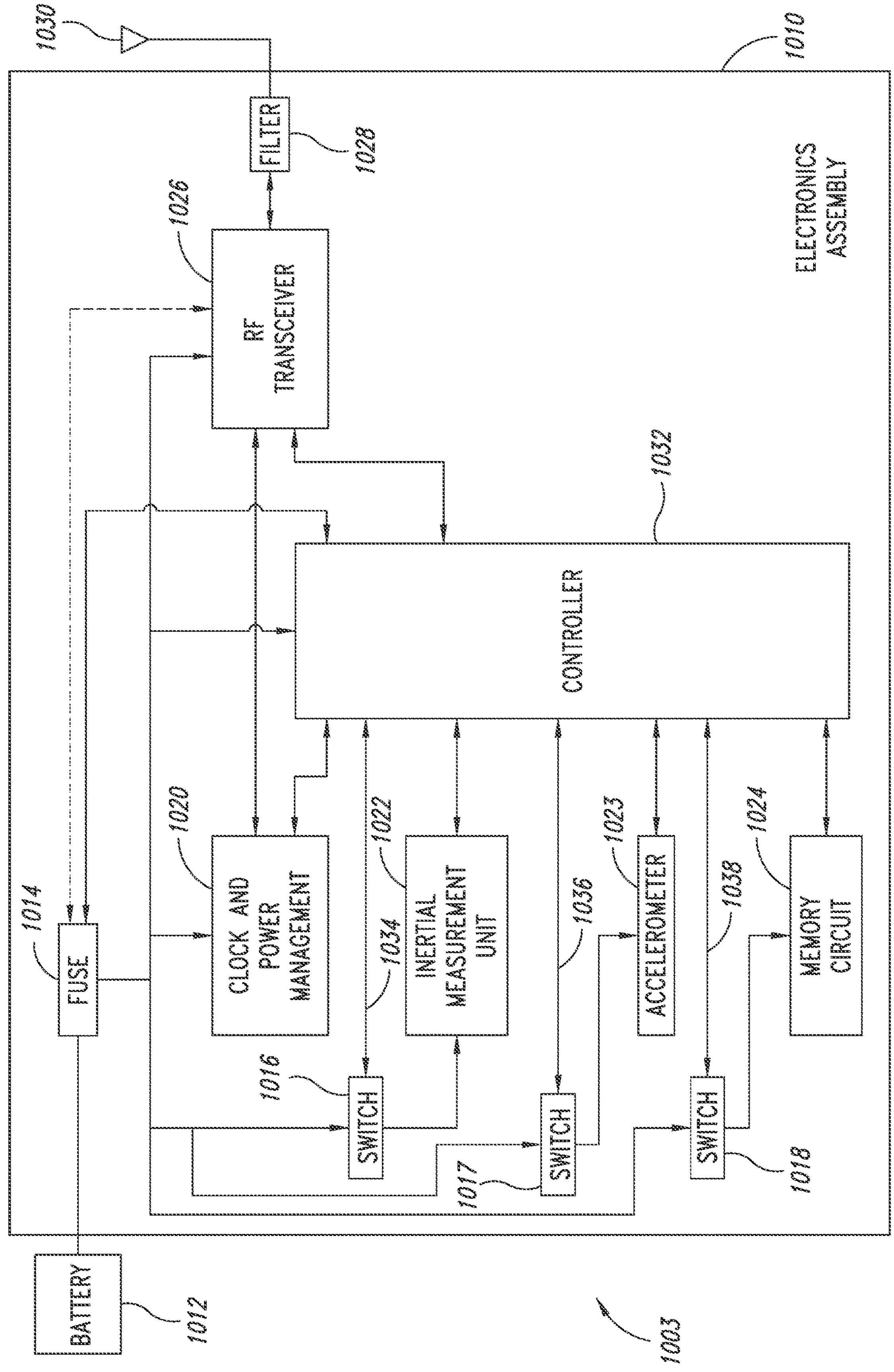
FIG. 22 is a block diagram of an implantable reporting processor (IRP).

With reference to the block diagram of FIG. 22, an implantable reporting processor 1003 includes an electronics assembly 1010, a battery 1012 or other suitable implantable power source, and an antenna 1030. The electronics assembly 1010 comprises a circuit assembly that includes a fuse 1014, switches 1016, 1017, and 1018, a clock generator and clock and power management circuit 1020, an inertial measurement unit (IMU) 1022, a memory circuit 1024, a radio-frequency (RF) transceiver 1026, an RF filter 1028 and a controller 1032. The electronics assembly 1010 may also include an accelerometer 1023. The accelerometer 1023 may be a single axis or multi-axis accelerometer, and in one embodiment is a triaxial accelerometer. Examples of some or all of these components are described elsewhere in this application and in PCT Publication Nos. WO 2017/165717 and WO 2020/247890, which are incorporated by reference.

The battery 1012 can be any suitable battery, such as a Lithium Carbon Monofluoride (LiCFx) battery, or other storage cell configured to store energy for powering the electronics assembly 1010 for an expected lifetime (e.g., 5-25+ years) of the kinematic implant.

The fuse 1014 can be any suitable fuse (e.g., permanent) or circuit breaker (e.g., resettable) configured to prevent the battery 1012, or a current flowing from the battery, from injuring the patient and damaging the battery and one or more components of the electronics assembly 1010. For example, the fuse 1014 can be configured to prevent the battery 1012 from generating enough heat to burn the patient, to damage the electronics assembly 1010, to damage the battery, or to damage structural components of the kinematic implant.

The switch 1016 is configured to couple the battery 1012 to, or to uncouple the battery from, the IMU 1022 in response to a control signal 1034 from the controller 1032. For example, the controller 1032 may be configured to generate the control signal 1034 having an open state that causes the switch 1016 to open, and, therefore, to uncouple power from the IMU 1022, during a sleep mode or other low-power mode to save power, and, therefore, to extend the life of the battery 1012. Likewise, the controller 1032 also may be configured to generate the control signal 1034 having a closed state that causes the switch 1016 to close, and therefore, to couple power to the IMU 1022, upon "awakening" from a sleep mode or otherwise exiting another low-power mode. Such a low-power mode may be for only the IMU 1022 or for the IMU and one or more other components of the implantable reporting processor 1003.

The switch 1017 is configured to couple the battery 1012 to, or to uncouple the battery from, the accelerometer 1023 in response to a control signal 1036 from the controller 1032. For example, the controller 1032 may be configured to generate the control signal 1036 having an open state that causes the switch 1017 to open, and, therefore, to uncouple power from the accelerometer 1023, during a sleep mode to save power, and, therefore, to extend the life of the battery 1012. Likewise, the controller 1032 also may be configured to generate the control signal 1036 having a closed state that causes the switch 1017 to close, and therefore, to couple power to the accelerometer 1023, upon "awakening" from a sleep mode.

The switch 1018 is configured to couple the battery 1012 to, or to uncouple the battery from, the memory circuit 1024 in response to a control signal 1038 from the controller 1032. For example, the controller 1032 may be configured to generate the control signal 1038 having an open state that causes the switch 1018 to open, and, therefore, to uncouple power from the memory circuit 1024, during a sleep mode or other low-power mode to save power, and, therefore, to extend the life of the battery 1012. Likewise, the controller 1032 also may be configured to generate the control signal 1038 having a closed state that causes the switch 1018 to close, and therefore, to couple power to the memory circuit 1024, upon "awakening" from a sleep mode or otherwise exiting another low-power mode. Such a low-power mode may be for only the memory circuit 1024 or for the memory circuit and one or more other components of the electronics assembly 1010.

The clock circuit 1020 is configured to generate a clock signal for one or more of the other components of the electronics assembly 1010, and can be configured to generate periodic commands or other signals (e.g., interrupt requests) in response to which the controller 1032 causes one or more components of the implantable circuit to enter or to exit a sleep, or other low-power, mode. In some embodiments, the clock circuit 1020 is also configured to regulate the voltage from the battery 1012, and to provide a regulate power-supply voltage to some or all of the other components of the electronics assembly 1010. In these embodiments, the clock circuit 1020 may be referred to as a clock and power management circuit.

The IMU 1022 has a frame of reference with coordinate x, y, and z axes, and can be configured to measure, or to otherwise quantify, linear acceleration that the IMU experiences along each of the x, y, and z axes, and angular velocity (or rotational motion) that the IMU experiences about each of the x, y, and z axes. Such a configuration of the IMU 1022 is at least a six-axis configuration, because the IMU 1022 measures six unique quantities, $a_x$(g), $a_y$(g), $a_z$(g), $\Omega_x$(dps), $\Omega_y$(dps), and $\Omega_z$(dps). Alternatively, the IMU 1022 can be configured in a nine-axis configuration, in which the IMU can use the earth magnetic field to compensate for, or to otherwise correct for, accumulated errors in $a_x$(g), $a_y$(g), $a_z$(g), $\Omega_x$(dps), $\Omega_y$(dps), and $\Omega_z$(dps). But in an embodiment in which the IMU measures acceleration and angular velocity over only short bursts (e.g., 0.10-100 seconds(s)), for many applications accumulated error typically can be ignored without exceeding respective error tolerances.

The IMU 1022 can include a respective analog-to-digital converter (ADC) for each of the x, y, and z accelerometers and gyroscopes. Alternatively, the IMU 1022 can include a respective sample-and-hold circuit for each of the x, y, and z accelerometers and gyroscopes, and as few as one ADC that is shared by the accelerometers and gyroscopes. Including fewer than one ADC per accelerometer and gyroscope can decrease one or both of the size and circuit density of the IMU 1022, and can reduce the power consumption of the IMU. But because the IMU 1022 includes a respective sample-and-hold circuit for each accelerometer and each gyroscope, samples of the analog signals generated by the accelerometers and the gyroscopes can be taken at the same or different sample times, at the same or different sample rates, and with the same or different output data rates (ODR).

The accelerometer 1023 is configured to monitor acceleration in a low power state. The accelerometer 1023 may be a single axis or multi-axis accelerometer, and in one embodiment is a triaxial accelerometer. In the case of a triaxial configuration, the accelerometer 1023 can include a respective ADC for each of the x, y, and z accelerometers. Alternatively, the accelerometer 1023 can include a respective sample-and-hold circuit for each of the x, y, and z accelerometers, and as few as one ADC that is shared by the accelerometers. Including fewer than one ADC per accelerometer can decrease one or both of the size and circuit density of the accelerometer 1023, and can reduce the power consumption of the accelerometer 1023. Based on acceleration signals it senses, the accelerometer 1023 can detect motion events. For example, the accelerometer can be configured to detect simple motion events, such as footsteps or shoulder swings, and to count such detections. The accelerometer can be configured to detect significant motion, such as a walking motion or arm swinging motion. The accelerometer 1023 is configured to provide a wake-up signal to the controller 1032 when significant motion is detected.

The memory circuit 1024 can be any suitable nonvolatile memory circuit, such as EEPROM or FLASH memory, and can be configured to store data written by the controller 1032, and to provide data in response to a read command from the controller.

The RF transceiver 1026 can be a conventional transceiver that is configured to allow the controller 1032 (and optionally the fuse 1014) to communicate with a base station (not shown in FIG. 22) configured for use with the kinematic implantable device. For example, the RF transceiver 1026 can be any suitable type of transceiver (e.g., Bluetooth, Bluetooth Low Energy (BTLE), and WiFi®), can be configured for operation according to any suitable protocol (e.g., MICS, ISM, Bluetooth, Bluetooth Low Energy (BTLE), and WiFi®), and can be configured for operation in a frequency band that is within a range of 1 MHz-5.4 GHz, or that is within any other suitable range.

The RF filter 1028 can be any suitable bandpass filter, such as a surface acoustic wave (SAW) filter or a bulk acoustic wave (BAW) filter. In some embodiment, the RF filter 1028 includes multiple filters and other circuitry to enable dual-band communication. For example, the RF filter 1028 may include a bandpass filter for communications on a MICS channel, and a notch filter for communication on a different channel, such as a 2.45 GHz as described above with reference to FIG. 21.

The antenna 1030 can be any antenna suitable for the frequency band in which the RF transceiver 1026 generates signals for transmission by the antenna, and for the frequency band in which a base station generates signals for reception by the antenna. In some embodiments the antenna 1030 is configured as a flat ribbon loop antenna as described above with reference to FIGS. 20A-20E The controller 1032, which can be any suitable micro-controller or microprocessor, is configured to control the configuration and operation of one or more of the other components of the electronics assembly 1010. For example, the controller 1032 is configured to control the IMU 1022 to take measurements of movement of the implantable medical device with which the electronics assembly 1010 is associated, to quantify the quality of such measurements (e.g., is the measurement "good" or "bad"), to store measurement data generated by the IMU in the memory 1024, to generate messages that include the stored data as a payload, to packetize the messages, to provide the message packets to the RF transceiver 1026 for transmission to an external device, e.g. a base station. The controller 1032 may be configured to execute commands received from an external device via the antenna 1030, the RF filter 1028, and the RF transceiver 1026. For example, the controller 1032 can be configured to receive configuration data from a base station, and to provide the configuration data to the component of the electronics assembly 1010 to which the base station directed the configuration data. If the base station directed the configuration data to the controller 1032, then the controller is configured to configure itself in response to the configuration data. The controller 1032 may also be configured to execute data sampling by the IMU 1022 in accordance with one or more programmed sampling schedules, or in response to an on-demand data sampling command received from a base station. For example, as described later below, the implantable reporting processor 104 may be programmed to operate in accordance with a master sampling schedule and a periodic, e.g., daily, sampling schedule.

Inertial Measurement Unit

Figure 23:
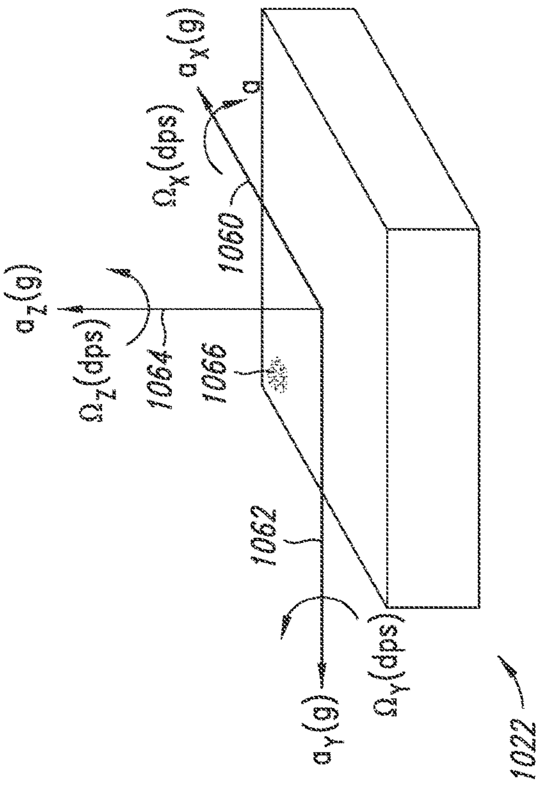
FIG. 23 is a perspective view of an inertial measurement unit (IMU) of the implantable circuit of FIG. 22 and of a set of coordinate axes within the frame of reference of the IMU.

FIG. 23 is a perspective view of the IMU 1022 of FIG. 22, according to an embodiment. For example, the IMU 1022 can be a Bosch BMI 160 small, low-power, IMU.

As described above in conjunction with FIG. 22, the IMU 1022 includes three measurement axes 1060, 1062, and 1064, which for purposes of description, are arbitrarily labeled x, y, z. That is, in a Cartesian coordinate system, the labels "x," "y," and "z" can be applied arbitrarily to the axes 1060, 1062, and 1064 in any order or arrangement. A mark 1066 is a reference that indicates the locations and orientations of the axes 1060, 1062, and 1064 relative to the IMU 1022 package.

The IMU 1022 includes three accelerometers (not shown in FIG. 23), each of which senses and measures a linear acceleration a(t) along a respective one of the axes 1060 ($x$), 1062 ($y$), and 1064 ($z$), where $a_x(t)$ is the acceleration along the x axis, $a_y(t)$ is the acceleration along the y axis, and $a_z(t)$ is the acceleration along the z axis. Each accelerometer generates a respective analog sense or output signal having an instantaneous magnitude that represents the instantaneous magnitude of the sensed acceleration along the corresponding axis. For example, the magnitude of the magnitude of the accelerometer output signal at a given time is proportional the magnitude of the acceleration along the accelerometer's sense axis at the same time.

The IMU 1022 also includes three gyroscopes (not shown in FIG. 23), each of which senses and measures angular velocity Ω(t) about a respective one of the axes 1060 ($x$), 1062 ($y$), and 1064 ($z$), where $\Omega_x(t)$ is the angular velocity along the x axis, $\Omega_y(t)$ is the angular velocity along the y axis, and $\Omega_z(t)$ is the angular velocity along the z axis. Each gyroscope generates a respective analog sense or output signal having an instantaneous magnitude that represents the instantaneous magnitude of the sensed angular velocity about the corresponding axis. For example, the magnitude of the gyroscope output signal at a given time is proportional the magnitude of the angular velocity about the gyroscope's sense axis at the same time.

The IMU 1022 includes at least two analog-to-digital converters (ADCs) (not shown in FIG. 23) for each axis 1060, 1062, and 1064, one ADC for converting the output signal of the corresponding accelerometer into a corresponding digital acceleration signal, and the other ADC for converting the output signal of the corresponding gyroscope into a corresponding digital angular-velocity signal. For example, each of the ADCs may be an 8-bit, 16-bit, or 24-bit ADC.

Each ADC (not shown in FIG. 23) may be configured to have respective parameter values that are the same as, or that are different from, the parameter values of the other ADCs. Examples of such parameters having settable values include sampling rate, dynamic range at the ADC input node(s), and output data rate (ODR). One or more of these parameters may be set to a constant value, while one or more others of these parameters may be settable dynamically (e.g., during run time). For example, the respective sampling rate of each ADC may be settable dynamically so that during one sampling period the sampling rate has one value and during another sampling period the sampling rate has another value.

For each digital acceleration signal and for each digital angular-velocity signal, the IMU 1022 can be configured to provide the parameter values associated with the signal. For example, the IMU 1022 can provide, for each digital acceleration signal and for each digital angular-velocity signal, the sampling rate, the dynamic range, and a time stamp indicating the time at which the first sample or the last sample was taken. The IMU 1022 can be configured to provide these parameter values in the form of a message header (the corresponding samples form the message payload) or in any other suitable form.

Accelerometer

As described above in conjunction with FIG. 22, the accelerometer 1023 includes three accelerometers, each of which senses and measures a linear acceleration a(t) along a respective one of the axes 1060 ($x$), 1062 ($y$), and 1064 ($z$), where $a_x(t)$ is the acceleration along the x axis, $a_y(t)$ is the acceleration along the y axis, and $a_z(t)$ is the acceleration along the z axis. These three measurement axes 1060, 1062, and 1064 are the same as the measurement axes of the IMU illustrated in FIG. 23. Each accelerometer generates a respective analog sense or output signal having an instantaneous magnitude that represents the instantaneous magnitude of the sensed acceleration along the corresponding axis. For example, the magnitude of the magnitude of the accelerometer output signal at a given time is proportional the magnitude of the acceleration along the accelerometer's sense axis at the same time. The accelerometer 1023 can be a Bosch BMA400 accelerometer The accelerometer 1023 includes an ADC for each axis 1060, 1062, and 1064 for converting the output signal of the corresponding accelerometer into a corresponding digital acceleration signal. For example, each of the ADCs may be an 8-bit, 16-bit, or 24-bit ADC.

Each ADC may be configured to have respective parameter values that are the same as, or that are different from, the parameter values of the other ADCs. Examples of such parameters having settable values include sampling rate, dynamic range at the ADC input node(s), and output data rate (ODR). One or more of these parameters may be set to a constant value, while one or more others of these parameters may be settable dynamically (e.g., during run time). For example, the respective sampling rate of each ADC may be settable dynamically so that during one sampling period the sampling rate has one value and during another sampling period the sampling rate has another value.

For each digital acceleration signal, the accelerometer 1023 can be configured to provide the parameter values associated with the signal. For example, the accelerometer 1023 can provide, for each digital acceleration signal, the sampling rate, the dynamic range, and a time stamp indicating the time at which the first sample or the last sample was taken. The accelerometer 1023 can be configured to provide these parameter values in the form of a message header (the corresponding samples form the message payload) or in any other suitable form.

Knee Kinematic Data

Figure 24:
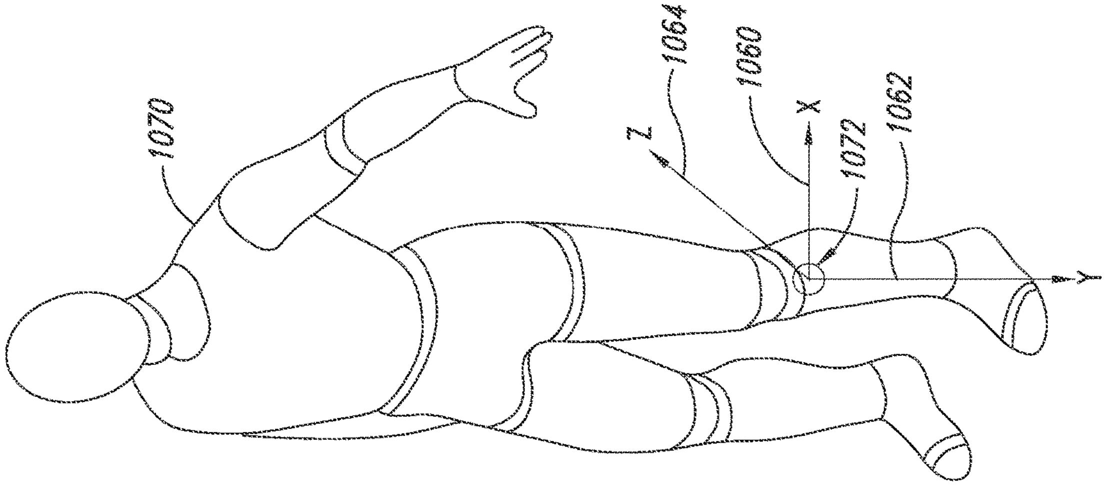
FIG. 24 is an illustration of a set of coordinate axes of an IMU relative to a patient in which a knee prosthesis is implanted.

FIG. 24 is an illustration of a set of coordinate axes of an IMU of an IRP relative to a patient in which a knee prosthesis 1072 is implanted. With respect to the anatomy of the patient, the positive portion of the x-axis 1060 extends in the direction outward from the leg. In other words, the positive portion of the x-axis 1060 extends away from the other leg of the patient. The positive portion of the y-axis 1062 extends in the direction downward toward the foot of the patient. The positive portion of the z-axis 1064 extends in the direction outward from the back of the knee of the patient.

Figure 25A:
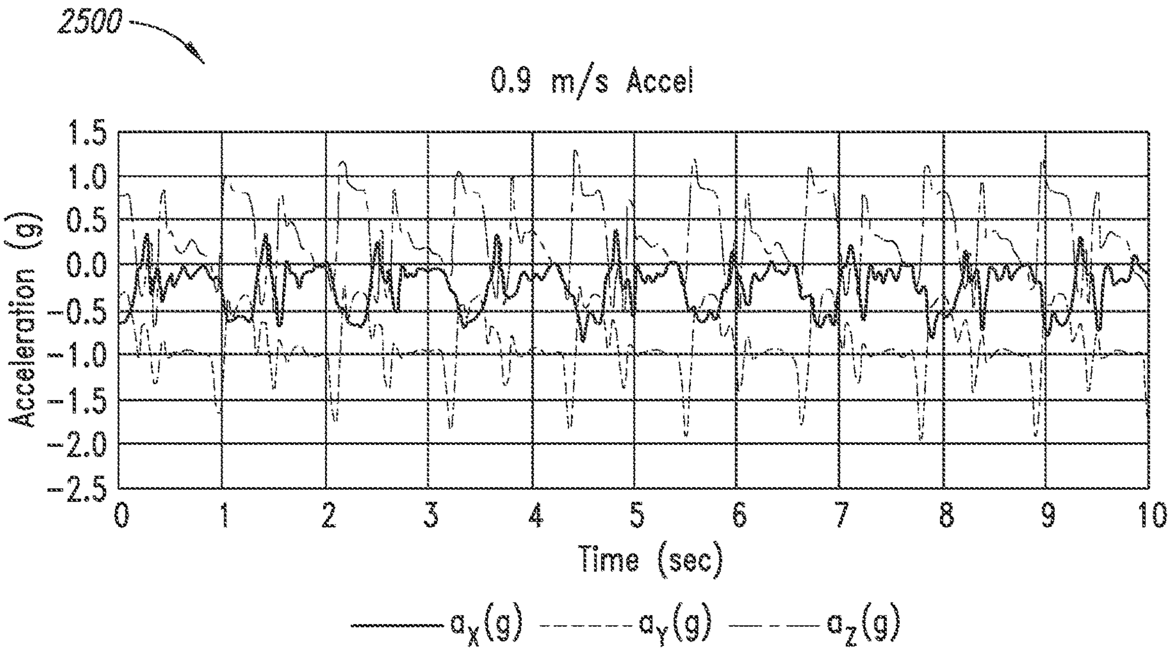
FIG. 25A is a plot, versus time, of linear acceleration signals $a_x(g)$, $a_y(g)$, and $a_z(g)$ (in units of g-force) generate in response to accelerations along the x axis, the y axis, and the z axis of FIG. 23 while the patient of FIG. 24 is walking forward with a normal gait at speeds of 0.9 meters/second.

FIG. 25A is a plot 2500, versus time, of the digitized versions of the analog acceleration signals $a_x$(g), $a_y$(g), and $a_z$(g) as a function of time that the accelerometers of the IMU 1022 respectively generate in response to accelerations along the x-axis 1060, the y-axis 1062, and the z-axis 1064 while the patient 1070 is walking forward with a normal gait at a speed of 0.9 meters/second and for a period of about ten seconds. In this example, the IMU 1022 samples each of the analog acceleration signals $a_x$(g), $a_y$(g), and $a_z$(g) at the same sample times, the sampling rate is 3200 Hz, and the output data rate (ODR) is 800 Hz. The ODR is the rate of the samples output by the IMU 1022 and is generated by down sampling the samples taken at 3200 Hz. That is, because 3200 Hz/800 Hz=4, the IMU 1022 generates an 800 Hz ODR by outputting only every fourth sample taken at 3200 Hz.

Figure 25B:
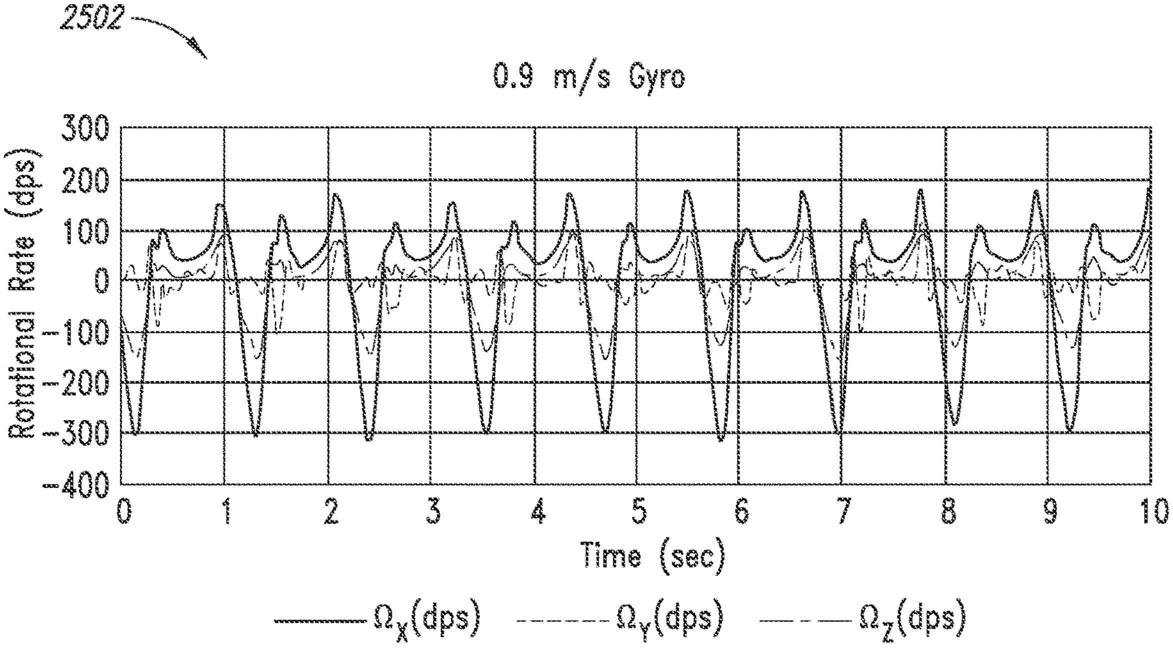
FIG. 25B is a plot, versus time, of angular-velocity (rotational-motion) signals $\Omega_x$(dps), $\Omega_y$(dps), and $\Omega_z$(dps) (in units of degrees per second) generated in response to angular velocities about the x axis, the y axis, and the z axis of FIG. 23 while the patient of FIG. 24 is walking forward with a normal gait at a speed of 0.9 meters/second.

FIG. 25B is a plot 2502, versus time, of the digitized versions of the analog angular-velocity signals $\Omega_x$(dps), $\Omega_y$(dps), and $\Omega_z$(dps) as a function of time that the gyroscopes of the IMU 1022 respectively generate in response to angular velocities about the x-axis 1060, the y-axis 1062, and the z-axis 1064 while the patient 1070 is walking forward with a normal gait at a speed of 0.5 meters/second and for a period of about ten seconds. In this example, the IMU 1022 samples each of the analog angular-velocity signals $\Omega_x$(dps), $\Omega_y$(dps), and $\Omega_z$(dps) and each of the analog acceleration signals $a_x$(g), $a_y$(g), and $a_z$(g) at the same sample times and at the same sampling rate of 3200 Hz and ODR of 800 Hz. That is, the plot 2502 is aligned, in time, with the plot 2500 of FIG. 25A.

As described briefly below, and in detail in PCT Publication Nos. WO 2014/209916, WO 2016/044651, WO 2017/165717 and WO 2020/247890, the acceleration signals and angular-velocity signals provided by the IMU 1022 may be processed to determine kinematic information of the patient. For example, the signals may be processed to determine a set of gait parameters including range of motion, step count, cadence, stride, and distance traveled. In general, there are three types of three-dimensional motion that the intelligent implant can detect within and around a joint: core gait (or limb mobility in the case of a shoulder or elbow arthroplasty), macroscopic instability, and microscopic instability. Details of these types of motion are described in detail in PCT Publication Nos. WO 2017/165717 and WO 2020/247890.

The step count, distance traveled, and cadence represent measures of activity and robustness of activity. The range of motion for the tibia ($ROM_{tibia}$), calculated from gyroscopic data, represents the average inclusive dynamic swing over 10-15 steps of the tibia relative to the ground in the sagittal plane. Simplistically, this can be thought of as the inclusive arc of a pendulum that is translating in the sagittal plane. The range of motion for the knee ($ROM_{knee}$) represents an average of the sagittal plane dynamic inclusive angle between the hip, femur, and tibia over a stride. This calculation will use a combination of published tabular data for hip and femur position stratified for sex, age, and BMI combined with the implant's $ROM_{tibia}$ data. This value has the same meaning as the standard of care, clinician static, goniometer measurement taken during a physical exam. However, it represents the actual dynamic range of motion during normal weight-bearing activity as opposed to a static, full capability, range of motion assessed during the physical exam. Individual values for cadence, stride, $ROM_{tibia}$, and $ROM_{knee}$ are average values calculated based on the data collected over a 24-hour period.

Shoulder Kinematic Data

Figure 26:
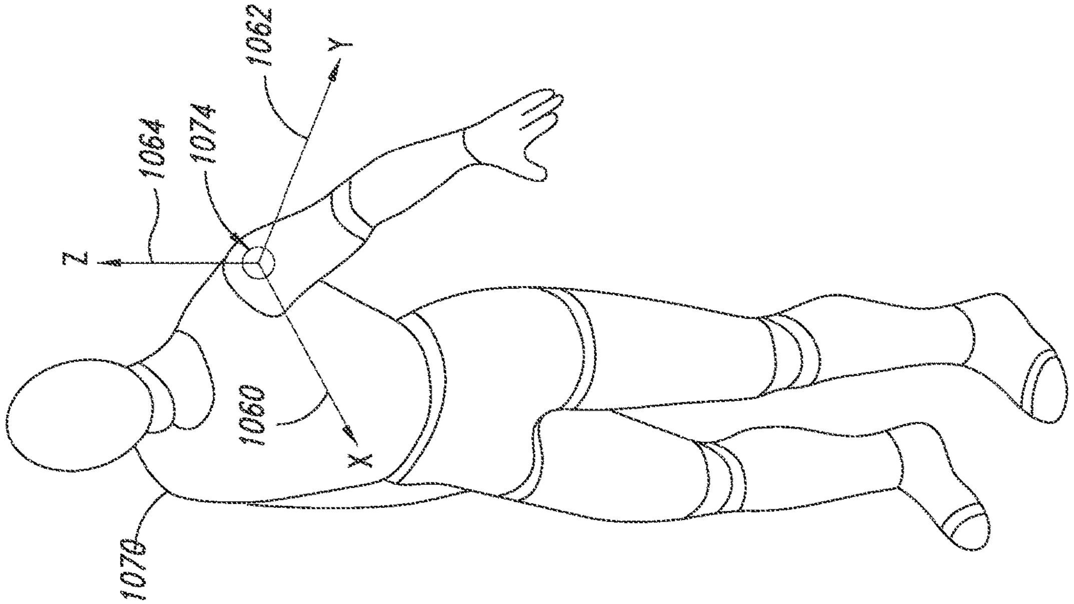
FIG. 26 is an illustration of a set of coordinate axes of an IMU relative to a patient in which a shoulder prosthesis is implanted.

FIG. 26 is an illustration of a set of coordinate axes of an IMU of an IRP relative to a patient 1070 in which a shoulder prosthesis 1074 is implanted. With respect to the anatomy of the patient, the positive portion of the x-axis 1060 extends in the anterior direction from the shoulder. The positive portion of the y-axis 1062 extends outward from the shoulder of the patient. The positive portion of the z-axis 1064 extends in the superior direction from the shoulder of the patient.

Figure 27A:
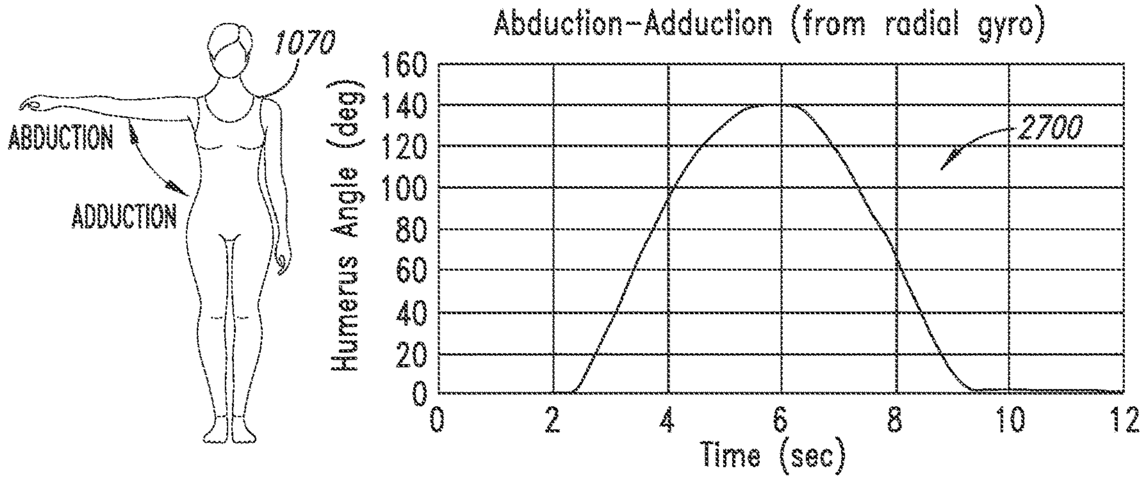
FIGS. 27A, 27B, and 27C are plots of angular-velocity (rotational-motion) signals generated in response to angular velocities about one of the x axis, the y axis, and the z axis of FIG. 23 while the patient of FIG. 26 is performing a motion.
Figure 27B:
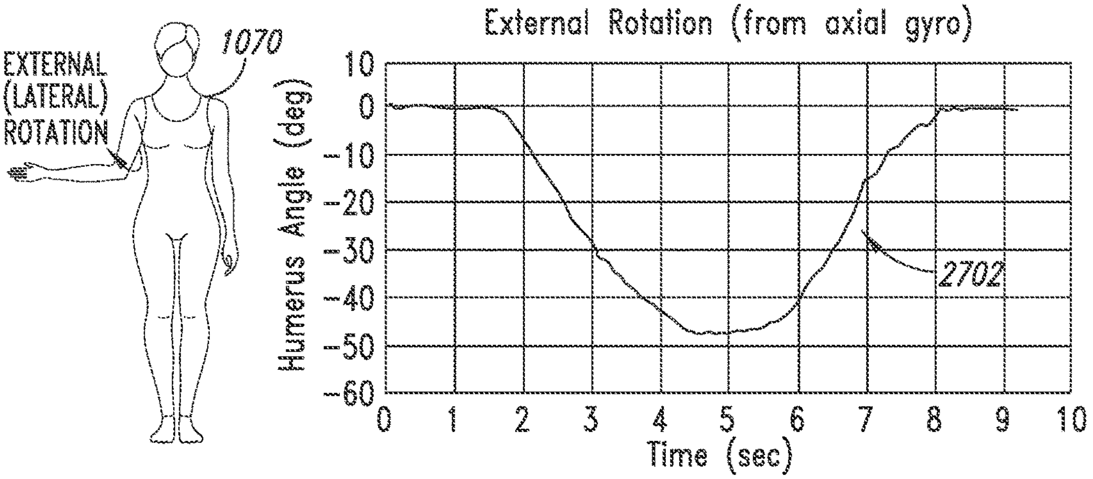
Figure 27C:
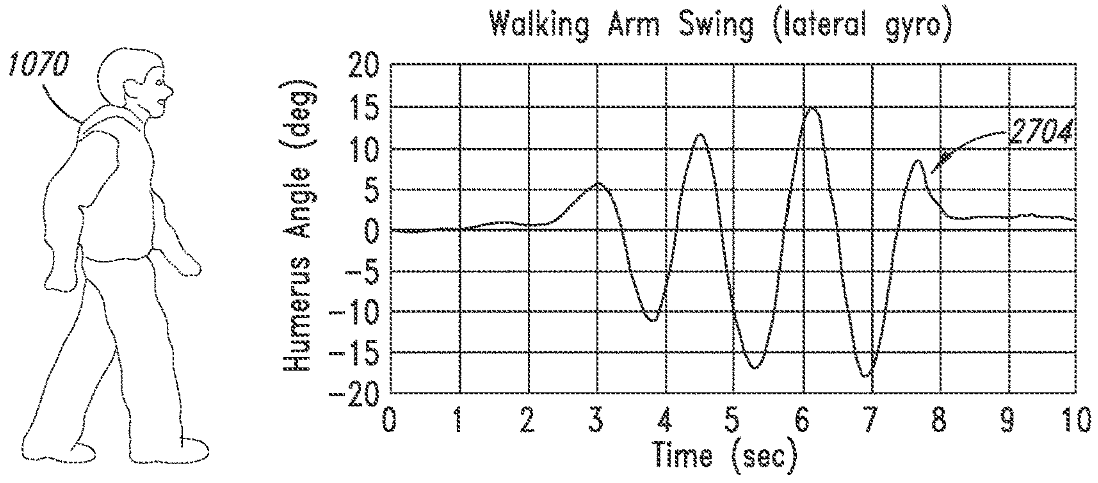

FIG. 27A is a plot 2700, versus time, of a digitized version of an analog angular-velocity signal $\Omega_x$(dps), $\Omega_y$(dps), or $\Omega_z$(dps) as a function of time that the gyroscopes of the IMU 1022 generate in response to angular velocities about the x-axis 1060, the y-axis 1062, or the z-axis 1064 while the patient 1070 is performing an abduction-adduction movement. FIG. 27B is a plot 2702, versus time, of a digitized version of an analog angular-velocity signal $\Omega_x$(dps), $\Omega_y$(dps), or $\Omega_z$(dps) as a function of time that the gyroscopes of the IMU 1022 generate in response to angular velocities about the x-axis 1060, the y-axis 1062, or the z-axis 1064 while the patient 1070 is performing an external rotation movement. FIG. 27C is a plot 2704, versus time, of a digitized version of an analog angular-velocity signal $\Omega_x$(dps), $\Omega_y$(dps), or $\Omega_2$(dps) as a function of time that the gyroscopes of the IMU 1022 generate in response to angular velocities about the x-axis 1060, the y-axis 1062, or the z-axis 1064 while the patient 1070 is performing a walking arm swing movement.

Hip Kinematic Data

Figure 28:
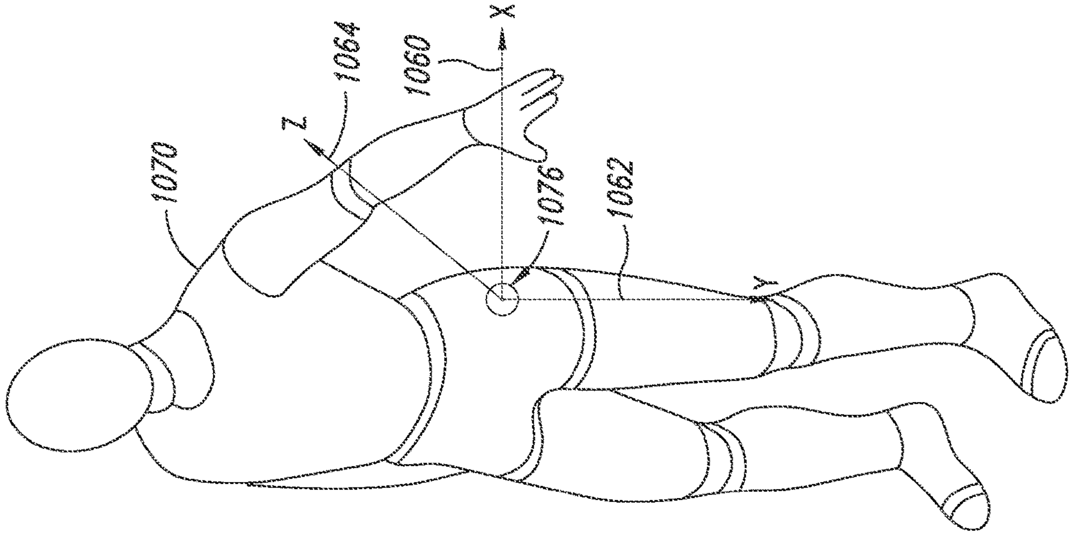
FIG. 28 is an illustration of a set of coordinate axes of an IMU relative to a patient in which a hip prosthesis is implanted.

FIG. 28 is an illustration of a set of coordinate axes of an IMU of an IRP relative to a patient 1070 in which a hip prosthesis 1076 is implanted. With respect to the anatomy of the patient, the positive portion of the x-axis 1060 extends outward from the hip of the patient. The positive portion of the y-axis 1062 extends in the inferior direction from the hip of the patient. The positive portion of the z-axis 1064 extends in the anterior direction from the hip of the patient.

Plots of the digitized versions of the analog acceleration signals $a_x$(g), $a_y$(g), and $a_z$(g) that the accelerometers of an IMU 1022 of a hip prosthesis 1076 respectively generate in response to accelerations along the x-axis 1060, the y-axis 1062, and the z-axis 1064 while the patient 1070 is walking forward with a normal gait at a speed of 0.9 meters/second are similar to the plot shown in FIG. 25A. Plots of the digitized versions of the analog angular-velocity signals $\Omega_x$(dps), $\Omega_y$(dps), and $\Omega_z$(dps) that the gyroscopes of the IMU 1022 of a hip prosthesis 1076 respectively generate in response to angular velocities about the x-axis 1060, the y-axis 1062, and the z-axis 1064 while the patient 1070 is walking forward with a normal gait at a speed of 0.5 meters/second are similar to the plot shown in FIG. 25B.

Operational Modes/States of Intelligent Implant

In some embodiments, an IRP 1003 of an intelligent implant is configured to be placed in five different modes of operation. These modes include:

Deep sleep mode: This mode places the IRP 1003 is in an ultra-low power state during storage to preserve shelf life prior to implantation. In this mode only the clock and power management 1020 circuit and the RF transceiver 1026 wake-up circuitry are active. To this end and with reference to FIG. 22, the battery 1012 provides power to the clock and power management circuit 1020 and the RF transceiver 1026 and the switches 1016, 1017, 1018 are open to decouple the battery 1012 from the IMU 1022, the accelerometer 1023 and the memory circuit 1024.

Standby mode: This mode places the IRP 1003 into a low power state, during which the implant is ready for wireless communications with an external device.

Low-resolution mode: While in this mode, the IRP 1003 collects low resolution linear acceleration data for detecting and counting simple motion events (e.g., footsteps, shoulder swings, etc.) and detection of significant motion. In some embodiments, the low-resolution mode is characterized by activation of a first set of sensors, e.g., the discrete accelerometer 1023 or one or more accelerometers of the IMU 1022, that enable the detection of simple motion events using a sampling rate in the range of 12 Hz to 100 Hz. To this end and with reference to FIG. 22, one of switches 1016, 1017 is closed to couple the battery 1012 to the IMU 1022 or the discrete accelerometer 1023.

When in low-resolution mode, the first set of sensors counts simple motion events and sends significant motion notifications to the controller 1032. When exiting the low-resolution mode, the IMU 1022 or discrete accelerometer 1023 reports a count of simple motion events to the controller 1032. The low-resolution mode may be entered on a scheduled time and exited on a schedule time in accordance with a sampling schedule. During low-resolution mode data is continuously collected by the first set of sensors.

Medium-resolution mode: While in this mode, the IRP 1003 collects both linear acceleration and rotational motion data. In some embodiments, the medium-resolution mode is characterized by activation of a second set of sensors, e.g., three accelerometers and three gyroscopes of an IMU 1022, that enable the detection of linear acceleration and rotational velocity using a sampling rate in the range of 12 Hz to 100 Hz. To this end and with reference to FIG. 22, the switch 1016 is closed to couple the battery 1012 to the IMU 1022.

The medium-resolution mode may be initiated when an unspecified detection of a significant motion event occurs during a configured medium-resolution window of the day, or by a manual command sent wirelessly from an external device, e.g., a base station. The medium-resolution mode may be exited after a pre-determined event related to the detected significant motion. For example, in the case of a significant motion corresponding to walking, the predetermined event may be a number of steps. In the case of a significant motion corresponding to arm swings, the predetermined event may be a number of swings. The medium-resolution mode may be exited after a failure to detect a significant motion.

High-resolution mode: While in this mode, the IRP 1003 may collect linear acceleration data, or it may collect both linear acceleration and rotational motion data. In some embodiments the high-resolution mode is characterized by activation of a third set of sensors, e.g., three accelerometers of an IMU 1022 (when collecting only acceleration data), or three accelerometers and three gyroscopes of the IMU (when collecting both acceleration and rotational motion data) that enable the detection of acceleration and rotational motion data using a sampling rate in the range of 200 Hz to 5000 Hz. To this end and with reference to FIG. 22, the switch 1016 is closed to couple the battery 1012 to the IMU 1022.

The high-resolution mode may be initiated when a specified detection of a significant motion event occurs during a configured medium-resolution window of the day, or by a manual command sent wirelessly from an external device. The high-resolution mode has a built-in time limit after which acquisition is automatically terminated.

These five modes are used to collect data passively and autonomously at varying frequencies during the life of the intelligent implant without patient involvement. The intelligent implant may start collecting data on post-operative day 2 and has the capability to store up to 30 days of data in memory. Thereafter, data is transmitted to the cloud daily. If the data cannot be transmitted due to connectivity issues with a base station and the implant has reached its memory limit, new data will overwrite the oldest data. Additionally, the base station can store up to 45 days of transmitted data if it is not able to connect to the cloud but is still able to communicate with the implant locally.

Data Sampling and Scheduling

Figure 29:
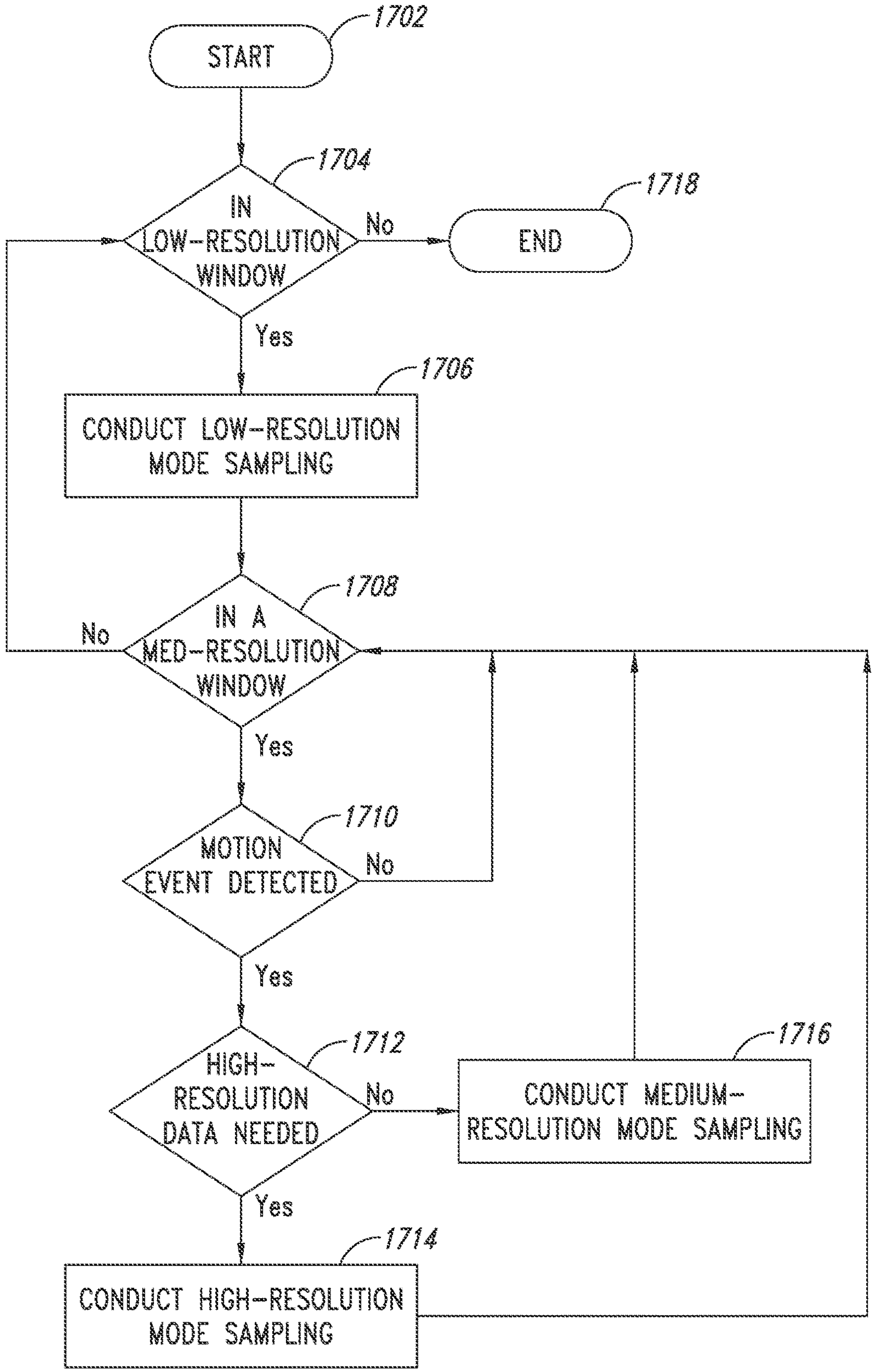
FIG. 29 is a flow chart of a method of data sampling that is implemented by the implanted reporting processor of FIG. 22.

With reference to FIG. 29, a method of sampling data from an implantable reporting processor (IRP) of an intelligent implant in the form of a knee prosthesis is described. The method may be performed by the implantable reporting processor 1003 of FIG. 22 that is configured to sample data in each of a low-resolution mode, a medium-resolution mode, and a high-resolution mode. As previously described, a low-resolution mode may be characterized by activation of a first set of sensors of the IRP 1003 that enable the detection of steps using a sampling rate in the range of 12 Hz to 100 Hz; a medium-resolution mode may be characterized by activation of a second set of sensors of the IRP that enable the detection of acceleration and rotational velocity using a sampling rate in the range of 12 Hz to 100 Hz; and a high-resolution mode may be characterized by activation of a third set of sensors of the IRP that enable the detection of acceleration using a sampling rate in the range of 200 Hz to 5000 Hz.

Continuing with FIG. 29, at block 1702 a sampling session starts. The sampling session may be scheduled to occur based on a master sampling schedule programmed into the IRP 1003. In some embodiments, the master sampling schedule has a duration of a number of years from a calendar start date. For example, the number of years may be three. The master sampling schedule includes a calendar schedule that defines when data sampling will occur. In one embodiment, the periodic sampling is a daily sampling that is conducted in accordance with a daily sampling schedule. Accordingly, in this embodiment, the method of sampling data of FIG. 29 may occur on a daily basis. The IRP 1003 is configured to allow for disabling of the master sampling schedule.

At block 1704, the IRP 1003 determines if the present time is within a low-resolution window established by the daily sampling schedule. The low-resolution window may be defined by a start time and an end time. The low-resolution window may be a portion of a 24-hour period, and may have an associated duration limit. For example, the low-resolution window may be limited to a maximum duration of 18 hours.

At block 1706, if the IRP 1003 determines the present time is within a low-resolution window, the process proceeds to block 1706, where the IRP conducts low-resolution sampling using a first set of sensors. Alternatively, if the IRP 1003 determines the present time is not within a low-resolution window, the process proceeds to block 1718 where the sampling session ends.

Returning to block 1706, the IRP 1003 conducts low-resolution sampling during the low-resolution window by detecting and counting steps of the patient. The low-resolution sampling may be continuous throughout the low-resolution window. To this end, the IRP 1003 may enable a first set of sensors to provide signal samples from which steps of the patient may be detected. The first set of sensors may be an accelerometer of the IMU 1022 or a separate accelerometer 1023. The low-resolution sampling rate may be in the range of 12 Hz to 100 Hz. In some embodiments, the IRP 1003 maintains a cumulative count of the steps that have been detected during each of a plurality of portions of the low-resolution window in its memory circuit 1024. For example, the IRP 1003 may maintain a cumulative count of steps for each hour of the low-resolution window.

Continuing with FIG. 29, at block 1708, the IRP 1003 determines if the present time is within a medium-resolution window established by the daily sampling schedule. The IRP 1003 does this "determining" concurrently with low-resolution mode sampling. A medium-resolution window may be defined by a start time and an end time, where the start time of the medium-resolution window is within the low-resolution window. In some embodiments the daily sampling schedule defines a plurality of different medium resolution windows, each of which is defined by a start time that is within the low-resolution window, and an end time. There may a maximum number of allowable individual medium-resolution windows within a daily sampling schedule. For example, in one configuration there are a maximum of three individual medium-resolution windows. These individual medium-resolution windows may be scheduled to be spaced apart within the daily schedule or they may be scheduled such that there is some overlap between the windows. In some embodiments the duration of each individual medium-resolution window is in the range of 1-4 hours. In some embodiments the duration of a medium-resolution window is 3 hours.

At block 1708, if the IRP 1003 determines the present time is within a medium-resolution window and medium-resolution data or high-resolution data has not already been collected, the process proceeds to block 1710, where the IRP detects for a significant motion event in addition to continued step counting. Alternatively, if the IRP 1003 determines the present time is not within a medium-resolution window or that scheduled medium-resolution data and high-resolution data has already been collected, the process returns to block 1704 where the IRP determines if the present time is still within a low-resolution window.

If the IRP 1003 determines the present time is within a medium-resolution window and medium-resolution data or high-resolution data has not already been collected, then at block 1710, the IRP 1003 detects for a significant motion event by sampling the analog signals output from a second set of sensors. In some embodiments, the second set of sensors include one or more of the accelerometers of the IMU 1022, or one or more of the gyroscopes of the IMU, or a separate accelerometer 1023. In the case of one or more of the accelerometers of the IMU 1022, the IMU samples the analog signals at the same sampling rate associated with the low-resolution mode. For example, the IMU 1022 samples the analog signals output from all of the x, y, and z accelerometers and gyroscopes in the range of 12 Hz to 100 Hz.

Continuing with block 1710, either the controller 1032 or the IMU 1022 determine whether the samples that the IMU 1022 obtained are samples of a significant motion event, such as the patient 1070 walking with the implanted knee prosthesis 1072. Alternatively, either the controller 1032 or the accelerometer 1023 determine whether the samples that the accelerometer 1023 obtained are samples of a significant motion event, such as the patient 1070 walking with the implanted knee prosthesis 1072. In a preferred embodiment, the separate accelerometer 1023 samples the analog signals and makes the determination if those samples constitute a significant motion event. For example, the accelerometer 1023 may correlate the respective samples from each of one or more of the accelerometers with corresponding benchmark samples (e.g., stored in memory circuit 1024 of FIG. 22) of a significant motion event, compare the correlation result to a threshold, and determines that the samples are of a significant motion event if the correlation result equals or exceeds the threshold, or determines that the samples are not of a significant motion event if the correlation result is less than the threshold. Alternatively, the accelerometer 1023 may perform a less-complex, and less energy-consuming determination by determining that the samples are of a significant motion event if, for example, the samples have a peak-to-peak amplitude and a duration that could indicate that the patient is walking for a threshold length of time. In another example, a significant motion event may correspond to a change of acceleration exceeding a threshold, and detecting the significant motion event comprises detecting a first change in acceleration that exceeds the threshold, and after a wait time, detecting a second change in acceleration that also exceeds the threshold.

Continuing with block 1710, if the IRP 1003 does not detect a significant motion event, the process returns to block 1708 where the IRP determines if the present time is still within the present medium-resolution window and medium-resolution data or high-resolution data has not already been collected. Alternatively, if the IRP 1003 detects a significant motion event, the process proceeds to block 1712, where the IRP determines if high-resolution data still needs to be collected within the present medium-resolution window. The daily sampling schedule may specify which if any medium-resolution windows should include high-resolution mode sampling.

At block 1712, if the IRP 1003 determines that high-resolution data still needs to be collected, the process proceeds to block 1714, where the IRP conducts high-resolution sampling. Alternatively, if the IRP 1003 determines that high-resolution data does not need to be collected within the current medium-resolution window, the process proceeds to block 1716 where the IRP conducts medium-resolution sampling.

Returning to block 1714, the IRP 1003 conducts high-resolution sampling by generating and storing signals indicative of three-dimensional movement. To this end, the IRP 1003 may enable a third set of sensors of the IRP 1003 to provide respective signals. The third set of sensors may be a plurality of accelerometers of the IMU 1022, wherein the respective signals represent acceleration information of the intelligent implant and the patient. In some embodiments, three accelerometers of the IMU 1022 are activated for high-resolution sampling to provide acceleration information along three axes of the IMU. The high-resolution sampling rate may be in the range of 200 Hz to 5000 Hz. This acceleration information may be processed by the controller 1032, stored in memory 1024 for subsequent transmission, or transmitted to an external device for analysis based on that data, which may be used to identify and/or address problems associated with the implanted medical device, including incorrect placement of the device, unanticipated degradation of the device, and undesired movement of the device, such as described in PCT Publication No. WO 2020/247890, the disclosure of which is incorporated herein.

In one configuration, the daily sampling schedule limits high-resolution sampling to a predetermined number of times per day. In one configuration, the number of times per day is one. The daily sampling schedule may also set the duration of the high-resolution sampling. For example, the high-resolution sampling may occur for a duration in the range of 1 second to 10 seconds. In some embodiments the duration of a high-resolution window is 3 seconds.

Returning to block 1716, the IRP 1003 conducts medium-resolution sampling by generating and storing signals indicative of three-dimensional movement. To this end, the IRP 1003 may enable a plurality of accelerometers of the IRP and a plurality of gyroscopes of the IRP to provide respective signals. The signals from the accelerometers represent acceleration information of the intelligent implant and the patient, while the signals from the gyroscopes represent angular velocity information of the intelligent implant and the patient. In some embodiments, three accelerometers of the IMU 1022 are activated for medium-resolution sampling to provide acceleration information along three axes of the IMU 1022. In some embodiments, three gyroscopes of the IMU 1022 are activated for medium-resolution sampling to provide angular velocity information about three axes of the IMU. Collectively, the acceleration information and the angular velocity information represent kinematic information of the patient. This information may be processed by the controller 1032, stored in memory 1024 for subsequent transmission, or transmitted to an external device for processing, to determine kinematic information of the patient. For example, in the case of a knee implant or a hip implant, a set of gait parameters including range of motion, step count, cadence, stride length, walking speed, and distance traveled may be determined. In the case of a shoulder implant, a set of range of motion (ROM) parameters including abduction, flexion, horizontal adduction, internal rotation, and external rotation may be determined.

The medium-resolution sampling rate may be in the range of 12 Hz to 100 Hz. The medium-resolution sampling may be conducted a limited number of times during the medium-resolution window. In one configuration, the daily sampling schedule limits medium-resolution sampling to once per medium-resolution window. The daily sampling schedule may also set the duration of the medium-resolution sampling. For example, the medium-resolution sampling may occur for a duration in the range of 5 seconds to 30 seconds. In some embodiments the duration of a high-resolution window is 10 seconds.

In addition to the schedule periodic data sampling of FIG. 29, the IRP 1003 may be configured to sample data in response to the receipt of an on-demand start command. The on-demand start command may be received by the IRP 1003 from an external device. The on-demand start command may specify the sampling mode, e.g., medium-resolution sampling (block 1716 of FIG. 29) or high-resolution sampling (block 1714 of FIG. 29), and a duration of the sampling, which may be in the range of 1 seconds to 30 seconds. The start command may also specify the sampling rate.

Intelligent Implant Diagnostics

The IRP 1003 of an intelligent implant may be configured to accumulate diagnostic information, e.g., event count and duration information, that can be used toward implant longevity determination. Example diagnostic information includes a count of the number of controller 1032 reset events that have occurred during the implant lifetime, the number of seconds that the implant has been in a telemetry session during the implant lifetime, a count of the total number of sectors written in flash memory during the implant lifetime, and a count of the total number of sectors erased in flash memory during the implant lifetime. Other example diagnostic information includes the number of seconds that the implant has been in a low-resolution window during the implant lifetime, a count of the number of controller 1032 reset events that have occurred during the implant lifetime, the number of seconds that the implant has been in a medium-resolution window during the implant lifetime, and the number of seconds that the implant has been in a high-resolution window during the implant lifetime. Still other example diagnostic information includes record the number of seconds that the implant has been in medium-resolution mode due to on-demand operation during the current day, record the number of seconds that the implant has been in high-resolution mode due to on-demand operation during the current day, and record the voltage of the battery at the start of the last low-resolution window that occurred.

Clinical Applications

The following disclosure focuses on a full or partial shoulder joint replacement, particularly involving replacement of the humerus, however this disclosure more generally applies to any of the medical implants as disclosed herein. Currently, post-operative, in-hospital monitoring of shoulder replacement surgery patients is conducted through personal visits by the hospital staff and medical team, physical examination of the patient, medical monitoring (vital signs, etc.), evaluation of shoulder range of motion (ROM), physiotherapy (including early mobilization and activity), and diagnostic imaging studies and blood work as required. Once the patient is discharged from hospital, prosthesis performance and patient satisfaction is checked during periodic doctor's office visits where a thorough history, physical exam and supplemental imaging and diagnostic studies are used to monitor patient progress and identify the development of any potential complications. During such visits, the surgeon typically evaluates the range of motion of the shoulder, attempts to identify any pain that occurs during certain motions or actions, and questions the patient to determine activity levels, daily functioning, pain control, and rehabilitation progress.

Unfortunately, most of the patient's recuperative period occurs between hospital and/or office visits. It can, therefore, be very difficult to accurately measure and follow full joint range of motion (ROM can change depending on pain control, degree of anti-inflammatory medication, time of day, recent activities, and/or how the patient is feeling at the time of the examination), "real life" prosthesis performance, patient activity levels, exercise tolerance, and the effectiveness of rehabilitation efforts (physiotherapy, medications, etc.) from the day of surgery through to full recovery. For much of this information, the physician is dependent upon patient self-reporting or third party observation to obtain insight into post-operative treatment effectiveness and recovery and rehabilitation progress; in many cases this is further complicated by a patient who is uncertain what to look for, has no knowledge of what "normal/expected" post-operative recovery should be, is non-compliant, or is unable to effectively communicate their symptoms. Furthermore, identifying and tracking complications (in and out of hospital) prior to them becoming symptomatic, arising between doctor visits, or those whose presence is difficult for the patient (and/or the physician) to detect would also provide beneficial, additional information to the management of shoulder replacement patients. Currently, in all instances, neither the physician nor the patient has access to the type of "real time," continuous, objective, prosthesis performance measurements that they might otherwise like to have.

The present disclosure provides novel shoulder replacements which overcome many of the difficulties of previous shoulder prostheses, methods for constructing and monitoring these novel shoulder replacements, and further provides other related advantages.

According to one embodiment, the sensors provide evaluation data on the range of motion (ROM) of the shoulder. Currently, ROM is usually measured clinically by the physician passively moving the shoulder joint through a full range of motion during physical examination and recording the results (degrees of flexion, extension, abduction, adduction, external and internal rotation). Motion sensors and accelerometers can be used to accurately determine the full ROM of the prosthetic shoulder joint both during physical examination and during normal daily activities between visits. Similarly, motion sensors and accelerometers can be used to accurately measure any instability (including full, partial, or subclinical dislocation) of the prosthetic shoulder joint both during physical examination and during normal daily activities between visits.

During shoulder replacement surgery, the prosthetic joint will be moved through a full range of motion and stability testing to assess prosthetic function and mobility prior to surgical closure. The accelerometers of an implant of the present disclosure can provide the surgeon with accurate, numeric, quantitative range of motion data at that time; this data can be compared to expected values to assess efficacy of the implantation surgery and can serve as a baseline value for comparison to functional values obtained post-operatively. Any abnormalities in vibration (indicative of an inadequate anchoring of the prosthesis to the surrounding bone), tilt (indicative of improper tracking and/or alignment of the shoulder joint), rotation (indicative of dislocation or subluxation), and/or range of motion (acting in conjunction with the pectoral girdle, a properly functioning shoulder joint allows for a wide range of motion at the upper limb, notably flexion, extension, abduction, adduction, external/lateral rotation, internal/medial rotation and circumduction) can be addressed at this time and allow the surgeon to make adjustments intra-operatively.

Shortly after the shoulder joint or a portion thereof (e.g., a prosthetic humerus as disclosed herein) has been replaced, and following a suitable post-operative recuperating period, the upper arm will be mobilized post-operatively, at first passively, then actively; shortly after recovering from the procedure, the patient will begin gradual movement of the shoulder joint. The accelerometers can measure the movement and tracking of the shoulder joint during movement. In addition, the accelerometers can measure the impact of the arm as the associated hand contacts various objects. As the patient continues to improve their range of motion postoperatively, the acceleration experienced at different locations in the prosthetic shoulder joint, e.g., the prosthetic humerus, can be monitored. It will be expected that as the patient heals from the surgery, activity levels will progressively increase, and movement and shoulder usage will improve and increase. The effects of exercise and various activities can be monitored by the various accelerometers and can be compared to patient's subjective experiences to determine which life activities are improving (or inhibiting) post-operative recovery and rehabilitation.

Integrating the data collected by the sensors described herein (e.g., accelerometers and gyroscopes) with simple, widely available, commercial analytical technologies such as pedometers and global positioning satellite (GPS) capability, allows further clinically important data to be collected such as, but not restricted to: patient activity levels (frequency of activity, duration, intensity), exercise tolerance (work, calories, power, training effect), range of motion (discussed elsewhere herein) and prosthesis performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, stiffness, time of day, compliance and timing of medication use (pain medications, anti-inflammatories), recent activity and exercise levels, patient strength, mental status, language barriers, the nature of their doctor-patient relations, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, exercise, physiotherapy, anti-inflammatory medication, rest, etc.), and to compare rehabilitation progress versus previous function and future expected function. Better therapeutic decisions and better patient compliance can be expected when both the doctor and the patient have the benefit of observing the impact of various treatment modalities on patient rehabilitation, activity, function, and overall performance.

The devices, methods, systems etc. of the present disclosure have been described broadly and generically herein. Each of the narrower species and subgeneric groupings falling within the generic disclosure also form part of the present disclosure. This includes the generic description of the devices, methods, systems etc. of the present disclosure with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the present disclosure are described in terms of Markush groups, it is intended, and those skilled in the art will recognize, that the present disclosure embraces and is also thereby described in terms of any individual member and any subgroup of members of the Markush group, and Applicants reserve the right to revise the application or claims to refer specifically to any individual member or any subgroup of members of the Markush group.

It is to be understood that the terminology used herein is for the purpose of describing specific embodiments only and is not intended to be limiting. It is further to be understood that unless specifically defined herein, the terminology used herein is to be given its traditional meaning as known in the relevant art.

Reference throughout this specification to "one embodiment" or "an embodiment" and variations thereof means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents, i.e., one or more, unless the content and context clearly dictates otherwise. For example, the term "a sensor" refers to one or more sensors, and the term "a medical device comprising a sensor" is a reference to a medical device that includes at least one sensor. A plurality of sensors refers to more than one sensor. It should also be noted that the conjunctive terms, "and" and "or" are generally employed in the broadest sense to include "and/or" unless the content and context clearly dictates inclusivity or exclusivity as the case may be. Thus, the use of the alternative (e.g., "or") should be understood to mean either one, both, or any combination thereof of the alternatives. In addition, the composition of "and" and "or" when recited herein as "and/or" is intended to encompass an embodiment that includes all of the associated items or ideas and one or more other alternative embodiments that include fewer than all of the associated items or ideas.

Unless the context requires otherwise, throughout the specification and claims that follow, the word "comprise" and synonyms and variants thereof such as "have" and "include," as well as variations thereof such as "comprises" and "comprising" are to be construed in an open, inclusive sense, e.g., "including, but not limited to." The term "consisting essentially of" limits the scope of a claim to the specified materials or steps, or to those that do not materially affect the basic and novel characteristics of the claimed invention.

Any headings used within this document are only being utilized to expedite its review by the reader, and should not be construed as limiting the disclosure, invention or claims in any manner. Thus, the headings and Abstract of the Disclosure provided herein are for convenience only and do not interpret the scope or meaning of the embodiments.

Where a range of values is provided herein, it is understood that each intervening value, to the tenth of the unit of the lower limit unless the context clearly dictates otherwise, between the upper and lower limit of that range and any other stated or intervening value in that stated range is encompassed within the disclosure, invention, or claims. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

For example, any concentration range, percentage range, ratio range, or integer range provided herein is to be understood to include the value of any integer within the recited range and, when appropriate, fractions thereof (such as one tenth and one hundredth of an integer), unless otherwise indicated. Also, any number range recited herein relating to any physical feature, such as polymer subunits, size, or thickness, are to be understood to include any integer within the recited range, unless otherwise indicated. As used herein, the term "about" means±20% of the indicated range, value, or structure, unless otherwise indicated.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Such documents may be incorporated by reference for the purpose of describing and disclosing, for example, materials and methodologies described in the publications, which might be used in connection with the present disclosure. The publications discussed above and throughout the text are provided solely for their disclosure prior to the filing date of the present application. Nothing herein is to be construed as an admission that the inventors are not entitled to antedate any referenced publication by virtue of prior invention.

All patents, publications, scientific articles, web sites, and other documents and materials referenced or mentioned herein are indicative of the levels of skill of those skilled in the art to which the disclosure pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Furthermore, the written description portion of this patent includes all claims. Furthermore, all claims, including all original claims as well as all claims from any and all priority documents, are hereby incorporated by reference in their entirety into the written description portion of the specification, and Applicants reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

Other nonlimiting embodiments are within the following claims. The patent may not be interpreted to be limited to the specific examples or nonlimiting embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

As mentioned above, in the following claims, the terms used should not be construed to limit the claims to the specific embodiments disclosed in the specification and the claims, but should be construed to include all possible embodiments along with the full scope of equivalents to which such claims are entitled. For example, described embodiments with one or more omitted components or steps can be additional embodiments contemplated and covered by this application.

What is claimed is:

1. An intelligent implant comprising:

a component of an implantable prosthesis; and an implantable reporting processor associated with the component and comprising:

a housing having a casing and a cover coupled to the casing, an electronics assembly within the housing, and an antenna within the housing and coupled to the electronics assembly, the antenna comprising a flat ribbon configured in a loop having a first end, a second end opposite the first end, and opposed sides that extend between the first end and the second end, the opposed sides having major surfaces defined by a length and a height of the flat ribbon and minor edges defined by a thickness of the flat ribbon, the antenna oriented within the cover of the housing with major surfaces of the antenna generally parallel with an inner surface of the cover and the minor edges generally perpendicular to the major surfaces.

2. The intelligent implant of claim 1, wherein the height of the flat ribbon is greater than the thickness of the flat ribbon.

3. The intelligent implant of claim 1, wherein:

the cover comprises a dome-shaped closed end, and the first end of the antenna is in the dome-shaped closed end.

4. The intelligent implant of claim 1, wherein:

the cover comprises a sidewall that extends from a dome-shaped closed end, and the opposed sides of the antenna are surrounded by the sidewall.

5. The intelligent implant of claim 1, wherein:

the second end of the antenna is electrically coupled to the electronics assembly.

6. The intelligent implant of claim 5, wherein:

the second end of the antenna comprises a first portion separated by a gap from a second portion, the first portion includes a first notch at an edge configured to couple with a first feedthrough pin of the electronics assembly, and the second portion includes a second notch at an edge configured to couple with a second feedthrough pin of the electronics assembly.

7. The intelligent implant of claim 1, wherein the antenna is formed of a material comprising:

platinum (Pt) with an atomic percentage in a range of 70% to 100%, and iridium (Ir) with an atomic percentage in a range of 0% to 30%.

8. The intelligent implant of claim 7, wherein the material is Pt90Ir10.

9. The intelligent implant of claim 1, wherein the major surfaces of the antenna have a surface finish in a range of 0 micro inches and 15 micro inches maximum.

10. The intelligent implant of claim 9, wherein the surface finish is 6 micro inches maximum.

11. The intelligent implant of claim 1, wherein the implantable reporting processor further comprises an epoxy material that fills the cover and encapsulates the antenna.

12. The intelligent implant of claim 1, wherein the implantable prosthesis is a tibial component of a knee prosthesis, and the implantable reporting processor is mechanically coupled to a tibial stem of the tibial component.

13. The intelligent implant of claim 12, wherein the tibial component comprises a tibial plate configured for fixation with a tibia in an absence of cement and the tibial stem extends from the tibial plate.

14. The intelligent implant of claim 1, wherein the implantable prosthesis is a humeral component of a shoulder prosthesis, and the implantable reporting processor is mechanically coupled to the humeral component.

15. The intelligent implant of claim 1, wherein the implantable prosthesis is a femoral component of a hip prosthesis, and the implantable reporting processor is mechanically coupled to the femoral component.

16. The intelligent implant of claim 2, wherein the height of the flat ribbon is approximately 10 times greater than the thickness of the flat ribbon.

17. A tibial component of a knee prosthesis, the tibial component comprising:

a tibial stem; and a tibial extension mechanically coupled to and partially extending from the tibial stem, the tibial stem extension comprising:

a housing having a casing and a cover coupled to the casing, an electronics assembly within the housing, and an antenna within the housing and coupled to the electronics assembly, the antenna comprising a flat ribbon configured in a loop having a first end, a second end opposite the first end, and opposed sides that extend between the first end and the second end, the opposed sides having major surfaces defined by a length and a height of the flat ribbon and minor edges defined by a thickness of the flat ribbon, the antenna oriented within the cover of the housing with major surfaces of the antenna generally parallel with an inner surface of the cover and the minor edges generally perpendicular to the major surfaces.

18. A tibial component of a knee prosthesis, the tibial component comprising:

a tibial stem having a receptacle; and an implantable reporting processor partially within the receptacle and partially extending from the tibial stem, the implantable reporting processor comprising:

a battery within the receptacle, an electronics assembly coupled to the battery and within the receptacle, an antenna coupled to the electronics assembly and outside the receptacle, the antenna comprising a flat ribbon configured in a loop having a first end, a second end opposite the first end, and opposed sides that extend between the first end and the second end, the opposed sides having major surfaces defined by a length and a height of the flat ribbon and minor edges defined by a thickness of the flat ribbon, and a cover outside the receptacle and enclosing the antenna, wherein the antenna is oriented within the cover with major surfaces of the antenna generally parallel with an inner surface of the cover and the minor edges generally perpendicular to the major surfaces.

19. The tibial component of claim 18, wherein the implantable reporting processor further comprises an antenna feedthrough assembly coupled between the electronics assembly and the antenna, and at least partially within the receptacle.

* * * * *